United States Patent [19]

Maraganore et al.

[11] Patent Number: 5,691,311
[45] Date of Patent: Nov. 25, 1997

US005691311A

[54] METHODS FOR COATING INVASIVE DEVICES WITH INHIBITORS OF THROMBIN

[75] Inventors: John M. Maraganore, Concord, Mass.; John W. Fenton, II, Malden Bridge, N.Y.; Toni Kline, Cambridge, Mass.

[73] Assignee: Biogen, Inc., Cambridge, Mass.

[21] Appl. No.: 439,297

[22] Filed: May 11, 1995

Related U.S. Application Data

[60] Division of Ser. No. 834,259, Feb. 10, 1992, Pat. No. 5,433,940, which is a continuation-in-part of Ser. No. 549,388, Jul. 6, 1990, Pat. No. 5,196,404, which is a continuation-in-part of Ser. No. 395,482, Aug. 18, 1989, abandoned.

[51] Int. Cl.$^6$ ................................................ A61K 38/00
[52] U.S. Cl. .................. 514/12; 424/1.69; 514/13; 514/14; 530/324; 530/326; 530/327; 623/11
[58] Field of Search .................. 514/12, 13, 14; 623/11; 424/1.69; 530/329, 324, 326, 327

[56] References Cited

U.S. PATENT DOCUMENTS

| | | | |
|---|---|---|---|
| 5,196,404 | 3/1993 | Maraganore et al. | 514/13 |
| 5,433,940 | 7/1995 | Maraganore et al. | 424/1.69 |

OTHER PUBLICATIONS

Bajusz et al, Peptides, 1984, Almquist and Wiksell Intl., 473–476.
Chang, FEBS Lett. 164, pp. 307–313 (1983).
DiMaio et al, J. Biol. Chem. 265, pp. 21698–21703 (1990).
Kettner et al, Thromb. Res. 14, pp. 969–973 (1979).
Maraganore et al, J. Biol. Chem. 264, pp. 8692–8698 (1989).
Markwardt, Noov. Rev. Fr. Hematol. 30, pp. 161–165 (1988).
Rauber and Shaw, Analytical Biochem. 168, 259–264 (1988).
Dodt et al, FEBS Lett. 165, 180–184 (1984).

*Primary Examiner*—Howard E. Schain
*Attorney, Agent, or Firm*—Fish & Neave; James F. Haley, Jr.; Andrew S. Marks

[57] ABSTRACT

This invention relates to novel biologically active molecules which bind to and inhibit thrombin. Specifically, these molecules are characterized by a thrombin anion-binding exosite association moiety (ABEAM); a linker portion of at least 18 Å in length; and a thrombin catalytic site-directed moiety (CSDM). This invention also relates to compositions, combinations and methods which employ these molecules for therapeutic, prophylactic and diagnostic purposes.

15 Claims, 13 Drawing Sheets

* p<0.01 vs Control
a p<0.05 vs Heparin

METHODS FOR COATING INVASIVE DEVICES WITH INHIBITORS OF THROMBIN

CROSS REFERENCE TO PRIOR APPLICATIONS

This application is a division of U.S. application Ser. No. 07/834,259, filed Feb. 10, 1992, now U.S. Pat. No. 5,433,940, issued Jul. 18, 1995, which is a continuation-in-part of U.S. application Ser. No. 07/549,388, filed Jul. 6, 1990, now U.S. Pat. No. 5,196,404, issued Mar. 23, 1993, which is a continuation-in-part of U.S. application Ser. No. 07/395,482, filed Aug. 18, 1989, now abandoned.

TECHNICAL FIELD OF INVENTION

This invention relates to novel biologically active molecules which bind to and inhibit thrombin. Specifically, these molecules are characterized by a thrombin anion-binding exosite associating moiety (ABEAM); a linker portion of at least 18 Å in length; and a thrombin catalytic site-directed moiety (CSDM). This invention also relates to compositions, combinations and methods which employ these molecules for therapeutic, prophylactic and diagnostic purposes.

BACKGROUND ART

Acute vascular diseases, such as myocardial infarction, stroke, pulmonary embolism, deep vein thrombosis, peripheral arterial occlusion, and other blood system thromboses constitute major health risks. Such diseases are caused by either partial or total occlusion of a blood vessel by a blood clot, which contains fibrin and platelets.

Current methods for the treatment and prophylaxis of thrombotic diseases involve therapeutics which act in one of two different ways. The first type of therapeutic inhibits thrombin activity or thrombin formation, thus preventing clot formation. These drugs also inhibit platelet activation and aggregation. The second category of therapeutic accelerates thrombolysis and dissolves the blood clot, thereby removing it from the blood vessel and unblocking the flow of blood [J. P. Cazenave et al., Agents Action, 15, Suppl., pp. 24–49 (1984)].

Heparin, a compound of the former class, has been widely used to treat conditions, such as venous thromboembolism, in which thrombin activity is responsible for the development or expansion of a thrombus. Although effective, heparin produces many undesirable side effects, including hemorrhaging and thrombocytopenia. This has led to a search for a more specific and less toxic anticoagulant.

Hirudin is a naturally occurring polypeptide which is produced by the blood sucking leech Hirudo medicinalis. This compound, which is synthesized in the salivary gland of the leech, is the most potent natural inhibitor of coagulation known. Hirudin prevents blood from coagulating by binding tightly to thrombin ($K_d=2\times10^{-11}$M) in a 1:1 stoichiometric complex [S. R. Stone and J. Hofsteenge, "Kinetics of the Inhibition of Thrombin by Hirudin", Biochemistry, 25, pp. 4622–28 (1986)]. This, in turn, inhibits thrombin from catalyzing the conversion of fibrinogen to fibrin (clot), as well as inhibiting all other thrombin-mediated processes [J. W. Fenton, II, "Regulation of Thrombin Generation and Functions", Semin. Thromb. Hemost., 14, pp. 234–40 (1988)].

The actual binding between hirudin and thrombin is a two-step process. Initially, hirudin binds to a "low" affinity site on the thrombin molecule ($K_d=1\times10^{-8}$M) which is separate from the catalytic site. This binding involves interaction of structure from the C-terminus of hirudin with an "anion-binding exosite" (ABE) in thrombin [J. W. Fenton, II et al., "Thrombin Anion Binding Exosite Interactions with Heparin and Various Polyanions", Ann. New York Acad. Sci., 556, pp. 158–65 (1989)]. Following the low affinity binding, the hirudin-thrombin complex undergoes a conformational change and hirudin then binds to the "high" affinity site on thrombin [S. Kono et al., "Analysis of Secondary Structure of Hirudin and the Conformational Change Upon Interaction with Thrombin", Arch. Biochem. Biophys., 267, pp. 158–66 (1988)]. This latter site corresponds to the active site of thrombin.

The isolation, purification and chemical composition of hirudin are known in the art [P. Walsmann and F. Markwardt, "Biochemical and Pharmacological Aspects of the Thrombin Inhibitor Hirudin", Pharmazie, 36, pp. 653–60 (1981)]. More recently, the complete amino acid sequence of the polypeptide has been elucidated [J. Dodt et al., "The Complete Covalent Structure of Hirudin: Localization of the Disulfide Bonds", Biol. Chem. Hoppe-Seyler, 366, pp. 379–85 (1985); S. J. T. Mao et al., "Rapid Purification and Revised Amino Terminal Sequence of Hirudin: A Specific Thrombin Inhibitor of the Blood-Sucking Leech", Anal. Biochem, 161, pp. 514–18 (1987); and R. P. Harvey et al., "Cloning and Expression of a cDNA Coding for the Anti-Coagulant Hirudin from the Bloodsucking Leech, Hirudo medicinalis", Proc. Natl. Acad. Sci. USA, 83, pp. 1084–88 (1986)].

At least ten different isomorphic forms of hirudin have been sequenced and have been shown to differ slightly in amino acid sequence [D. Tripier, "Hirudin: A Family of Iso-Proteins. Isolation and Sequence Determination of New Hirudins", Folia Haematol., 115, pp. 30–35 (1988)]. All forms of hirudin comprise a single polypeptide chain protein containing 65 or 66 amino acids in which the amino terminus primarily comprises hydrophobic amino acids and the carboxy terminus typically comprises polar amino acids. More specifically, all forms of hirudin are characterized by an N-terminal domain (residues 1–39) stabilized by three disulfide bridges in a 1–2, 3–5, and 4–6 half-cysteinyl pattern and a highly acidic C-terminal segment (residues 40–65). In addition, the C-terminal segment of hirudin is characterized by the presence of a tyrosine residue at amino acid position 63 which is sulfated.

In animal studies, hirudin, purified from leeches, has demonstrated efficacy in preventing venous thrombosis, vascular shunt occlusion and thrombin-induced disseminated intravascular coagulation. In addition, hirudin exhibits low toxicity, little antigenicity and a very short clearance time from circulation [F. Markwardt et al., "Pharmacological Studies on the Antithrombotic Action of Hirudin in Experimental Animals", Thromb. Haemost., 47, pp. 226–29 (1982)].

In an effort to create a greater supply of hirudin, attempts have been made to produce the polypeptide through recombinant DNA techniques. The presence of an O-sulfated tyrosine residue on native hirudin and the inability of microorganisms to perform a similar protein modification made the prospect of recombinant production of biologically active hirudin highly speculative. The observation that desulfatohirudins were almost as active as their sulfated counterparts [U.S. Pat. No. 4,654,302], however, led the way to the cloning and expression of hirudin in E. coli [European patent applications 158,564, 168,342 and 171,024] and yeast [European patent application 200,655]. Despite these advances, hirudin is still moderately expensive to produce and it is not widely available commercially.

Recently, efforts have been made to identify peptide fragments of native hirudin which are also effective in prolonging clotting times. An unsulfated 21 amino acid C-terminal fragment of hirudin, N-acetylhirudin$_{45-65}$, inhibits clot formation in vitro. In addition, several other smaller, unsulfated peptides corresponding to the C-terminal 11 or 12 amino acids of hirudin (residues 55-65 and 54-65) have also demonstrated efficacy in inhibiting clot formation in vitro [J. L. Krstenansky et al., "Antithrombin Properties of C-terminus of Hirudin Using Synthetic Unsulfated N-acetyl-hirudin$_{45-65}$", FEBS Lett, 211, pp. 10-16 (1987)]. Such peptide fragments, however, may not be fully satisfactory to dissolve blood clots in on-going therapy regimens because of low activity. For example, N-acetyl-hirudin$_{45-65}$ has a specific activity four orders of magnitude lower than native hirudin.

In addition to catalyzing the formation of a fibrin clot, thrombin has several other bioregulatory roles [J. W. Fenton, II, "Thrombin Bioregulatory Functions", Adv. Clin. Enzymol., 6, pp. 186-93 (1988)]. For example, thrombin directly activates platelet aggregation and release reactions. This means that thrombin plays a central role in acute platelet-dependent thrombosis [S. R. Hanson and L. A. Harker, "Interruption of Acute Platelet-Dependent Thrombosis by the Synthetic Antithrombin D-Phenylalanyl-L-Prolyl-L-Arginylchloromethylketone", Proc. Natl. Acad. Sci. USA, 85, pp. 3184-88 (1988)]. Thrombin can also directly activate an inflammatory response by stimulating the synthesis of platelet activating factor (PAF) in endothelial cells [S. Prescott et al., "Human Endothelial Cells in Culture Produce Platelet-Activating Factor (1-alkyl-2-acetyl-sn-glycero-3-phosphocholine) When Stimulated With Thrombin", Proc Natl. Acad. Sci. USA, 81, pp. 3534-38 (1984)]. PAF is exposed on the surface of endothelial cells and serves as a ligand for neutrophil adhesion and subsequent degranulation [G. M. Vercolletti et al., "Platelet-Activating Factor Primes Neutrophil Responses to Agonists: Role in Promoting Neutrophil-Mediated Endothelial Damage", Blood 71 pp 1100-07 (1988)]. Alternatively, thrombin may promote inflammation by increasing vascular permeability which can lead to edema [P. J. Del Vecchio et al., "Endothelial Monolayer Permeability To Macromolecules", Fed. Proc., 46, pp. 2511-15 (1987)]. Reagents which block the active site of thrombin, such as hirudin, interrupt the activation of platelets and endothelial cells [C. L. Knupp, "Effect of Thrombin Inhibitors on Thrombin-Induced Release and Aggregation", Thrombosis Res., 49, pp. 23-36 (1988)].

Thrombin has also been implicated in promoting cancer, based on the ability of its native digestion product, fibrin, to serve as a substrate for tumor growth [A. Falanga et al., "Isolation and Characterization of Cancer Procoagulant: A Cysteine Proteinase from Malignant Tissue", Biochemistry, 24, pp. 5558-67 (1985); S. G. Gordon et al., "Cysteine Proteinase Procoagulant From Amnion-Chorion", Blood, 66, pp. 1261-65 (1985); and A. Falanga et al., "A New Procoagulant In Acute Leukemia", Blood, 71, pp. 870-75 (1988)]. And thrombin has been implicated in neurodegenerative diseases based on its ability to cause neurite retraction [D. Gurwitz et al., "Thrombin Modulates and Reverses Neuroblastoma Neurite Outgrowth", Proc. Natl. Acad. Sci USA, 85, pp. 3440-44 (1988)]. Therefore, the ability to regulate the in vivo activity of thrombin has many important clinical implications.

Despite the developments to date, the need still exists for a molecule that effectively inhibits thrombin function in clot formation, platelet activation and various other thrombin-mediated processes and which can be produced inexpensively and in commercially feasible quantities.

SUMMARY OF THE INVENTION

The present invention solves the problems enumerated above by providing molecules which mimic the action of hirudin by binding to both the low affinity anion-binding exosite (ABE) and the catalytic site of α-thrombin. These molecules are more potent than hirudin and, therefore, they may be administered to patients in dosages which are comparatively lower than those required in hirudin-based therapy regimens. The molecules of this invention may be utilized in compositions and methods for inhibiting any thrombin-mediated or thrombin-associated function or process. Pharmaceutical compositions containing these molecules, as well as methods of treatment or prophylaxis of vascular diseases, inflammatory responses, carcinomas, and neurodegenerative diseases using them are also part of the present invention. These molecules may also be employed in compositions and methods for ex vivo imaging, for storing and treating extracorporeal blood and for coating invasive devices. And the molecules of this invention may be administered to a patient in combination with a fibrinolytic agent to increase the efficacy of a given dose of that agent or to lower the dose of that agent required for a given effect, such as dissolving a blood clot.

Due to their high potency and the fact that they may be prepared by chemical synthesis techniques, the molecules of the present invention may be prepared inexpensively, in commercially feasible amounts. Moreover, because the molecules of the present invention are significantly smaller than hirudin, they are less likely to stimulate an undesirable immune response in patients treated with them. Accordingly, the use of these thrombin inhibitors is not limited to the treatment of acute disease. These molecules may also be utilized in therapy for chronic thromboembolic diseases, such atherosclerosis and restenosis following angioplasty. The molecules of the present invention may also be utilized in a variety of other applications in place of natural or recombinant hirudin.

As will be appreciated from the disclosure to follow, the molecules, compositions and methods of this invention are useful in the treatment and prevention of various diseases attributed to the undesirable effects of thrombin, as well as for diagnostic purposes.

DETAILED DESCRIPTION OF THE INVENTION

Figure 1:
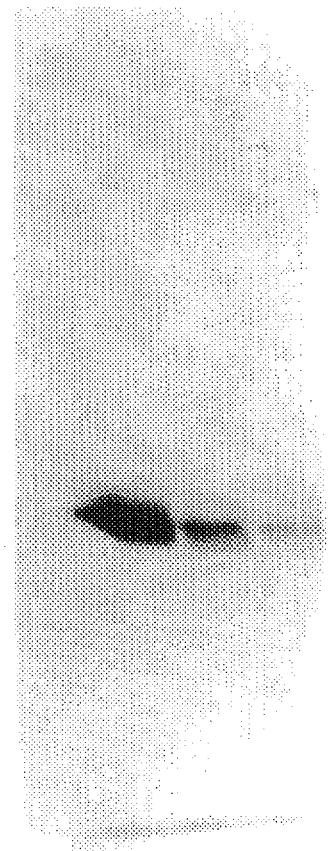
FIG. 1 depicts an autoradiograph of an SDS-polyacrylamide gel demonstrating the binding of DNFB-[$^{35}$S]-Sulfo-Tyr$_{63}$hirudin$_{54-64}$ to human α-thrombin in the presence or absence of Sulfo-Tyr$_{63}$-N-acetyl-hirudin$_{53-64}$.

The following common abbreviations of the amino acids are used throughout the specification and in the claims:
Orn—ornithine Gly—glycine
Ala—alanine Val—valine
Leu—leucine Ile—isoleucine
Pro—proline Phe—phenylalanine
Trp—tryptophan Met—methionine
Ser—serine Thr—threonine
Cys—cysteine Tyr—tyrosine
Asn—asparagine Gln—glutamine
Asp—aspartic acid Glu—glutamic acid
Lys—lysine Arg—arginine
His—histidine Nle—norleucine
Hyp—hydroxyproline Pgl—phenylglycine
Ac—acetyl Suc—succinyl
BOC—tertButoxycarbonyl Tos—paraToluenesulfonyl
Cbz—Carbobenzyloxy D-Ala—D-alanine
3,4,-dehydroPro—3,4,-dehydroproline Sar—sarcosine (N-methylglycine)
$Tyr(OSO_3H)$—tyrosine sulfate $Tyr(SO_3H)$—tyrosine sulfonate
3-, 5-diiodoTyr—3-,5-diiodotyrosine The term "any amino acid" as used herein includes the L-isomers of the naturally occurring amino acids, as well as other "non-protein" α-amino acids commonly utilized by those in the peptide chemistry arts when preparing synthetic analogs of naturally occurring amino peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of "non-protein" α-amino acids include norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or para position of the phenyl moiety with one or two of the following: a ($C_1$–$C_4$) alkyl, a ($C_1$–$C_4$) alkoxy, halogen or nitro groups or substituted with a methylenedioxy group; β-2- and 3-thienylal-alanine, β-2- and 3-furanylalanine, β-2-, 3- and 4-pyridylalanine, β-(benzothienyl-2- and 3-yl) alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3- and 5-sulfonyl tyrosine, 3- and 5-carbonyl tyrosine, 3- and 5-phosphonyl tyrosine, 4-methylsulfonyl tyrosine, 4-methylphosphonyl tyrosine, 4-phenylacetic acid, 3,5-diiodotyrosine, 3- and 5-nitrotyrosine, ε-alkyl lysine, delta-alkyl ornithine, and the D-isomers of the naturally occurring amino acids.

The compounds referred to herein as tyrosine sulfate, $Tyr(OSO_3H)$ and O-sulfate ester of tyrosine are identical and have the structural formula:

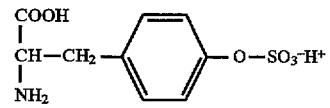

The compounds referred to herein as tyrosine sulfonate, $Tyr(SO_3H)$, 3-sulfonyl tyrosine and 5-sulfonyl tyrosine are identical and have the structural formula:

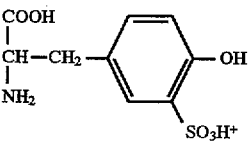

The term "patient" as used in this application refers to any mammal, especially humans.

The term "anionic amino acid" as used herein means a meta, para or ortho, mono- or di-substituted phenylalanine, cyclohexylalanine or tyrosine containing a carboxyl, phosphoryl or sulfonyl moiety, as well as S-alkylated cysteine, S-alkylated homocysteine, γ-carboxyglutamic acid, ε-alkyl lysine, delta-alkyl ornithine, glutamic acid, and aspartic acid. Examples of anionic amino acids are phosphothreonine, phosphoserine, phosphotyrosine, 3-, 4-, or 5-sulfotyrosine, 3-methyl phosphonyltyrosine and 3-methyl sulfonyltyrosine.

The terms "catalytic site", "active site" and "active site pocket" as used herein, each refer to any or all of the following sites in thrombin: the substrate binding or "$S_1$" site; the hydrophobic binding or "oily" site; and the site where cleavage of a substrate is actually carried out ("charge relay site").

The term "$N^{orn}$" as used herein, refers to the side chain nitrogen of ornithine. The term "$N^g$" refers to any of the side chain nitrogens of arginine. The term "$N^\alpha$" refers to the α-amino group of an amino acid. And the term "psi" as used in the specification and claims, refers to the replacement of an amide bond with the atoms designated in brackets, according to the nomenclature described in J. Rudinger, In *Drug Design*, Vol. II, E. J. Ariens, ed., Academic Press, New York, p. 319 (1971).

The term "backbone chain" as used herein, refers to the portion of a chemical structure that defines the smallest number of consecutive bonds that can be traced from one end of that chemical structure to the other. The atomic components that make up a backbone chain may comprise any atoms that are capable of forming bonds with at least two other atoms.

For example, each of the following chemical structures is characterized by a backbone chain of 7 atoms (the atoms which comprise the backbone chain are indicated in boldface):

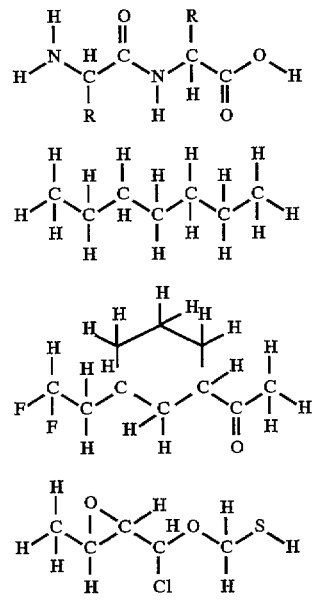

The term "calculated length" as used in this application, refers to a predicted measurement derived by summing up the bond lengths between the atoms which comprise the backbone chain. Bond lengths between any two given atoms are well known in the art [see, for example, *CRC Handbook of Chemistry and Physics*, 65th Edition, R. C. Weist, ed., CRC Press, Inc., Boca Raton, Fla., pp. F-166–70 (1984)].

The present invention relates to molecules which bind to and inhibit thrombin. These molecules are characterized by three domains: a catalytic site-directed moiety ("CSDM"), a linker region, and an anion binding exosite associating moiety ("ABEAM").

According to the present invention, the first domain, CSDM, binds to the catalytic site of thrombin located at or near about Ser-195 and inhibits or retards the amidolytic or estereolytic activity of thrombin. Preferably, CSDMs of the present invention are selected from one of three general groups: those which bind reversibly to thrombin and are slowly cleaved; those which bind reversibly to thrombin and cannot be cleaved; and those which bind irreversibly to thrombin. Reversible inhibitors bind to the active site of thrombin through non-covalent interactions, such as ionic bonds, hydrophobic interactions or hydrogen bonding. Irreversible CSDMs form covalent bonds with thrombin.

According to a preferred embodiment, the CSDM which binds reversibly to thrombin and is slowly cleaved has the formula:

$$X\text{-}A_1\text{-}A_2\text{-}A_3\text{-}Y,$$

wherein X is hydrogen or is characterized by a backbone chain consisting of from 1 to 35 atoms; $A_1$ is Arg, Lys or Orn; $A_2$ is a non-amide bond; $A_3$ is characterized by a backbone chain consisting of from 1 to 9 atoms; and Y is a bond.

The non-amide bond component according to this embodiment may be formed by chemically modifying an amide bond. This may be achieved by methods well known in the art [M. Szelke et al., "Potent New Inhibitors of Human Renin", *Nature*, 299, pp. 555–57 (1982); D. H. Coy et al., "Facile Solid Phase Preparation of Proteins Containing the $CH_2$—NH Peptide Bond Isostere and Application to the Synthesis of Somatostatin (SRIF) Octapeptide Analogues", *Peptides 1986*, D. Theodoropoulos, Ed., Walter DeGruyter & Co., Berlin, pp. 143–46 (1987)]. When a non-amide bond is formed in this manner, it is preferable that the chemical modification be performed prior to the addition of the dipeptide containing this bond to the other components of CSDM or to the rest of the thrombin inhibitor molecule. In this manner, the dipeptide $A_1$-$A_2$-$A_3$ is added en bloc, in a single synthesis step, to the rest of the molecule.

According to a more preferred embodiment, $A_1$ is Arg and $A_3$ is Pro, D-Pro or Sar. In this embodiment $A_2$ is a naturally occurring imide bond, which is slowly cleaved by thrombin. This avoids having the necessity of pre-forming the non-amide bond and allows $A_1$ and $A_3$ to be added to the rest of the molecule sequentially rather than en bloc.

As set forth above, CSDMs according to this invention may bind irreversibly to thrombin. Examples of irreversible CSDMs include, but are not limited to, general serine proteinase inhibitors, such as phenylmethylsulfonylfluoride (PMSF), diisopropylfluorophosphate (DFP), tosylprolyl-chloromethylketone (TPCK) and tosyllysylchloromethylketone (TLCK); heterocyclic protease inhibitors, such as isocoumarins; thrombin-specific inhibitors, such as D-Phe-Pro-Arg-CHCl$_2$ (PPACK); and transition state analogues, such as difluoroketomethylene.

According to another preferred embodiment of the present invention, non-cleavable, reversible CSDMs consist of the formula:

$$X\text{-}C_1\text{-}C_2\text{-}A_3\text{-}Y,$$

wherein $C_1$ is a derivative of Arg, Lys or Orn characterized by a reduced carboxylate moiety or a carboxylate moiety that is displaced from the α-carbon by a chemical structure characterized by a backbone chain of from 1 to 10 atoms; $C_2$ is a non-cleavable bond; and X, Y and $A_3$ are as defined previously. Examples of $C_1$ components are β-homoarginine; arginine containing a reduced carboxylate moiety, such as Arg[psiCH$_2$NH]; β-homolysine and β-homoornithine.

Other non-cleavable, reversible CSDMs that may be employed in the thrombin inhibitors of this invention are benzamidine, DAPA, NAPAP and argatroban (argipidine).

For those thrombin inhibitors of this invention which have CSDM regions characterized by an $A_2$ or $C_2$ bond, the term "$P_1$-$P_1'$" sequence as used herein, refers to the two chemical structures joined by said bond.

The X component of CSDM, which does not participate in actually binding to the catalytic site, can be of unlimited length and variable make-up. However, for practical purposes and reduced cost of synthesis, X is preferably characterized by a backbone chain consisting of from 1 to 35 atoms and does not exceed a calculated length of 36 Å. It is preferred that X be a peptide, most preferably, D-Phe-Pro. This most preferable embodiment allows the X component to fit into a groove in thrombin that is adjacent to the active site [S. Bajusz et al., "Inhibition of Thrombin and Trypsin by Tripeptide Aldehydes", *Int. J. Peptide Protein Res.*, 12, pp. 217–21 (1978); C. Kettner et al., "D-Phe-Pro-Arg-$CH_2Cl$—A Selective Affinity Label for Thrombin", *Thromb. Res.*, 14, pp. 969–73 (1979)]. This allows the CSDM component and therefore the molecules of the present invention, to bind to thrombin with an advantageously high degree of affinity and optimal specificity.

According to the present invention, the second component of the thrombin inhibitors of this invention is a linker region. Because the role of this portion of the molecule is to provide a bridge between the CSDM and the ABEAM, it is the length of the linker, rather than its structure, that is of prime importance. The calculated length of the backbone chain which characterizes the linker must be at least about 18 Å—the distance between the catalytic site and the anion binding exosite of thrombin—and less than about 42 Å.

The backbone chain of the linker may comprise any atoms which are capable of bonding to at least two other atoms. Preferably, the backbone chain consists of any chemically feasible combination of atoms selected from oxygen, carbon, nitrogen and sulfur. Those of skill in the art are aware of what combination of the above backbone chain atoms falls within the required length based on known distances between various bonds [see, for example, R. T. Morrison and R. N. Boyd, *Organic Chemistry, 3rd Edition*, Allyn and Bacon, Inc., Boston, Mass. (1977)]. According to a preferred embodiment, the linker is a peptide which comprises the amino acid sequence Gly-Gly-Gly-Asn-Gly-Asp-Phe. Preferably, the amino acid bound to the ABEAM component is Phe.

The third domain of the thrombin inhibitors of this invention is the ABEAM which binds to the anion binding exosite of thrombin. Preferably the ABEAM has the formula:

wherein W is a bond; $B_1$ is an anionic amino acid; $B_2$ is any amino acid; $B_3$ is Ile, Val, Leu, Nle or Phe; $B_4$ is Pro, Hyp, 3,4-dehydroPro, thiazolidine-4-carboxylate, Sar, any N-methyl amino acid or D-Ala; $B_5$ is an anionic amino acid; $B_6$ is an anionic amino acid; $B_7$ is a lipophilic amino acid selected from the group consisting of Tyr, Trp, Phe, Leu, Nle, Ile, Val, Cha, Pro, or a dipeptide consisting of one of these lipophilic amino acids and any amino acid; $B_8$ is a bond or a peptide containing from one to five residues of any amino acid; and Z is a carboxy terminal residue selected from OH, $C_1$–$C_6$ alkoxy, amino, mono- or di-($C_1$–$C_4$) alkyl substituted amino or benzylamino.

Peptides which are homologous to the carboxy terminal portion of hirudin have been shown to bind to the anion binding exosite on thrombin [copending U.S. patent application 314,756 and J. M. Maraganore et al., "Anticoagulant Activity of Synthetic Hirudin Peptides", *J. Biol. Chem.*, 264, pp. 8692–98 (1989); both of which are herein incorporated by reference].

According to a preferred embodiment of this invention, ABEAM is homologous to amino acids 56–64 of hirudin, i.e., $B_1$ is Glu; $B_2$ is Glu; $B_3$ is Ile; $B_4$ is Pro; $B_5$ is Glu; $B_6$ is Glu; $B_7$ is Tyr-Leu, Tyr($SO_3H$)-Leu or Tyr($OSO_3H$)-Leu, or (3-,5-diiodoTyr)-Leu; $B_8$ is a bond; and Z is OH. It should be noted that native hirudin contains Tyr($OSO_3H$) at position 63. However, carboxy terminal hirudin peptides which contain Tyr($SO_3H$) have identical anticoagulant activity as those which contain the native Tyr($OSO_3H$) [see copending U.S. patent application 314,756].

Other ABEAM components within the scope of this invention may comprise those portions of any molecule known to bind to the anion binding site of thrombin. These include amino acids 1675–1686 of Factor V, amino acids 272–285 of platelet glycoproten Ib, amino acids 415–428 of thrombomodulin, amino acids 245–259 of prothrombin Fragment 2 and amino acids 30 to 44 of fibrinogen Aα chain. In addition, the ABEAM component may be selected from any of the hirudin peptide analogues described by J. L. Krstenansky et al., "Development of MDL-28,050, A Small Stable Antithrombin Agent Based On A Functional Domain of the Leech Protein, Hirudin", *Thromb. Haemostas.*, 63, pp. 208–14 (1990).

The preferred thrombin inhibitors of this invention are termed Hirulogs, and are described in the subsequent examples. The most preferred Hirulogs are Hirulog-8, Hirulog-12, Hirulog-18a, Hirulog-18b and Hirulog-33. Hirulog-8, -12 and -33 are reversible thrombin inhibitors that are slowly cleaved. Hirulog-18a and -18b are reversible inhibitors which are not cleaved.

The thrombin inhibitors of the present invention may be synthesized by various techniques which are well known in the art. These include enzymatic cleavage of natural or recombinant hirudin, recombinant DNA techniques, solid-phase peptide synthesis, solution-phase peptide synthesis, organic chemical synthesis techniques, or a combination of these techniques. The choice of synthesis technique will, of course, depend upon the composition of the particular inhibitor. In a preferred embodiment of this invention, the thrombin inhibitor is entirely peptidic and is synthesized by solid-phase peptide synthesis techniques, solution-phase peptide synthesis techniques or a combination thereof which constitute the most cost-efficient procedures for producing commercial quantities of these molecules.

When "non-protein" amino acids are contained in the thrombin inhibitor molecule, they may be either added directly to the growing chain during peptide synthesis or prepared by chemical modification of the complete synthesized peptide, depending on the nature of the desired "non-protein" amino acid. Those of skill in the chemical synthesis art are well aware of which "non-protein" amino acids may be added directly and which must be synthesized by chemically modifying the complete peptide chain following peptide synthesis.

The synthesis of those thrombin inhibitors of this invention which contain both non-amino acid and peptidic portions is preferably achieved by a mixed heterologous/solid phase technique. This technique involves the solid-phase synthesis of all or most of the peptide portion of the molecule, followed by the addition of the non-amino acid components which are synthesized by solution phase techniques. The non-amino acid may be coupled to the peptidic portion via solid-phase or solution-phase methods. Similarly, any remaining peptidic portions may also be added via solid-phase or solution phase methods.

The molecules of the present invention display potent anticoagulant activity. This activity may be assayed in vitro using any conventional technique. Preferably, an assay for anticoagulant activity involves direct determination of the thrombin-inhibitory activity of the molecule. Such techniques measure the inhibition of thrombin-catalyzed cleavage of colorimetric substrates or, more preferably, the increase in thrombin times or increase in activated partial thromboplastin times of human plasma. The latter assay measures factors in the "intrinsic" pathway of coagulation. Alternatively, the assay employed may use purified thrombin and fibrinogen to measure the inhibition of release of fibrinopeptides A or B by radioimmunoassay or ELISA.

The antiplatelet activity of the molecules of this invention may also be measured by any of a number of conventional platelet assays. Preferably, the assay will measure a change in the degree of aggregation of platelets or a change in the release of a platelet secretory component in the presence of thrombin. The former may be measured in an aggregometer. The latter may be measured using RIA or ELISA techniques specific for the secreted component.

The molecules of the present invention are useful in compositions, combinations and methods for the treatment and prophylaxis of various diseases attributed to thrombin-mediated and thrombin-associated functions and processes. These include myocardial infarction, stroke, pulmonary embolism, deep vein thrombosis, peripheral arterial occlusion, restenosis following arterial injury or invasive cardiological procedures, acute or chronic atherosclerosis, edema and inflammation, various cell regulatory processes (e.g. secretion, shape changes, proliferation), cancer and metastasis, and neurodegenerative diseases.

The thrombin inhibitors of the present invention may be formulated using conventional methods to prepare pharmaceutically useful compositions, such as the addition of a pharmaceutically acceptable carrier. These compositions and the methods employing them may be used for treating or preventing thrombotic diseases in a patient.

According to an alternate embodiment of the present invention, the thrombin inhibitors may be employed in combinations, compositions, and methods for treating thrombotic disease, and for decreasing the dosage of a thrombolytic agent required to establish reperfusion or prevent reocclusion in a patient. Additionally, the thrombin inhibitors of this invention may be used in combinations, compositions, and methods for decreasing reperfusion time or increasing reocclusion time in a patient treated with a thrombolytic agent. These combinations and compositions comprise a pharmaceutically effective amount of a thrombin inhibitor of the present invention and a pharmaceutically effective amount of a thrombolytic agent.

In these combinations and compositions, the thrombin inhibitor and the thrombolytic agent work in a complementary fashion to dissolve blood clots, resulting in decreased reperfusion times and increased reocclusion times in patients treated with them. Specifically, the thrombolytic agent dissolves the clot, while the thrombin inhibitor prevents newly exposed, clot-entrapped or clot-bound thrombin from regenerating the clot. The use of the thrombin inhibitor in the combinations and compositions of this invention advantageously allows the administration of a thrombolytic reagent in dosages previously considered too low to result in thrombolytic effects if given alone. This avoids some of the undesirable side effects associated with the use of thrombolytic agents, such as bleeding complications.

Thrombolytic agents which may be employed in the combinations and compositions of the present invention are those known in the art. Such agents include, but are not limited to, tissue plasminogen activator purified from natural sources, recombinant tissue plasminogen activator, streptokinase, urokinase, prourokinase, anisolated streptokinase plasminogen activator complex (ASPAC), animal salivary gland plasminogen activators and known, biologically active derivatives of any of the above.

The term "combination" as used herein, includes a single dosage form containing at least one thrombin inhibitor of this invention and at least one thrombolytic agent; a multiple dosage form, wherein the thrombin inhibitor and the thrombolytic agent are administered separately, but concurrently; or a multiple dosage form wherein the two components are administered separately, but sequentially. In sequential administration, the thrombin inhibitor may be given to the patient during the time period ranging from about 5 hours prior to about 5 hours after administration of the thrombolytic agent. Preferably, the thrombin inhibitor is administered to the patient during the period ranging from 2 hours prior to 2 hours following administration of the thrombolytic agent.

Alternatively, the thrombin inhibitor and the thrombolytic agent may be in the form of a single, conjugated molecule. Conjugation of the two components may be achieved by standard cross-linking techniques well known in the art. The single molecule may also take the form of a recombinant fusion protein, if both the thrombin inhibitor and the thrombolytic agent are peptidic.

Various dosage forms may be employed to administer the compositions and combinations of this invention. These include, but are not limited to, parenteral administration, oral administration and topical application. The compositions and combinations of this invention may be administered to the patient in any pharmaceutically acceptable dosage form, including those which may be administered to a patient intravenously as bolus or by continued infusion, intramuscularly—including paravertebrally and periarticularly—subcutaneously, intracutaneously, intra-articularly, intrasynovially, intrathecally, intra-lesionally, periostally or by oral, nasal, or topical routes. Such compositions and combinations are preferably adapted for topical, nasal, oral and parenteral administration, but, most preferably, are formulated for parenteral administration.

Parenteral compositions are most preferably administered intravenously either in a bolus form or as a constant infusion. If the thrombin inhibitor is being used as an antiplatelet compound, constant infusion is preferred. If the thrombin inhibitor is being used as an anticoagulant, a subcutaneous or intravenous bolus injection is preferred. For parenteral administration, fluid unit dose forms are prepared which contain a thrombin inhibitor of the present invention and a sterile vehicle. The thrombin inhibitor may be either suspended or dissolved, depending on the nature of the vehicle and the nature of the particular thrombin inhibitor. Parenteral compositions are normally prepared by dissolving the thrombin inhibitor in a vehicle, optionally together with other components, and filter sterilizing before filling into a suitable vial or ampule and sealing. Preferably, adjuvants such as a local anesthetic, preservatives and buffering agents are also dissolved in the vehicle. The composition may then be frozen and lyophilized to enhance stability.

Parenteral suspensions are prepared in substantially the same manner, except that the active component is suspended rather than dissolved in the vehicle. Sterilization of the compositions is preferably achieved by exposure to ethylene oxide before suspension in the sterile vehicle. Advantageously, a surfactant or wetting agent is included in the composition to facilitate uniform distribution of its components.

Tablets and capsules for oral administration may contain conventional excipients, such as binding agents, fillers, diluents, tableting agents, lubricants, disintegrants, and wetting agents. The tablet may be coated according to methods well known in the art. Suitable fillers which may be employed include cellulose, mannitol, lactose and other similar agents. Suitable disintegrants include, but are not limited to, starch, polyvinylpyrrolidone and starch derivatives, such as sodium starch glycolate. Suitable lubricants include, for example, magnesium stearate. Suitable wetting agents include sodium lauryl sulfate.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives. These include suspending agents; such as sorbitol, syrup, methyl cellulose, gelatin, hydroxyethylcellulose, carboxymethylcellulose, aluminum stearate gel or hydrogenated edible fats; emulsifying agents which include lecithin, sorbitan monooleate, polyethylene glycols, or acacia; non-aqueous vehicles, such as almond oil, fractionated coconut oil, and oily esters; and preservatives, such as methyl or propyl p-hydroxybenzoate or sorbic acid.

Compositions formulated for topical administration may, for example, be in aqueous jelly, oily suspension or emulsified ointment form.

The dosage and dose rate of the thrombin inhibitor will depend on a variety of factors, such as the size of the patient, the specific pharmaceutical composition used, the object of the treatment, i.e., therapy or prophylaxis, the nature of the thrombotic disease to be treated, and the judgment of the treating physician.

According to the present invention, a preferred pharmaceutically effective daily dose of the thrombin inhibitor of this invention is between about 1 µg/kg body weight of the patient to be treated ("body weight") and about 5 mg/kg body weight. In combinations containing a thrombolytic agent, a pharmaceutically effective daily dose of the thrombolytic is between about 10% and 80% of the conventional dosage range. The "conventional dosage range" of a thrombolytic agent is the daily dosage used when that agent is employed in a monotherapy. [Physician's Desk Reference 1989, 43rd Edition, Edward R. Barnhart, publisher]. That conventional dosage range will, of course, vary depending on the thrombolytic agent employed. Examples of conventional dosage ranges are as follows: urokinase—500,000 to 6,250,000 units/patient; streptokinase—140,000 to 2,500,000 units/patient; tPA—0.5 to 5.0 mg/kg body weight; ASPAC—0.1 to 10 units/kg body weight.

Most preferably, the therapeutic and prophylactic compositions of the present invention comprise a dosage of between about 10 µg/kg body weight and about 500 µg/kg body weight of the thrombin inhibitor. Most preferred combinations comprise the same amount of the thrombin inhibitor and between about 10% and about 70% of the conventional dosage range of a thrombolytic agent. It should also be understood that a daily pharmaceutically effective dose of either the thrombin inhibitors of this invention or the thrombolytic agent present in combinations of the invention, may be less than or greater than the specific ranges cited above.

Once improvement in the patient's condition has occurred, a maintenance dose of a combination or composition of this invention is administered, if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment upon any recurrence of disease symptoms.

According to an alternate embodiment of this invention, thrombin inhibitors may be used in compositions and methods for coating the surfaces of invasive devices, resulting in a lower risk of clot formation or platelet activation in patients receiving such devices. Surfaces that may be coated with the compositions of this invention include, for example, prostheses, artificial valves, vascular grafts, stents and catheters. Methods and compositions for coating these devices are known to those of skill in the art. These include chemical cross-linking or physical adsorption of the thrombin inhibitor-containing compositions to the surfaces of the devices.

According to a further embodiment of the present invention, thrombin inhibitors may be used for ex vivo thrombus imaging in a patient. In this embodiment, the thrombin inhibitor is labelled with a radioisotope. The choice of radioisotope is based upon a number of well-known factors, for example, toxicity, biological half-life and detectability. Preferred radioisotopes include, but are not limited to, $^{125}I$, $^{123}I$ and $^{111}In$. Techniques for labelling the thrombin inhibitor are well known in the art. Most preferably, the radioisotope is $^{123}I$ and the labelling is achieved using $^{123}I$-Bolton-Hunter Reagent. The labelled thrombin inhibitor is administered to a patient and allowed to bind to the thrombin contained in a clot. The clot is then observed by utilizing well-known detecting means, such as a camera capable of detecting radioactivity coupled to a computer imaging system. This technique also yields images of platelet-bound thrombin and meizothrombin.

This invention also relates to compositions containing the thrombin inhibitors of this invention and methods for using such compositions in the treatment of tumor metastases. The efficacy of the thrombin inhibitors of this invention for the treatment of tumor metastases is manifested by the inhibition of metastatic growth. This is based upon the presence of a procoagulant enzyme in certain cancer cells. This enzyme activates the conversion of Factor X to Factor Xa in the coagulation cascade, resulting in fibrin deposition which, in turn, serves as a substrate for tumor growth. By inhibiting fibrin deposition through the inhibition of thrombin, the molecules of the present invention serve as effective anti-metastatic tumor agents. Examples of metastatic tumors which may be treated by the thrombin inhibitors of this invention include, but are not limited to, carcinoma of the brain, carcinoma of the liver, carcinoma of the lung, osteo-carcinoma and neoplastic plasma cell carcinoma.

The invention also relates to methods and compositions employing the above-described thrombin inhibitors to inhibit thrombin-induced endothelial cell activation. This inhibition includes the repression of platelet activation factor (PAF) synthesis by endothelial cells. These compositions and methods have important applications in the treatment of diseases characterized by thrombin-induced inflammation and edema, which is thought to be mediated be PAF. Such diseases include, but are not limited to, adult respiratory distress syndrome, septic shock, septicemia and reperfusion damage.

Early stages of septic shock include discrete, acute inflammatory and coagulopathic responses. It has previously been shown that injection of baboons with a lethal dose of live E. coli leads to marked declines in neutrophil count, blood pressure and hematocrit. Changes in blood pressure and hematocrit are due in part to the generation of a disseminated intravascular coagulopathy (DIC) and have been shown to parallel consumption of fibrinogen [F. B. Taylor et al., "Protein C Prevents the Coagulopathic and Lethal Effects of *Escherichia coli* infusion in the Baboon", *J. Clin. Invest.*, 79, pp. 918–25 (1987)]. Neutropenia is due to the severe inflammatory response caused by septic shock which results in marked increases in tumor necrosis factor levels. The thrombin inhibitors of this invention may be utilized in compositions and methods for treating or preventing DIC in septicemia and other diseases.

This invention also relates to the use of the above-described thrombin inhibitors, or compositions comprising them, as anticoagulants for extracorporeal blood. As used herein, the term "extracorporeal blood" includes blood removed in line from a patient, subjected to extracorporeal treatment, and then returned to the patient in such processes as dialysis procedures, blood filtration, or blood bypass during surgery. The term also includes blood products which are stored extracorporeally for eventual administration to a patient and blood collected from a patient to be used for various assays. Such products include whole blood, plasma, or any blood fraction in which inhibition of coagulation is desired.

The amount or concentration of thrombin inhibitor in these types of compositions is based on the volume of blood to be treated or, more preferably, its thrombin content. Preferably, an effective amount of a thrombin inhibitor of this invention for preventing coagulation in extracorporeal blood is from about 1 µg/60 ml of extracorporeal blood to about 5 mg/60 ml of extracorporeal blood.

The thrombin inhibitors of this invention may also be used to inhibit clot-bound thrombin, which is believed to contribute to clot accretion. This is particularly important because commonly used anti-thrombin agents, such as heparin and low molecular weight heparin, are ineffective against clot-bound thrombin.

Finally, the thrombin inhibitors of this invention may be employed in compositions and methods for treating neurodegenerative diseases. Thrombin is known to cause neurite retraction, a process suggestive of the rounding in shape changes of brain cells and implicated in neurodegenerative diseases, such as Alzheimer's disease and Parkinson's disease.

In order that the invention described herein may be more fully understood, the following examples are set forth. It should be understood that these examples are for illustrative purposes only and are not to be construed as limiting this invention in any manner.

EXAMPLE 1

Synthesis Of Sulfo-$Tyr_{63}$hirudin$_{54-64}$

Sulfo-Tyr63hirudin$_{54-64}$ has the amino acid formula: H-Gly-Asp-Phe-Glu-Glu-Ile-Pro-Glu-Glu-Tyr($OSO_3$)-Leu-OH. We prepared this peptide by solid-phase peptide synthesis employing an Applied Biosystems 430 A Peptide Synthesizer (Applied Biosystems, Foster City, Calif.).

Specifically, we reacted 0.259 meq of BOC-O-Leu resin (1% DVB resin) sequentially with 2 mmoles of protected amino acids. Following 10 cycles of synthesis, we deprotected the peptide and uncoupled it from the DVB resin by treatment with anhydrous HF:p-cresol:ethyl methyl sulfate (10:1:1, v/v/v). The peptide was further purified on a Vydac $C_{18}$ HPLC reverse phase column (22 mm×25 cm) which had previously been equilibrated in 0.1% TFA in water. Prior to applying the peptide to the column, we dissolved it in 2.0 ml of 0.1% TFA in water. If necessary, an additional 1 ml of 6M guanidinium chloride was added to the sample to increase solubility. After we applied the sample, the column was developed with a linear gradient of increasing acetonitrile (0–80%) in 0.1% TFA over 45 minutes at a flow rate of 4.0 ml/min. The effluent stream was monitored at 229 nm and fractions were collected manually.

We sulfated the resulting purified peptide at the single tyrosine residue using standard methodology [T. Nakahara et al., "Preparation of Tyrosine-O-[$^{35}$S]Sulfated Cholecystokinin Octapeptide From A Non-Sulfated Precursor Peptide", *Anal. Biochem.*, 154, pp. 194–99 (1986)]. Sulfo-$Tyr_{63}$hirudin$_{54-64}$ was then purified away from other peptides and reaction components by reverse-phase HPLC employing a Vydac $C_{18}$ column (4.6×25 cm) and an Applied Biosystems liquid chromatographic system. The column was equilibrated in a 0.1% TFA/water solvent and developed with a linear gradient of increasing acetonitrile concentration from 0 to 35% over 90 minutes at a flow rate of 0.8 ml/min with a 0.085% TFA-containing solvent. Fractions were assayed for absorbance at 214 nm.

EXAMPLE 2

Crosslinking Of Human Thrombin With Sulfo-$Tyr_{63}$-Dinitrofluorobenzyl-hirudin$_{54-64}$ We prepared Sulfo-$Tyr_{63}$-dinitrofluorobenzyl-hirudin$_{54-64}$ (Sulfo-$Tyr_{63}$-DNFB-hirudin$_{54-64}$) by reacting Sulfo-$Tyr_{63}$hirudin$_{54-64}$ (2.0 mg; prepared as in Example 1) with a stoichiometric quantity of difluorodinitrobenzene (Pierce Chemical Co., Rockford, Ill.) in dimethylftemamide (DMF) for 18 hours at room temperature. We then subjected the sample to analytical HPLC separation employing an Applied Biosystems 150 A Liquid Chromatographic System and a Brownlee RP-300 $C_8$ column (0.46×10 cm) to determine the extent of derivatization. The column was equilibrated in 0.1% TFA in water (solvent A) and developed with a 0–50% linear gradient of 0.085% TFA/70% acetonitrile (solvent B) over 45 min and then a 50–100% linear gradient of solvent B over 15 min. We used a constant flow rate of 1.0 ml/minute.

The effluent stream was monitored at 214 nm and 310 nm for absorbance. Peptide derivatized with the difluorodinitrobenzene reagent absorbs at 310 nm. We found that the above-described reaction produced Sulfo-$Tyr_{63}$-DNFB-hirudin$_{54-64}$ at 15–30% yield. Following synthesis, Sulfo-$Tyr_{63}$-DNFB-hirudin$_{54-64}$ was stored in the same dimethylformamide solvent at −20° C. for up to 1 month.

We reacted a 10-fold molar excess of Sulfo-$Tyr_{63}$-DNFB-hirudin$_{54-64}$ with human α-thrombin (12.5 mg) for 18 hr at room temperature in a phosphate-buffered saline. We determined the extent of cross-linking by analyzing the reaction mixture on an SDS-polyacrylamide gel. SDS-PAGE showed a decrease in the relative mobility of the α-thrombin band reflective of an increase in molecular weight of 1000–2000 daltons (Da). This shift is consistent with cross-linking of thrombin with Sulfo-Tyr63-DNFB-hirudin$_{54-64}$ at a single site.

We confirmed that formation of a covalent complex between Sulfo-$Tyr_{63}$-DNFB-hirudin$_{54-64}$ and human thrombin is specific by using [$^{35}$S]-Sulfo-$Tyr_{63}$-DNFB-hirudin$_{54-64}$. [$^{35}$S]-Sulfo-$Tyr_{63}$-DNFB-hirudin$_{54-64}$ was prepared essentially as described above using $H_2$[$^{35}$S]$O_4$ instead of $H_2SO_4$ in the Nakahara sulfation procedure [see also, copending U.S. patent application Ser. Nos. 164,178, 251, 150, 280,618, and 314,756, and J. M. Maraganore et al., "Anticoagulant Activity of Synthetic Hirudin Peptides", *J.*

*Biol. Chem.*, 264, pp. 8692–98 (1989) all of which are herein incorporated by reference].

We reacted [$^{35}$S]-Sulfo-Tyr$_{63}$-DNFB-hirudin$_{54-64}$ with human α-thrombin, either in the presence or absence of a 5- or 20-fold molar excess (over the concentration of thrombin) of Sulfo-Tyr$_{63}$-N-acetyl-hirudin$_{54-64}$ (prepared as in Example 1 with the addition of N-acetyl asparagine as a final step in peptide synthesis). Following incubation at room temperature for 18 hrs, we subjected the mixture to SDS-PAGE and autoradiography. The results (FIG. 1) showed that [$^{35}$S]-labeled peptide was incorporated into the band which represents thrombin and that the presence of cold, unlabeled hirudin peptide attenuated the magnitude of covalent complex formation to <10%. Thus, reaction of Sulfo-Tyr63-DNFB-hirudin$_{54-64}$ with thrombin results in the 1:1 stoichiometric binding of the hirudin peptide at a specific binding site.

In order to identify the site on thrombin where Sulfo-Tyr$_{63}$-DNFB-hirudin$_{54-64}$ binds, thrombin/Sulfo-Tyr$_{63}$-dinitrobenzyl(DNB)-hirudin$_{54-64}$ complex (1.0 mg) was applied to a Sephadex G-50 column (1.5×45 cm) which was equilibrated and developed with 7M urea, 20 mM Tris, pH 7.5. This chromatography removed any unreacted Sulfo-Tyr$_{63}$-DNFB-hirudin$_{54-64}$. A peak containing thrombin/Sulfo-Tyr$_{63}$-DNB-hirudin$_{54-64}$ was isolated in the void volume fractions, pooled and reduced by the addition of 10 μl of β-mercaptoethanol.

Following reduction, we S-carboxymethylated the complex using iodoacetic acid as previously described [J. M. Maraganore et al., "A New Class of Phospholipases A$_2$ with Lysine in Place of Aspartate-49", *J. Biol. Chem*, 259, pp. 13839–43 (1984)]. The reduced, S-alkylated protein was then dialyzed extensively against 3% acetic acid at room temperature. Following dialysis, we digested the complex with pepsin (2% w/v) for 4 hr at 37° C. Peptic fragments of reduced, S-carboxymethylated thrombin/Sulfo-Tyr$_{63}$-DNB-hirudin$_{54-64}$ were purified by reverse-phase HPLC using an Aquapore RP-300 C$_8$ column (0.46×10 cm). The column was equilibrated in 0.1% TFA in water and developed with a gradient of increasing 0.085% TFA/70% acetonitrile (0–60%) over 80 minutes at a flow rate of 1.0 ml/min. The effluent stream was monitored for absorbance at both 214 and 310 nm. Fractions of 1.0 ml were collected automatically. HPLC separation of peptic fragments allowed resolution of a single major peak of both 214 and 310 nm-absorbing material. Because of its far UV absorbance, this fragment contained the bound Sulfo-Tyr$_{63}$-DNFB-hirudin$_{54-64}$.

We then subjected the fragment to automated Edman degradation with an Applied Biosystems 470A gas-phase sequencer equipped with a 900A data system. Phenylthiohydantoin (PTH) amino acids were analyzed on-line using an Applied Biosystems 120A PTH analyzer and a PTH-C$_{18}$ column (2.1×220 mm). Shown below is a table of repetitive yields from the sequence analysis:

| Cycle | Amino Acid | pmoles |
| --- | --- | --- |
| 1 | Lys | 858.5 |
| 2 | Glu | 629.2 |
| 3 | Thr | 357.6 |
| 4 | Trp | 276.3 |
| 5 | Thr | 289.0 |
| 6 | Ala | 474.4 |
| 7 | Asn | 369.0 |
| 8 | Val | 490.7 |

-continued

| Cycle | Amino Acid | pmoles |
| --- | --- | --- |
| 9 | Gly | 296.1 |
| 10 | (x) | (—) |
| 11 | Gly | 267.2 |
| 12 | Gln | 208.8 |
| 13 | Pro | 103.5 |
| 14 | Ser | 21.6 |
| 15 | Val | 23.3 |

The peptide sequence was found to correspond to residues 144–154 of human α-thrombin [J. W. Fenton, II., "Thrombin Active Site Regions" *Semin. Thromb. Hemostasis*, 12, pp. 200–08 (1986)]. Peptic cleavages occurred at a Leu-Lys and Val-Leu bond, consistent with the specificity of this enzyme.

In the course of sequence analysis, the amino acid corresponding to Lys-149 (cycle 10) could not be identified or quantitated. This probably resulted from derivatization of the ε-NH$_2$ group of this amino acid with the dinitrofluorobenzyl moiety of Sulfo-Tyr$_{63}$-DNFB-hirudin$_{54-64}$. Thus, Lys-149 is the major site where Sulfo-Tyr$_{63}$-DNFB-hirudin$_{54-64}$ reacts with α-thrombin.

EXAMPLE 3

Design Of A Thrombin Inhibitor Capable Of Blocking The Catalytic Site And Binding To The Anion Binding Exosite Carboxy terminal hirudin peptides effectively block thrombin-catalyzed fibrinogen hydrolysis, but not chromogenic substrate hydrolysis [J. M. Maraganore et al., *J. Biol. Chem.*, 264, pp. 8692–98 (1989)]. In addition, hirudin peptides do not neutralize thrombin-catalyzed activation of Factors V and VIII [J. W. Fenton, II, et al., "Hirudin Inhibition by Thrombin", *Angio. Archiv. Biol.*, 18, p. 27 (1989)].

Hirudin peptides, such as Sulfo-Tyr$_{63}$-N-acetyl-hirudin$_{54-64}$, exhibit potent inhibitory effects toward thrombin-induced platelet activation in vitro [J. A. Jakubowsky and J. M. Maraganore, "Inhibition of Thrombin-Induced Platelet Activities By A Synthetic 12 Amino Acid Residue Sulfated Peptide (Hirugen)", *Blood*, p. 1213 (1989)]. Nevertheless, a thrombin inhibitor capable of blocking the active site may be required for inhibition of platelet thrombosis in vivo, if activation of Factors V and VIII are rate-limiting steps. This conclusion is warranted from results obtained with the irreversible thrombin inhibitor (D-Phe)-Pro-Arg-CH$_2$Cl [S. R. Hanson and L. A. Harker, "Interruption of Acute Platelet-Dependent Thrombosis by the Synthetic Antithrombin D-phenylalanyl-L-Prolyl-L-Arginyl Chloromethyl Ketone", *Proc. Natl. Acad. Sci. USA*, 85, pp. 3184–88 (1988)] and other reversible thrombin inhibitors [J. F. Eidt et al., "Thrombin is an Important Mediator of Platelet Aggregation in Stenosed Canine Coronary Arteries with Endothelial Injury", *J. Clin. Invest.*, 84, pp. 18–27 (1989)].

Figure 2:
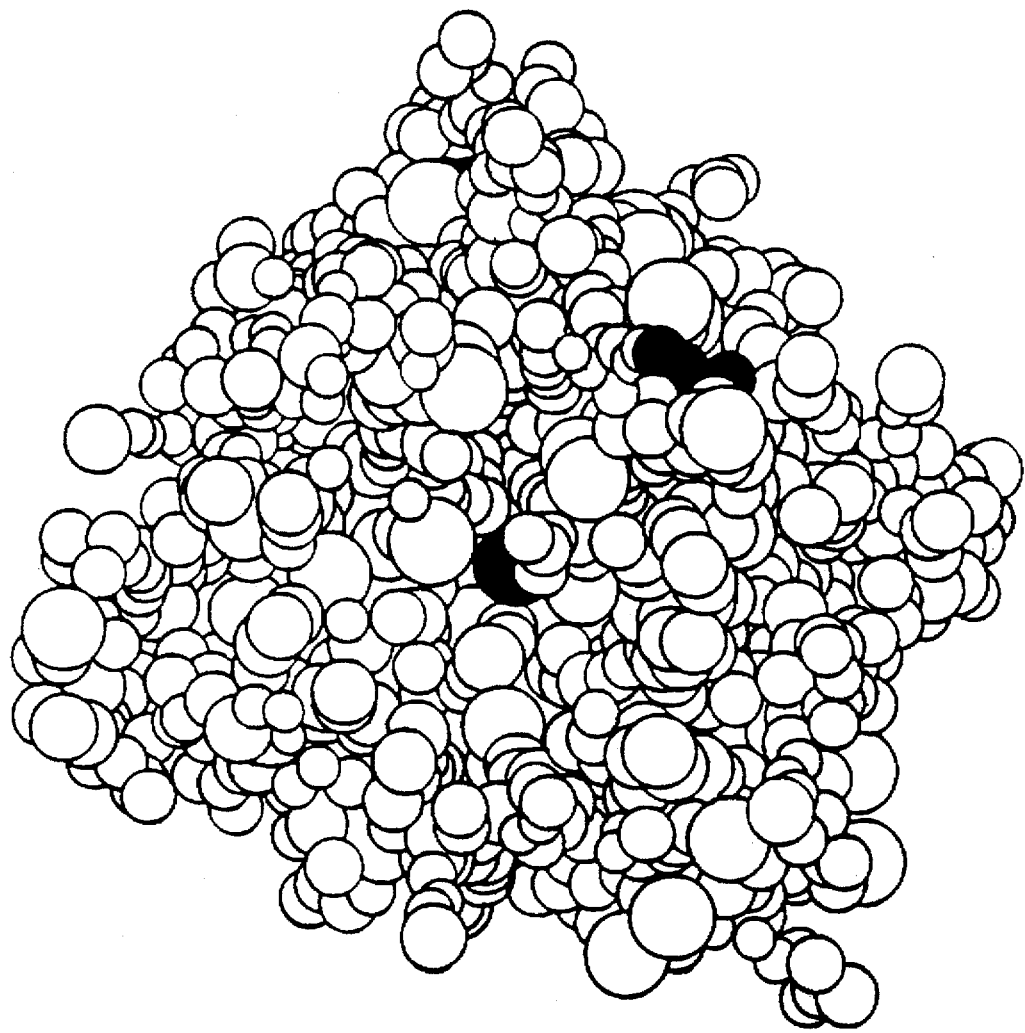
FIG. 2 depicts a three-dimensional model of human α-thrombin.

Using the above knowledge that the NH$_2$-terminus of hirudin peptides is proximal to Lys-149, we employed a three-dimensional model of thrombin (FIG. 2) [B. Furie, et al., "Computer-Generated Models of Blood Coagulation Factor Xa, Factor IXa, and Thrombin Based Upon Structural Homology with Other Serine Proteases", *J. Biol. Chem.*, 257, pp. 3875–82 (1982)] to design an agent which: 1) binds to the anion binding exosite of thrombin; and, 2) is capable of blocking the active site pocket of thrombin and inhibiting the function of catalytic residues contained therein.

We determined that the minimal distance from the ε-NH$_2$ of Lys-149 to the β-hydroxylate of Ser-195 is 18–20 Å.

Based on a 3 Å/amino acid residue length, we calculated that at least about 4–7 amino acids would be required to link a hirudin peptide, such as Sulfo-Tyr$_{63}$ hirudin$_{54-64}$, to a domain comprising an active-site inhibitor structure. The composition of the linker was designed to be glycine. Glycine was chosen in order to engineer the greatest flexibility of a linker for these preliminary investigations. It should be understood, however, that other, more rigid biopolymer linkers may also be employed.

We chose the sequence (D-phe)-Pro-Arg-Pro as the active site inhibitor because thrombin exhibits specificity for Arg as the P$_1$ amino acid in the cleavage of substrates. A Pro following the Arg yields a bond that is cleaved very slowly by thrombin. We designed alternate peptides by replacing Pro (following the P$_1$ Arg) with a sarcosyl- or N-methyl-alanine amino acid or by chemical reduction of an Arg-Gly scissile bond.

EXAMPLE 4

Synthesis Of Hirulog-8

Hirulog-8 has the formula: H-(D-Phe)-Pro-Arg-Pro-(Gly)$_4$-Asn-Gly-Asp-Phe-Glu-Glu-Ile-Pro-Glu-Glu-Tyr-Leu-OH. We synthesized Hirulog-8 by conventional solid-phase peptide synthesis employing an Applied Biosystems 430 A Peptide Synthesizer. This peptide was synthesized using BOC-L-Leucine-O-divinylbenzene resin. Additional t-BOC-amino acids (Peninsula Laboratories, Belmont, Calif.) used included BOC-O-2,6-dichlorobenzyl tyrosine, BOC-L-glutamic acid (γ-benzyl ester), BOC-L-proline, BOC-L-isoleucine, BOC-L-phenylalanine, BOC-L-aspartic acid (β-benzyl ester), BOC-glycine, BOC-L-asparagine, BOC-D-phenylalanine, and BOC-L-arginine. In order to achieve higher yields in synthesis, the (Gly)$_4$ linker segment was attached in two cycles of manual addition of BOC-glycylglycine (Beckman Biosciences, Inc., Philadelphia, Pa.). After completion of synthesis, the peptide was fully deprotected and uncoupled from the divinylbenzene resin by treatment with anhydrous HF:p-cresol:ethylmethyl sulfate (10:1:1, v/v/v). Following removal from the resin, the peptide was lyophilized to dryness.

Crude Hirulog-8 was purified by reverse-phase HPLC employing an Applied Biosystems 151A liquid chromatographic system and a Vydac C$_{18}$ column (2.2×25 cm). The column was equilibrated in 0.1% TFA/water and developed with a linear gradient of increasing acetonitrile concentration from 0 to 80% over 45 minutes in the 0.1% TFA at a flow-rate of 4.0 ml/min. The effluent stream was monitored for absorbance at 229 nm and fractions were collected manually. We purified 25–30 mg of crude Hirulog-8 by HPLC and recovered 15–20 mg of pure peptide.

We confirmed the structure of purified Hirulog-8 by amino acid and sequence analyses. Amino acid hydrolysates were prepared by treating the peptide with 6N HCl, in vacuo, at 110° C. for 24 hrs. We then analyzed the hydrolysates by ion-exchange chromatography and subsequent ninhydrin derivatization/detection using a Beckman 6300 automated analyzer. We performed sequence analysis using automated Edman degradation on an Applied Biosystems 470A gas-phase sequencer equipped with a Model 900A data system. Phenylthiohydantoin (PTH) amino acids were analyzed on-line using an Applied Biosystems 120A PTH-analyzer and a PTH-C$_{18}$ column (2.1×220 mm).

EXAMPLE 5

Synthesis Of Hirulog-9

Hirulog-9 has the formula: H-(D-Phe)-Pro-Arg-D-Pro-(Gly)$_4$-Asn-Gly-Asp-Phe-Glu-Glu-Ile-Pro-Glu-Glu-Tyr-Leu-OH. We synthesized this peptide in the same manner as that described in Example 4 using BOC-D-proline (Peninsula Laboratories) at cycle 15 in lieu of BOC-L-proline. Purification and characterization were performed as described in Example 4.

EXAMPLE 6

Synthesis Of Hirulog-10

Hirulog-10 has the formula: H-(D-Phe)-Pro-Arg-Sar-(Gly)$_5$-Asn-Gly-Asp-Phe-Glu-Glu-Ile-Pro-Glu-Glu-Tyr-Leu-OH. The peptide was synthesized as in Example 4 using BOC-sarcosine (Sigma Chemical Co., St. Louis, Mo.) at cycle 16. Purification and characterization were performed as described in Example 4.

EXAMPLE 7

Synthesis Of Hirulog-11

Hirulog 11 has the formula: H-(D-Phe)-Pro-Arg-Pro-(Gly)$_4$-Asn-Gly-Asp-Phe-Glu-Glu-Ile-Pro-Glu-Glu-(3,5-diiodoTyr)-Leu-OH. This peptide is synthesized as in Example 4 using BOC-3,5-diiodo-L-tyrosine (Sigma) at cycle 2. Purification and characterization is performed as described in Example 4.

EXAMPLE 8

Synthesis Of Hirulog-12

Hirulog 12 has the formula: H-(D-Phe)-Pro-Arg-Pro-(Gly)$_4$-Asn-Gly-Asp-Phe-Glu-Glu-Ile-Pro-Glu-Glu-Tyr(OSO$_3$)-Leu-OH. This peptide is synthesized by reacting 1.0 mg of Hirulog-8 in dimethylformamide (80 μl) with dicyclohexylcarbodiimide solution (1.25 g/ml, 0.007 ml) and concentrated sulfuric acid (0.5 μl) at 0° C. for 10 minutes. The reaction is stopped by addition of water (1.0 ml).

The reaction mixture may be subjected to reverse-phase HPLC employing an Applied Biosystems 150A Liquid Chromatographic System and an Aquapore RP-300 C$_8$ column (0.46×10 cm). The column is equilibrated in solvent A (0.1% TFA/water) and developed with an increasing concentration of solvent B (0.085% TFA/70% acetonitrile) from 0 to 50% over 45 minutes at a flow-rate of 1.0 ml/min. The effluent stream is monitored for absorbance at 214 nm.

Purified Hirulog-12 is then neutralized to pH 7 by adding 0.1N NaOH. It is then lyophilized and re-constituted in phosphate-buffered saline.

EXAMPLE 9

Inhibition Of Thrombin-Catalyzed Hydrolysis Of A p-Nitroanilide Synthetic Substrate By Hirulog-8

We next analyzed the effects of Hirulog-8 on the human α-thrombin-catalyzed hydrolysis of Spectrozyme TH (tosyl-Gly-Pro-Arg-p-nitroanilide; American Diagnostica, New York, N.Y.). Specifically, we measured the initial rate velocities in the presence or absence of Hirulog-8 over a range of substrate concentrations from 2.2 to 22 μM. The thrombin-catalyzed rate was monitored in a Cary 19 spectrophotometer at 405 nm and recorded continuously as a function of time. Kinetics were performed at room temperature (25°±1° C.) in a 0.05M Tris, pH 7.5, 0.1M NaCl buffer.

For a typical enzyme reaction, 1.0 ml of buffer was added to both the sample and reference cuvettes. Thrombin (3.2×

$10^{-9}$M, final concentration) and Hirulog-8 (0–4×$10^{-8}$M) were added to the sample cuvette prior to addition of Spectrozyme TH (2.2–22 µM). Immediately following addition of substrate, the contents of the sample cuvette were mixed by use of a plastic pipette. The reaction was monitored spectrophotometrically for 5–15 minutes.

Figure 3A:
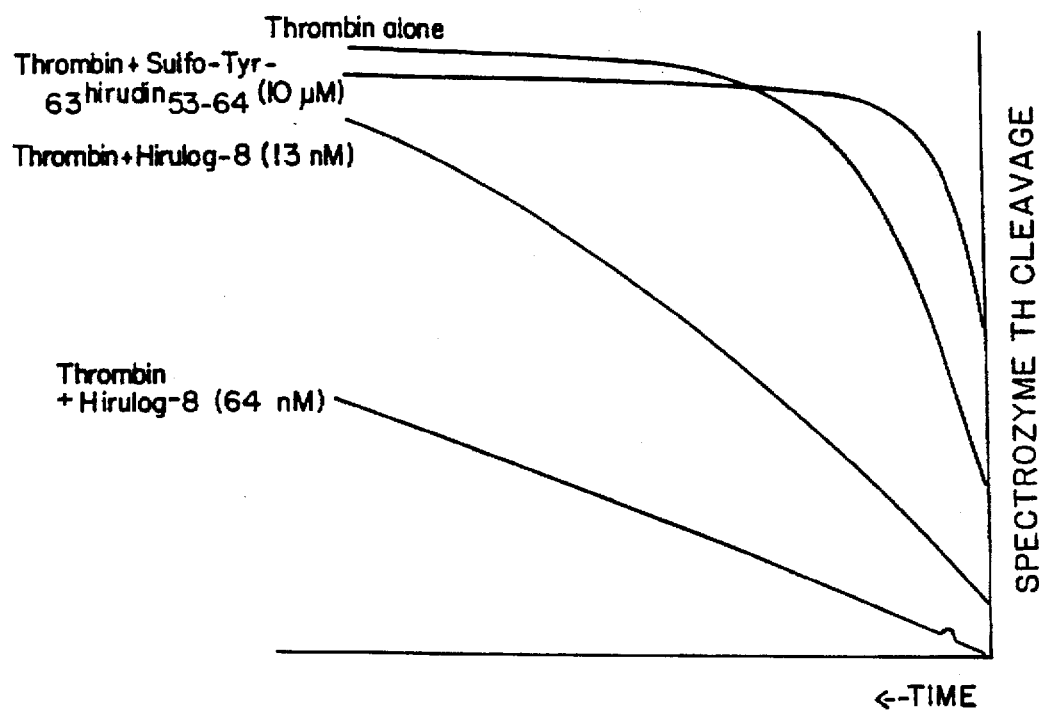
FIG. 3A, depicts the effects of Hirulog-8 and Sulfo-Tyr$_{63}$hirudin$_{53-64}$ on the cleavage of Spectrozyme TH by human α-thrombin.
Figure 3B:
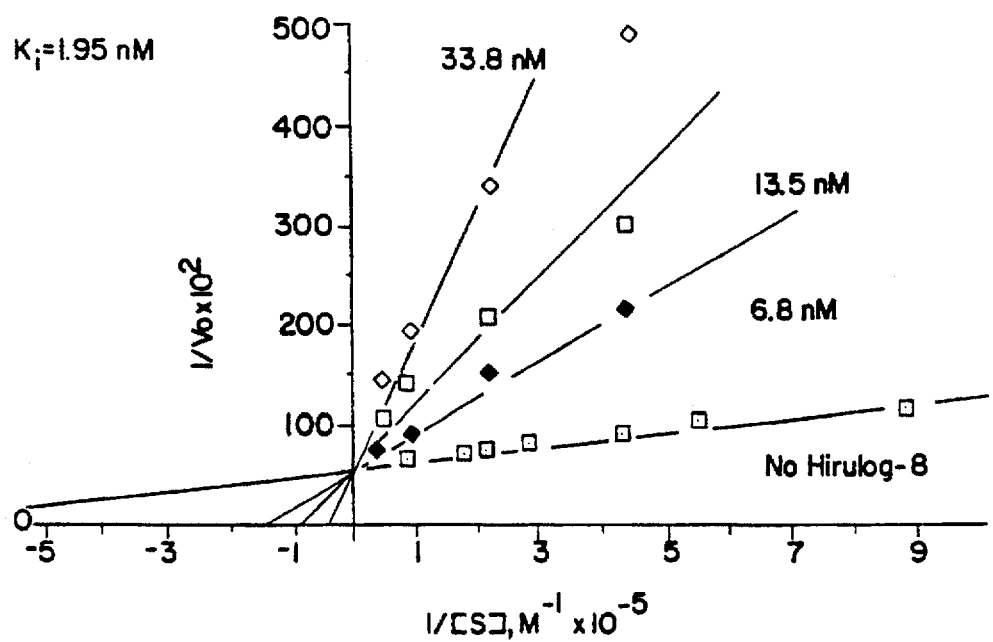
FIG. 3B, depicts a Lineweaver-Burke plot of the cleavage of Spectrozyme TH by human α-thrombin in the presence or absence of either Hirulog-8 or Sulfo-Tyr$_{63}$hirudin$_{53-64}$.

Initial rate velocities at each substrate concentration were expressed as moles Spectrozyme TH hydrolyzed/sec/mole thrombin. This was determined during the initial linear phase of the reaction (≦15% total hydrolysis of substrate) by measuring the slope of the hydrolytic reaction. Lineweaver-Burke plots were constructed accordingly, by plotting the inverse of the initial velocity against the inverse of the substrate concentration. The results showed that human α-thrombin-catalyzed hydrolysis of Spectrozyme TH had a $V_{max}$=17 moles hydrolyzed/sec/mole thrombin and a $K_M$ at 1.19×$10^{-6}$M. FIG. 3, panels A and B, demonstrates that increasing concentrations of Hirulog-8 led to significant, dose-dependent increases in the $K_M$, with slight increases in the $V_{max}$ for Spectrozyme TH hydrolysis. Therefore, the inhibition of the thrombin-catalyzed reaction by Hirulog-8 was carried out by mixed competitive/non-competitive components with respect to Spectrozyme TH hydrolysis. The $K_i$ of Hirulog-8 for α-thrombin was determined using the equation:

$$\left( \frac{V_{max}}{K_{M\ inhibited}} \right) = \left( \frac{V_{max}}{K_{M\ uninhibited}} \right) \times \left( 1 + \frac{[\text{Hirulog-8}]}{K_i} \right)$$

where ($V_{max}/K_{M\ inhibited}$) is the slope of the thrombin-catalyzed reaction in the presence of Hirulog-8; [Hirulog-8] is the molar concentration of peptide; ($V_{max}/K_{M\ uninhibited}$) is the the thrombin-catalyzed reaction in the absence of inhibitor; and $K_1$ is the molar inhibitory constant for Hirulog-8 with human α-thrombin. The $K_1$ for Hirulog-8 was calculated to be 1.95±0.11×$10^{-9}$M.

EXAMPLE 10

Specificity Of Hirulog-8 For The Hirudin-Peptide Binding Site And Active Site Of Human α-Thrombin Hirulog-8 was designed as an analogue that binds human α-thrombin via its hirudin peptide binding site while blocking thrombin's catalytic site. We tested the ability of Hirulog-8 to perform these functions by various studies described below.

The kinetics of Hirulog-8 inhibition of human γ-thrombin were studied essentially as described above in Example 9 for human α-thrombin. The γ-thrombin-catalyzed reaction toward Spectrozyme TH demonstrated a $V_{max}$=7.14 moles hydrolyzed/sec/mole thrombin and $K_M$= 1.1×$10^{-6}$M. These results confirm that γ-thrombin, a proteolytic form of thrombin, exhibits nearly complete catalytic competence, although this form essentially lacks clotting activity [S. D. Lewis et al., "Catalytic Competence of Human α- and γ-Thrombins in the Activation of Fibrinogen and Factor XIII", *Biochemistry*, 26, pp. 7597–7603 (1987)]. The inhibition of γ-thrombin by Hirulog-8 was examined over a range of peptide concentrations from 2.7×$10^{-8}$ to 6.8×$10^{-6}$M. As shown below, Hirulog-8 exhibited an increased $K_1$ of 3 orders of magnitude relative to α-thrombin. This high $K_1$ toward γ-thrombin is due to the absence of an intact anion binding exosite (ABE) in γ-thrombin [J. W. Fenton, II, et al., "Anion-Binding Exosite of Human α-Thrombin and Fibrin (ogen) Recognition", *Biochemistry*, 27, pp. 7106–12 (1988)]. γ-thrombin is formed by proteolysis of the B-chain of α-thrombin at Lys-149 and Arg-78.

The inhibition of human α-thrombin by Hirulog-8 was significantly reduced in the presence of Sulfo-Tyr$_{63}$-N-acetyl-hirudin$_{54-64}$ at concentrations of 2.6×$10^{-6}$M to 1.29× $10^{-5}$M. This is because Sulfo-Tyr$_{63}$-N-acetyl-hirudin$_{54-64}$ competes with Hirulog-8 for binding to the ABE of thrombin.

This was also demonstrated by the addition of phenylmethylsulfonyl-α-thrombin ("PMS-α-thrombin"; 18 nM, final) to reactions of Hirulog-8 with human α-thrombin. The addition of this modified thrombin resulted in a substantial decrease in the ability of Hirulog-8 to inhibit α-thrombin. PMS-α-thrombin has an intact ABE, but is covalently derivatized at its active site. This modified thrombin sequesters the Hirulog-8 in the reaction mix and therefore reduces the amount of peptide available to inhibit intact, catalytically-active human α-thrombin.

We also performed studies of the effect of salt concentrations on the $K_1$ of Hirulog-8 for thrombin as described above in Example 9. We measured the $K_1$ in the presence or absence of Hirulog-8 (11.5×$10^{-9}$M) in buffers containing 0.1, 0.25, and 0.5M NaCl. As shown in the table below, inhibition of α-thrombin by Hirulog-8 increased at lower salt concentrations. This result confirmed that the interaction of the highly anionic hirudin peptide moiety of Hirulog-8 with the positively-charged site surrounding Lys-149 of thrombin is essential for Hirulog-8 inhibition of thrombin-catalyzed hydrolysis of Spectrozyme TH.

| Enzyme | Conditions | Hirulog-8, $K_i$, nM |
| --- | --- | --- |
| Human α-thrombin | 0.05 M Tris, pH 7.5 0.1 M NaCl (Buffer) | 1.95 |
| Human γ-thrombin | Buffer | 1,080 |
| Human α-thrombin | Buffer + 2.6 µM Sulfo-Tyr$_{63}$-N-acetyl-hirudin$_{53-64}$ | 25.5 |
| Human α-thrombin | Buffer + 12.9 µM Sulfo-Tyr$_{63}$-N-acetyl-hirudin$_{53-64}$ | >2,000 |
| Human α-thrombin | Buffer + P MS-α-thrombin | 9.90 |
| Human α-thrombin | 0.05 M Tris, pH 7.5 0.25 M NaCl | 2.09 |
| Human α-thrombin | 0.05 M Tris, pH 7.5, 0.5 M NaCl. | 3.72 |

EXAMPLE 11

Anticoagulant Activity Of Hirulog-8: Comparison To Hirudin And Sulfo-Tyr$_{63}$-N-Acetyl-hirudin$_{54-64}$ We studied the anticoagulant activity of Hirulog-8 using pooled, normal human plasma (George King Biomedical, Overland Park, Kans.) and a Coag-A-Mate XC instrument (General Diagnostics, Organon Technica, Oklahoma City, Okla.). Activity was monitored using the activated partial thromboplastin time (APTT) assay with CaCl$_2$ and phospholipid solutions obtained from the manufacturer. Hirulog-8, hirudin, or Sulfo-Tyr$_{63}$-N-acetyl-hirudin$_{54-64}$ was then added to the APTT determination wells at a final concentrations of 10 to 32,300 ng/ml in a total volume of 25 µl prior to addition of 100 µl of plasma.

Figure 4:
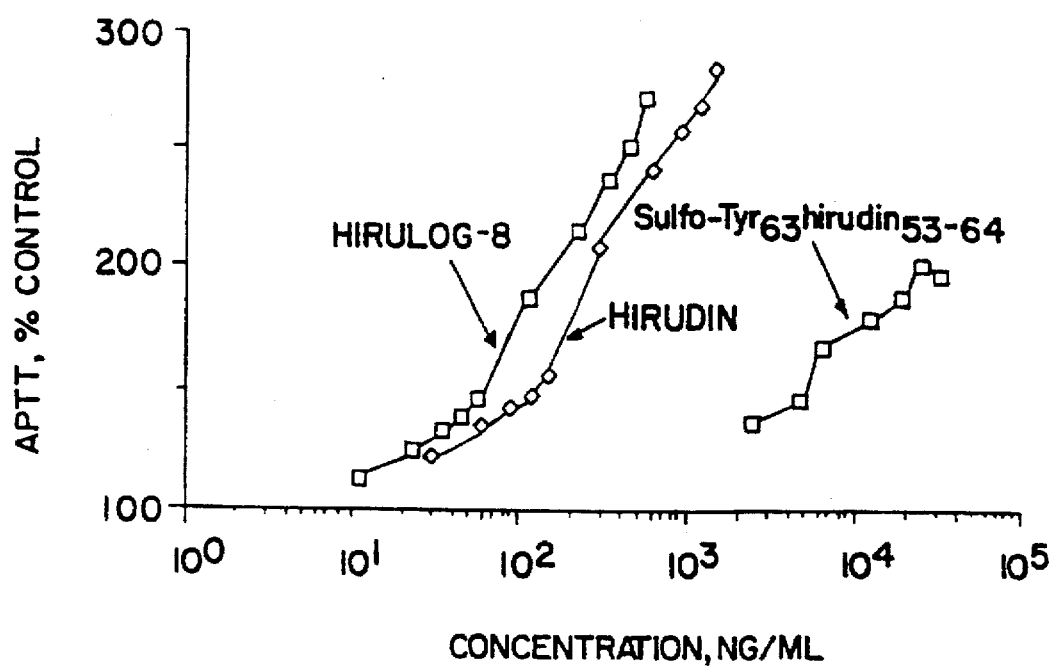
FIG. 4 depicts the effect of varying concentrations of Hirulog-8, hirudin, or Sulfo-Tyr$_{63}$-N-acetyl-hirudin$_{53-64}$ on the activated partial thromboplastin time of normal human serum.

The control APTT (absence of inhibitor) was 29.6 sec (mean, n=8, SEM<0.5%). FIG. 4 shows the results of these dose-dependency studies. Hirulog-8 was 2 to 3 times more potent than hirudin and 100 to 150 times more potent than Sulfo-Tyr$_{63}$-N-acetyl-hirudin$_{54-64}$. Both Hirulog-8 and hirudin increased the APTT of plasma to values which were too high to be measured. This is in contrast to Sulfo-Tyr$_{63}$-N-acetyl-hirudin$_{54-64}$, which exhibited a saturable dose-response in the APTT to 200–250% of control valves [J. M. Maraganore et al., *J. Biol. Chem.*, 264, pp. 8692–98, (1989)]. This result showed that Hirulog-8 can block the active site of thrombin in plasma, as well as in vitro in chromogenic assays, in a manner similar to hirudin.

EXAMPLE 12

Inhibition Of Thrombin Induced Platelet Activation By Hirulog-8

Thrombin-induced platelet activation studies are performed at 37° C. using a Biodata PAP$_4$ Platelet Aggregometer. Platelet-rich plasma (PRP) is obtained from normal, healthy, volunteers who have not taken any medication altering platelet function for at least one week prior to study. PRP is prepared as described by J. A. Jakubowski et al., "Modification of Human Platelet by a Diet Enriched in Saturated or Polyunsaturated Fat", *Atherosclerosis*, 31, pp. 335–44 (1978). Varying concentrations of Hirulog-8 (0–500 ng/ml in 50 µl water) are added to 0.4 ml of pre-warmed (37° C.) PRP. One minute later, we add human α-thrombin to the platelet suspension to a final concentration of 0.2, 0.25 or 0.5 units/ml total assay volume. Aggregation is monitored as an increase in light transmission for 5 minutes following the addition of thrombin. We then calculate % Inhibition as (% aggregation$_{sample}$)/(% aggregation$_{control}$)×100. This study shows that Hirulog-8 blocks thrombin-induced platelet activation in vitro.

EXAMPLE 13

Use Of Hirulog-8 In Thrombus Imaging

Hirulog-8 is modified by covalent attachment of an $^{123}$I-containing chemical group. Specifically, Hirulog-8 (as prepared in Example 4) is reacted with $^{123}$I-Bolton Hunter Reagent (New England Nuclear, Boston, Mass.) in 0.1M sodium borate, pH 9.0. The $^{123}$I-labelled molecule (with a specific activity of >5 µCi/µg) is then desalted on a Biogel P2 column which is equilibrated in a phosphate-buffered saline.

Ex vivo imaging of experimental thrombi is performed essentially as described by T. M. Palabrica et al., "Thrombus Imaging in a Primate Model with Antibodies Specific for an External Membrane Protein of Activated Platelets", *Proc. Natl. Acad. Sci. USA*, 86, pp. 1036–40 (1989). Specifically, imaging is performed in baboons using an external Ticoflex shunt between the femoral artery and femoral vein. An experimental thrombus is formed by placement of a segment of preclotted Dacron graft in the shunt. $^{123}$I-labelled thrombin inhibitor is injected in the venous portion of the Ticoflex shunt. Serial anterior images are then obtained for 0.5 to 1 hour using an Ohio Nuclear Series 100 Gamma Camera with a PDP-11/34 computer. The kinetics of $^{123}$I-thrombin inhibitor uptake by the graft and the blood pool are derived from the radionuclide images thus obtained.

The same technique may be used to obtain ex vivo images of a deep venous thrombus caused by stasis in the femoral vein of baboons. Because $^{123}$I-Hirulog-8 binds to thrombin with high specificity, the use of this molecule allows precise ex vivo images of thrombi. Also, the small size of Hirulog-8, in contrast to native hirudin or antibodies to thrombin, provides the potential that the radiolabelled thrombin inhibitor will yield images of platelet-bound thrombin and meizothrombin, as well as thrombin contained in the fibrin clot.

EXAMPLE 14

Anti-Metastatic Activity of Thrombin Inhibitors

The anti-metastatic activity of the thrombin inhibitors of this invention, preferably Hirulog-8, is assayed using sarcoma T241 cells [L. A. Liotta et al., *Nature*, 284, pp. 67–68 (1980)] and syngeneic C57BL/6 mice (Jackson Laboratory, Bar Harbor, Me.). The mice are injected either intravenously or subcutaneously with 0–250 g/kg of Hirulog-8, prepared as in Example 4, followed by injection with $10^4$–$10^6$ T241 tumor cells. After 15 days, the animal is sacrificed and lung tumor colonies are quantitated. Anti-metastatic activity of Hirulog-8 is measured as percent reduction in tumor colonies compared to placebo-treated control mice. Hirulog-8 demonstrates anti-metastatic activity in this assay.

EXAMPLE 15

Inhibition Of Endothelial Cells By A Thrombin Inhibitor

The ability of the thrombin inhibitors of this invention to prevent thrombin-induced synthesis of platelet activating factor (PAF) is assayed using cultured human umbilical vein endothelial cells (HUVECs). HUVECS are extracted from human umbilical cords by collagenase digestion according to established procedures [M. A. Gimborne, Jr., "Culture of Vascular Endothelium", *Prog. Hemost. Thromb.*, 3, pp. 1–28 (1976)]. HUVECs are grown to confluence in a 96-well microtiter plate in the presence of [$^3$H]-acetate. Cells cultured in this manner produce [$^3$H]-acetyl-PAF, which may be quantitated by extraction of HUVEC membrane phospholipids.

Hirulog-8 (0–1 µg/ml) is added to the [$^3$H]-acetate loaded HUVECs 1 minute prior to the addition of thrombin (final concentration of 1 U/ml). Cells are incubated for 5 minutes and the supernatant is then removed. Medium containing 0.1% gelatin, 50 mM acetic acid in methanol (2:1 v/v) is then added to the HUVECs. PAF is then extracted and quantified using conventional techniques [T. M. Mcintyre et al., "Cultured Endothelial Cells Synthesize Both Platelet-Activating Factor and Prostacyclin in Response to Histamine, Bradykinin and Adenosine Triphosphate", *J. Clin. Invest.*, 76, pp. 271–80 (1985)]. The IC$_{50}$ values are then calculated. Hirulog-8 inhibits the synthesis of PAF by HUVECs in this assay.

The effect of Hirulog-8 on thrombin-induced polymorphonuclear leukocyte (PMN) adhesion to HUVECs may be demonstrated as follows. HUVECs are grown to confluence in MEM containing 1% fetal calf serum in 24-well cluster plates. The medium is then removed, the cells are washed two times with fresh, serum-free medium and incubated in the same medium for 10–30 minutes at 37° C. to remove serum products. PMNs (2.5×10$^6$ in 1 ml), which are pre-equilibrated at 37° C., are then added to each well. The PMNs are allowed to settle onto the HUVEC monolayer for 2 minutes. Hirulog-8 (5 µg/ml) or saline is added to each well, immediately followed by the addition of α-thrombin (0.1 or 1 U/ml). The cells are incubated for 5 minutes at 37° C., washed twice and then examined by phase-contrast microscopy. Adherent PMNs are counted directly. Samples incubated with Hirulog-8 have significantly fewer adherent PMNs than those treated with saline.

EXAMPLE 16

Synthesis Of Hirulog-13

Hirulog-13 has the formula: H-(D-Phe)-Pro-Arg-Pro-(Gly)$_2$-Asn-Gly-Asp-Phe-Glu-Glu-Ile-Pro-Glu-Glu-Tyr-Leu-OH. We synthesized, purified and characterized this peptide essentially as described in Example 4, except that only one cycle of BOC-glycylglycine was employed to produce the diglycine segment.

EXAMPLE 17

Synthesis Of Hirulog-14

Hirulog-14 has the formula: H-(D-Phe)-Pro-Arg-Pro-(Gly)$_2$-Asn-Gly-Asp-Phe-Glu-Glu-Ile-Pro-Glu-Glu-Tyr-Leu-OH. Hirulog-14 was synthesized, purified and characterized using methods described in Example 4, except that one cycle of BOC-glycine addition was employed following the two cycles of BOC-glycylglycine addition to produce the pentaglycine segment.

EXAMPLE 18

Synthesis Of Hirulog-15

Hirulog-15 has the formula: H-(D-Phe)-Pro-Arg-Pro-(Gly)$_6$-Asn-Gly-Asp-Phe-Glu-Glu-Ile-Pro-Glu-Glu-Tyr-Leu-OH. Hirulog-15 was synthesized, purified and characterized using methods described in Example 4, except that three cycles of BOC-glycylglycine addition were employed to prepare the hexaglycine segment.

EXAMPLE 19

Synthesis Of Hirulog-16

Hirulog-16 has the formula: H-(D-Phe)-Pro-Arg-Pro-(Gly)$_8$-Asn-Gly-Asp-Phe-Glu-Glu-Ile-Pro-Glu-Glu-Tyr-Leu-OH. Hirulog-16 was prepared, purified and characterized as described in Example 4, except that four cycles of BOC-glycylglycine addition were used to prepare the octaglycine segment.

EXAMPLE 20

Synthesis Of Hirulog-17

Hirulog-17 has the formula: H-(D-Phe)-Pro-Arg-Pro-Gly-Gly-Glu-Gly-His-Gly-Asn-Gly-Asp-Phe-Glu-Glu-Ile-Pro-Glu-Glu-Tyr-Leu-OH. Hirulog-17 was synthesized essentially as described in Example 4, except that a Gly-Gly-Glu-Gly-His-Gly replaced the Gly$_4$ segment present in Hirulog-8. This sequence was added on to the growing peptide chain by the consecutive additions of BOC-glycine, BOC-L-histidine, BOC-glycine, BOC-L-glutamic acid and BOC-glycylglycine at cycles 13–17 of synthesis. Purification and characterization were performed as described in Example 4.

EXAMPLE 21

Synthesis Of Hirulog-18a, -18b And -18c

Hirulog-18a has the formula: H-(D-Phe)-Pro-(β-homoarginine)-(Gly)$_5$-Asn-Gly-Asp-Phe-Glu-Glu-Ile-Pro-Glu-Glu-Tyr-Leu-OH. Hirulog-18b has the formula: H-(D-Phe)-Pro-(β-homoarginine)-Pro-(Gly)$_4$-Asn-Gly-Asp-Phe-Glu-Glu-Ile-Pro-Glu-Glu-Tyr-Leu-OH. Hirulog-18c has the formula: H-(D-Phe)-Pro-(β-homoarginine)-Val-(Gly)$_4$-Asn-Gly-Asp-Phe-Glu-Glu-Ile-Pro-Glu-Glu-Tyr-Leu-OH. We synthesized Hirulog-18a using a mixed homogeneous/solid-phase procedure. Residues 5–20 were prepared by solid-phase synthesis, as described in Examples 4 and 17. The resulting resin-linked intermediate was reacted with a BOC-β-homoarginine-Gly protected intermediate, which was synthesized in the multi-step reaction scheme depicted below and described immediately thereafter.

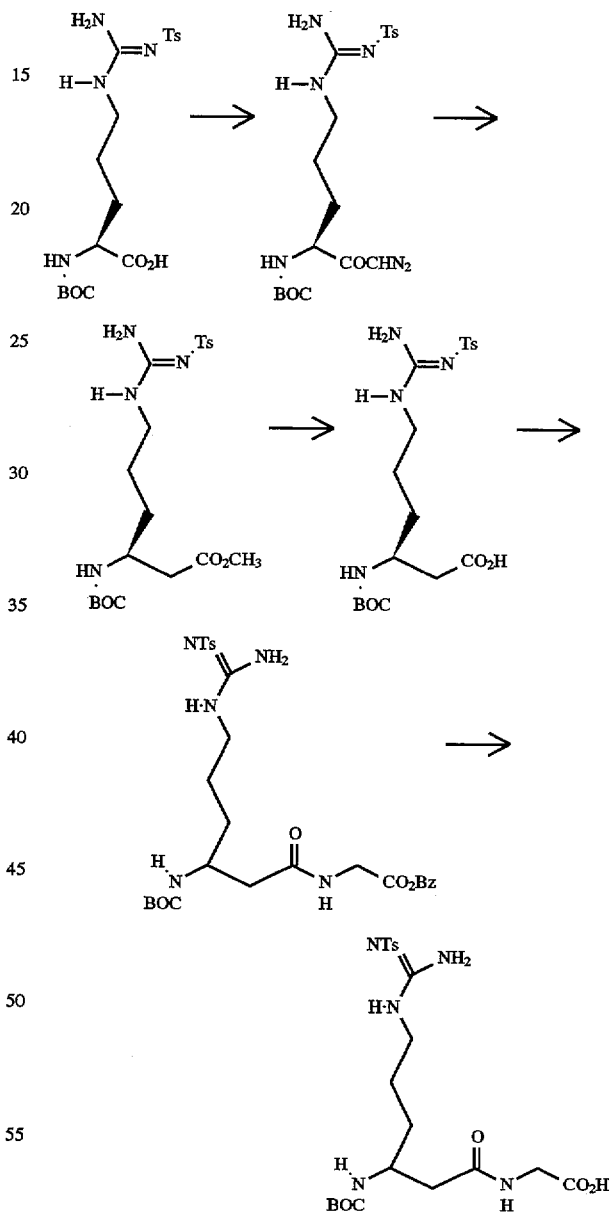

$N^\alpha$-BOC-$N^g$-Tos-ArginineDiazomethylketone

We stirred 10 g (13.4 mmoles) of $N^\alpha$-BOC-$N^g$-Tos-arginine (Bachem, Torrance, Calif.) and 2.1 ml (19.1 mmole) of N-methylmorpholine (Aldrich, Milwaukee, Wis.) in 100 ml anhydrous tetrahydrofuran (THF) under argon for 5 minutes at room temperature. The solution was then cooled to −15° C. and 2.8 ml (21.6 mmol) of isobutylchloroformate (Aldrich) was added. We continued to stir the reaction mixture at −15° C. for 5 minutes, and then filtered it through a pad of Celite/MgSO$_4$. We next added the filtrate to an ice-cold ethereal solution of diazomethane (150 mM, generated from 32.4 g Diazald; Aldrich). The solution was stirred and allowed to gradually reach ambient temperature overnight. The solvent was then removed in vacuo and the residue dissolved in 200 ml chloroform. We then washed the organic solution successively with 200 ml of saturated NaHCO$_3$, followed by 200 ml of saturated NaCl, dried it over anhydrous MgSO$_4$, and concentrated it again to an oily residue. The residue was then purified by flash chromatography on a 4×17 cm column of silica gel using a step gradient of acetone in chloroform (10% acetone in 2 l chloroform, followed by 20% acetone in 3 l chloroform). Fractions of 25 ml were collected. Aliquots of each fraction were assayed by thin-layer chromatography (TLC). Fractions containing the desired product were pooled and evaporated to dryness. The product, diazomethylketone, was purified as a pale yellow foam (6.54 g).

N$^\alpha$-BOC-N$^g$-Tos-β-Homoarginine Methylester

We dissolved the diazomethylketone prepared above in 100 ml of anhydrous methanol and refluxed that solution under argon while a solution of silver benzoate catalyst (165 mg in 400 μl triethylamine) was added dropwise. After 30 minutes, the refluxing solution was cooled to room temperature, slurried with Norit, and filtered through Celite. The solvent was then removed in vacuo and the oily residue purified by flash chromatography over silica gel. Elution was achieved with 4 l of 10% acetone in chloroform. The desired product, β-homoarginine methylester, was thus purified as a light tan foam (6.43 g).

N$^\alpha$-BOC-N$^g$-Tos-β-Homoarginine

We dissolved all of the above methyl ester in 100 ml of methanol and then reacted it with a solution of LiOH (1.48 g in 50 ml water) overnight at room temperature under argon with constant stirring. We removed the methanol in vacuo, dissolved the residue in water and washed it with ethyl acetate. We next added saturated citric acid until the solution reached a pH of 4. We then extracted the resulting carboxylic acid into ethyl acetate. The extraction was repeated at pH 3, and the combined organic phases were dried over MgSO$_4$ and concentrated in vacuo. The resulting crude acid was recovered as a white foam (4.9 g). The acid was further purified on a Vydac C$_{18}$ reverse-phase HPLC column, as described in Example 4, except that the effluent stream was monitored at 214 nm. Following lyophilization of the desired fractions, the product, N$^\alpha$-BOC-N$^g$-Tos-β-homoarginine, was recovered as a white amorphous solid.

A sample of the N$^\alpha$-BOC-N$^g$-Tos-β-homoarginine was hydrolysed in HF and used as a standard for amino acid analysis. The retention time of β-homoarginine was identical to that of arginine, but the intensity of the peak was considerably lower, as expected.

N$^\alpha$-BOC-N$^g$-Tos-β-Homoargininylglycine Benzylester

We next combined 4.06 g (9.2 mmoles) of the above carboxylic acid with 2.04 ml of N-methylmorpholine in 25 ml of anhydrous THF. The mixture was stirred under argon at −5° C. A chilled solution of isobutylchloroformate (2.4 ml in 25 ml THF) was then added dropwise to the solution over 10 minutes. Following this addition, the reaction mixture was stirred for 12 minutes at −5° C. For Hirulog-18a we then added a solution of glycine benzyl ester (4.9 g in 40 ml THF; 27.6 mmoles), and allowed the reaction mixture to come to room temperature. The solvent was then removed in vacuo and the resulting residue dissolved in 100 ml ethylacetate. The solution was extracted successively with 100 ml each of saturated NaHCO$_3$ and saturated NaCl, dried over MgSO$_4$, and concentrated in vacuo. The resulting crude dipeptide ester was purified on a 4×20 cm silica gel column with a methanol step gradient in chloroform containing 10 drops NH$_4$OH per 100 ml (2 l of 1% methanol in chloroform, followed by 3 l of 2% methanol in chloroform). Fractions (25 ml) were collected, assayed by TLC and those containing product were pooled and the solvent removed in vacuo. The resulting product, N$^\alpha$-BOC-N$^g$-Tos-β-homoargininylglycine benzylester, was isolated a white foam (3.9 g).

For Hirulog-18b and -18c, the above reaction was identical except for the following modifications: For Hirulog-18b, the glycine benzyl ester was replaced by proline benzyl ester and the reaction was run on a 1.8 mmole scale. For Hirulog-18c, the glycine benzyl ester was replaced with valine benzyl ester and the reaction was run on a 3.0 mmole scale.

N$^\alpha$-BOC-N$^g$-Tos-β-Homoargininylglycine

The above benzyl ester was dissolved in 50 ml methanol and hydrogenated at atmospheric pressure over 1.0 g of 10% palladium/carbon for 17 h. The resulting solution was filtered through Celite and the solvent removed in vacuo. The reaction yielded 2.9 g of crude N$^\alpha$-BOC-N$^g$-Tos-β-homoargininylglycine, which was purified on a Vydac C$_{18}$ HPLC column as described above.

The above N$^\alpha$-BOC-N$^g$-Tos-β-homoargininylglycine (1.02 g) was dissolved in 1 ml anhydrous DMF and cooled in an ice bath. We then added to this solution successively, 5.5 ml of 0.5M hydroxybenztriazole in DMF (Applied Biosystems Inc, Foster City, Calif.) and 5.5 ml of 0.5M dicyclohexylcarbodiimide in CH$_2$Cl$_2$ (Applied Biosystems). After 1 hour, the cold suspension of symmetrical anhydride of the dipeptide unit was then rapidly filtered through a plug of glass wool to remove the dicyclohexyl urea.

Meanwhile, a suspension of N-BOC-(Gly)$_4$-Asn-Gly-Asp-Phe-Glu-Glu-Ile-Pro-Glu-Glu-Tyr-Leu-O-PAM (0.2 mmol in CH$_2$Cl$_2$) was activated by standard peptide synthesis methods. A Kaiser test on the resulting product indicated a free terminal amino group.

The activated β-homoarginylglycine dipeptide was then coupled to the resin-bound hexadecapeptide. The resulting octadecapeptide was then coupled, successively, with N-BOC-Pro and N-BOC-(D-Phe) using standard coupling procedure. The resulting peptide, Hirulog-18a, was purified and characterized as described in Example 4.

A similar protocol was carried out for the synthesis of Hirulog-18b and Hirulog-18c.

EXAMPLE 22

Synthesis Of Hirulog-19

Hirulog-19 has the formula: H-(D-Phe)-Pro-Arg-[psiCH$_2$NH]-(Gly)$_5$-Asn-Gly-Asp-Phe-Glu-Glu-Ile-Pro-Glu-Glu-Tyr-Leu-OH. Residues 4-20 of this peptide were assembled by solid-phase peptide synthetic procedures as described in Example 4. The next residue added, N$^\alpha$-BOC-N$^g$-tosyl-argininal, was prepared as depicted and described below.

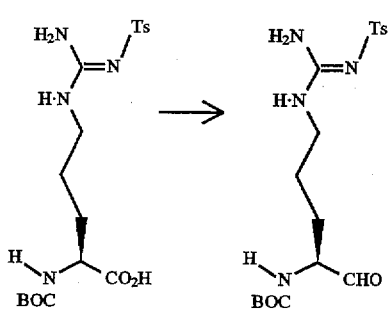

$N^\alpha$-BOC-$N^g$-Tos-Argininal $N^\alpha$-BOC-$N^g$-Tos-arginine (Bachem Inc.; 10 g) was added to 80 ml of anhydrous THF and the suspension cooled to 0°–5° C. We then added 1,1'-carbonyldiimidazole (Aldrich; 3.61 g) all at once and continued stirring for 20 minutes. The resulting clear solution was partially immersed in a dry ice/acetone bath to maintain a temperature of –20° to –30° C. during the dropwise addition of a suspension of lithium aluminum hydride (Aldrich; 1.8 g in 80 ml THF) over 45 minutes with constant stirring. The reaction was stirred an additional 30 minutes at –20° C. and was then quenched by the dropwise addition of 63 ml of 2N HCl at –10° C. We filtered the resulting solution through a medium scinter glass funnel and concentrated the resulting filtrate in vacuo.

The resulting crude aldehyde, recovered as a white foam (11.5 g), was suspended in 100 ml of chloroform, washed with water (2×50 ml) and the organic layer then dried over sodium sulfate and concentrated in vacuo. The crude aldehyde (7.7 g) was dissolved in 100 ml chloroform and purified by flash chromatography over a 5×20 cm flash column containing 350 ml silica gel (Merck Grade 60, 230–400 mesh, 60 Å). Elution was achieved using a step gradient of 0.5% methanol in 500 ml chloroform, 1% methanol in 1 l chloroform, and 1.5% methanol in 1 l chloroform. This procedure yielded 8.9 g of $N^\alpha$-BOC-$N^g$-Tos-argininal.

The $N^\alpha$-BOC-$N^g$-Tos-argininal (258 mg) was then added to the resin-bound (Gly)$_5$-Asn-Gly-Asp-Phe-Glu-Glu-Ile-Pro-Glu-Glu-Tyr-Leu-O-PAM under solid-phase reductive alkylation conditions (40 mg sodium cyanoborohydride for 24 hours) using the method of D. H. Coy et al., "Solid-Phase Synthesis of Peptides" In Peptides, Vol. 8, pp. 119–121 (1978). Following reaction of the resin-linked peptide with the protected argininal, the peptide synthesis was completed with a cycle of BOC-proline incorporation and a cycle of BOC-(D-phenylalanine) incorporation. After completion of the synthesis, Hirulog-19 was deprotected and uncoupled from the resin as described in Example 4.

Hirulog-19 was purified by reverse phase HPLC employing an Applied Biosystems 151A liquid chromatographic system and an Aquapore C, column (10×22 cm). The column was equilibrated in 1 part 70% acetonitrile/30% water containing 0.85% TFA (Buffer B) and 4 parts water containing 1% TFA (Buffer A). The column was developed with a linear gradient of increasing Buffer B concentration (20–50%) over 120 minutes at a flow rate of 4.0 ml/minute. The effluent stream was monitored for absorbance at 214 nm and fractions were collected manually. Further purification was carried out under isocratic conditions using 20% Buffer B/80% Buffer A.

EXAMPLE 23

Synthesis Of Hirulog-21

Hirulog-21 has the formula: H-(D-Phe)-Pro-Arg-Pro-(Gly)$_4$-Asn-Gly-Asp-Phe-Glu-Glu-Ile-Pro-Glu-Glu-Tyr-Leu-(Gly)$_2$-Lys-OH. Hirulog-21 was synthesized using methods described in Example 4, using the appropriate BOC-amino acids. Purification and characterization of Hirulog-21 were achieved by the methods described in Example 4.

EXAMPLE 24

Synthesis Of Hirulog-25

Hirulog-25 has the formula H-(D-Phe)-Pro-(4-Argininyl-2,2-difluoro)malonylglycyl-(Gly)$_4$-Asn-Gly-Asp-Phe-Glu-Glu-Ile-Pro-Glu-Glu-Tyr-Leu-OH. The hexadecapeptide, (Gly)$_4$-Asn-Gly-Asp-Phe-Glu-Glu-Ile-Pro-Glu-Glu-Tyr-Leu, was synthesized as previously described and left bound to the resin. The next residue, (3-Argininyl-2,2-difluoro)malonylglycine is synthesized in the reaction scheme depicted and detailed below.

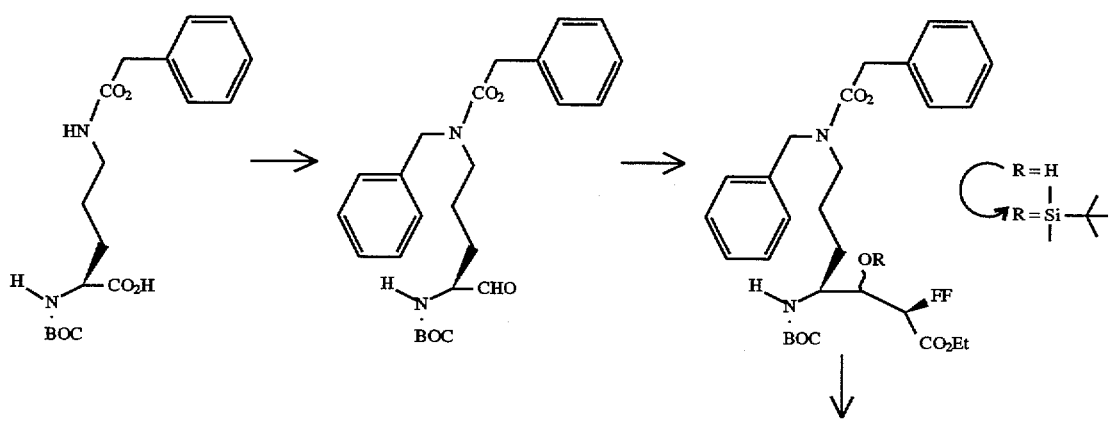

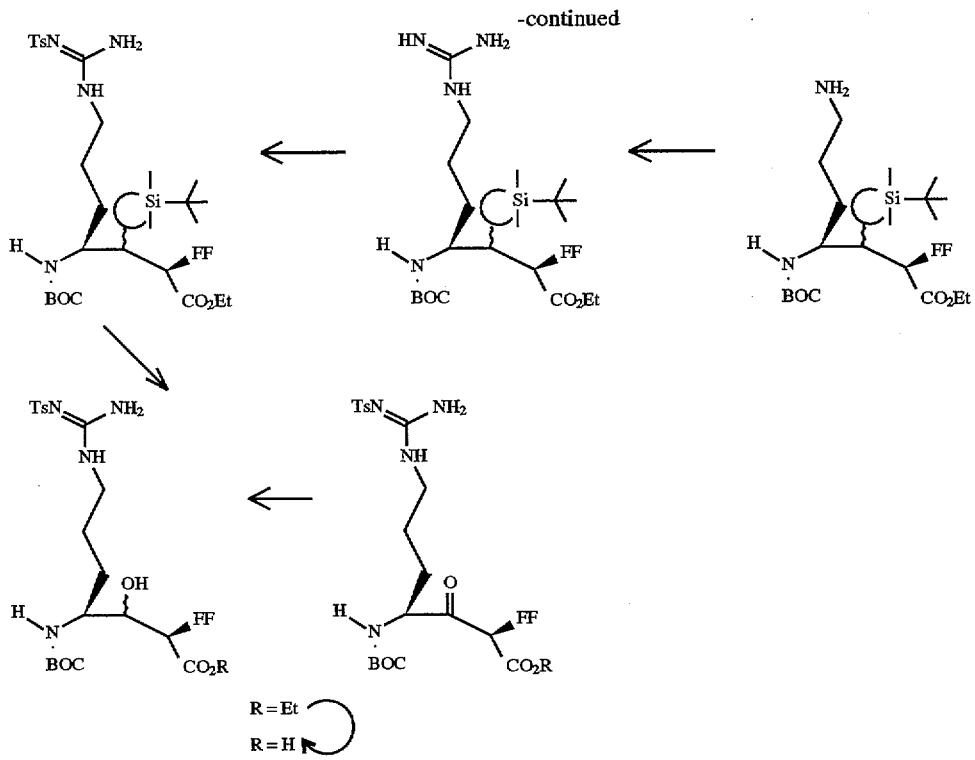

R = Et
R = H

1-[(2'-carboethoxy-1',1'-difluoro)ethyl]N$^\alpha$-BOC-N$^{om}$-CbzOrnithinol A solution of 3.1 g (7.1 mmoles) N$^\alpha$-BOC-N$^{om}$-Benzyl-N$^{om}$-CbzOrnithinal [F. Salituro et al., "Inhibition of Aspartic Proteinases By Peptides Containing Lysine and Onithine Side Chain Analogues of Statine", *J., Med, Chem.*, 30, pp. 286–95 (1987)], and 1.56 ml (9.23 mmoles) ethylbromodifluoroacetate in anhydrous 15 ml THF was added over 90 minutes to a refluxing suspension of 786 mg Zn powder (Fluka) in 15 ml THF under argon. After 4 hours to reflux and 2 hours at room temperature, the mixture was cooled and partitioned between 200 ml each of ethyl acetate and saturated NaCl/KHSO$_4$. The organic phase was isolated, dried over MgSO$_4$ and concentrated in vacuo. The resulting oily residue was purified on silica gel, using CHCl$_3$:methanol (90:10) plus 100 drops/l NH$_4$OH as eluant.

1-[(2'-Carboethoxy-1',1'-difluoro)ethyl]N$^\alpha$-BOC-Ornithinol tertButyldimethylsilyl Ether The resulting compound, 1-[(2'-carboethoxy-1'-1'-difluoro)ethyl]N$^\alpha$-BOC-N$^{om}$-benzyl-N$^{om}$-CbzOrnithinol, is then reacted with 5 equivalents of tertbutyldimethylsilyl chloride and 10 equivalents of imidazole in anhydrous DMF at 35° C., following the procedure of E. J. Corey et al., "Protection of Hydroxyl Groups as tertButyldimethylsilyl Derivatives", *J. Amer. Chem. Soc.*, 94, pp. 6190–91, (1972). The orthogonally protected amine is then dissolved in methanol and hydrogenated over Pd(OH)$_2$ at 30 psi for 18 hours. The catalyst is then removed by filtration and the filtrate concentrated in vacuo to produce 1-[(2'-carboethoxy-1'-1'-difluoro)ethyl]N$^\alpha$-BOC-Ornithinoltert-butyldimethylsilyl ether.

1-[(2'-Carboethoxy-1',1'-difluoro)ethyl]N$^\alpha$-BOC-N$^g$-Tos-Argininol-tertButyldimethylsilyl Ether The above-prepared compound is then reacted with 6.8 equivalents each of 1-quanyl-3,5-dimethylpyrazole and triethylamine in water at 105° C. for 24 hours. The mixture is then lyophilized and the residue subjected to preparative HPLC as described in Example 4. Fractions containing the desired guanidinium compound (assayed by TLC) are pooled and dried in vacuo. The residue is dissolved in H$_2$O:acetone (1:4), cooled in an ice bath and adjusted to pH 12 with 50% w/v NaOH. To this solution we add a solution of 3 equivalents of paratoluene sulfonylchloride in acetone over 60 minutes, while maintaining the pH at 11–12 with NaOH. The solution is allowed to warm to room temperature and is stirred overnight. The acetone is then removed in vacuo and the remaining aqueous solution is washed with ether. The ether layer is removed and back extracted with saturated NaHCO$_3$. The aqueous phases are combined and acidified to pH 3 with 2N HCl. The resulting acid solution is then extracted two times with ethyl acetate, dried and concentrated in vacuo to yield the desired product.

1-[(2'-Carboxy-1',1'-difluoro)ethyl]N$^\alpha$-BOC-N$^g$-Tos-Argininol

The resulting compound, 1-[(2'-carboethoxy-1'-1'-difluoro)ethyl]N$^\alpha$-BOC-N$^g$-Tos-Argininoltertbutyldimethylsilyl ether, is desilylated by treatment with 3 equivalents of tetra-n-butylammonium fluoride in THF at room temperature, as described in E. J. Corey et al., supra. The compound produced by this process is then saponified by treatment with 2.5 equivalents of LiOH in methanol/water at room temperature overnight under argon. The reaction mixture is then washed with ethyl acetate and acidified with citric acid to pH 4. We extract the resulting acid into ethyl acetate, dry the organic phase and concentrate it in vacuo. The crude acid is then purified on a Vydac C$_{18}$ reverse-phase HPLC column under the conditions described in Example 4.

1-[(2'-Carboxy1',1'-difluoro)ethyl]N$^\alpha$-BOC-N$^g$-Tos-Argininone

The alcohol function of the above compound is converted to the ketone by the addition of one equivalent of pyridinium dichromate in CH$_2$Cl$_2$ containing 0.5% glacial acetic acid in the presence of molecular sieves [N. Peet et al., "Synthesis of Peptidyl and Fluoromethyl Ketones and Peptidyl α-Keto Esters as Inhibitors of Porcine Pancreatic Elastase, Human Neutrophil Elastase, and Rat and Human Neutrophil Cathepsin G", *J. Med. Chem.*, 33, pp. 394–407 (1990)]. After stirring under argon for 15 hours, the reaction mixture is filtered and the solvent removed in vacuo. The resulting 1-[(2'-carboxy-1'-1'-difluoro)ethyl]N$^α$-BOC-N$^g$-Tos-Argininone is recovered as an oily residue and then purified on HPLC according to the conditions specified in Example 4.

The free carboxylic acid is converted to the symmetrical anhydride and reacted with resin-bound hexadecapeptide as described in Example 21. The two N-terminal residues of Hirulog-25, BOC-Pro and BOC-(D-Phe), are added under standard peptide synthesis conditions and the resulting peptide is then cleaved with HF.

EXAMPLE 25

Synthesis Of Hirulog-26

Hirulog-26 has the formula: H-(D-Phe)-Pro-Argoxopropionylglycyl-(Gly)$_4$-Asn-Gly-Asp-Phe-Glu-Glu-Ile-Pro-Glu-Glu-Tyr-Leu-OH. The hexadecapeptide, (Gly)$_4$-Asn-Gly-Asp-Phe-Glu-Glu-Ile-Pro-Glu-Glu-Tyr-Leu, was synthesized as previously described and left bound to the resin. The next residue, N$^α$-BOC-argoxopropionylglycine, is synthesized by the reaction scheme depicted and described below.

ketone described in Example 21, except for the substitution of N$^α$-Cbz-N$^g$-Tos-Arginine for N$^α$-BOC-N$^g$-Tos-Arginine. We dissolved 4.5 mg of N$^α$-Cbz-N$^g$-Tos-ArginineDiazomethyl ketone in 200 ml of CH$_2$Cl$_2$ in a flask and cooled the solution to –70° C. in a dry ice/acetone bath with stirring. Anhydrous HBr gas was then bubbled through the solution at a moderate flow rate for 15 minutes. The solution was stirred for an additional 15 minutes at –70° C. and then concentrated in vacuo. The resulting product, N$^α$-Cbz-N$^g$-Tos-Arg-COCH$_2$Br, was recovered as 5.0 g of yellow crystals.

Meanwhile, a suspension of sodium hydride (36 mg; 80% dispersion in oil) in 1 ml DMF and 1.2 ml hexamethylphosphoramide ("HMPA") was added to a solution of 259 mg di tertbutoxymalonate in 4 ml DMF. The mixture was stirred at room temperature for 40 minutes and was then added dropwise, over 20 minutes, to a solution of 1 mmole N$^α$-Cbz-N$^g$-Tos-Arg-COCH$_2$Br, in 1 ml DMF/0.13 ml HMPA. The reaction was allowed to proceed for 3 hours, after which time the solution was poured into 50 ml water and extracted with 2×50 ml ethyl acetate. The organic phase was isolated, dried and concentrated in vacuo to an oily residue. The residue was subsequently purified on a 3×10 cm silica gel column which was eluted successively with 400 ml of 5% acetone in chloroform, 400 ml of 10% acetone in chloroform and 200 ml of 20% acetone in chloroform. Fractions (25 ml) were collected and assayed by TLC. Fractions containing the desired product were pooled and concentrated to produce 3-(CbzAmino)-2-oxo-3-{3-[(N$^g$-Tos)guanidinyl]propyl}-di-tertButyl malonate.

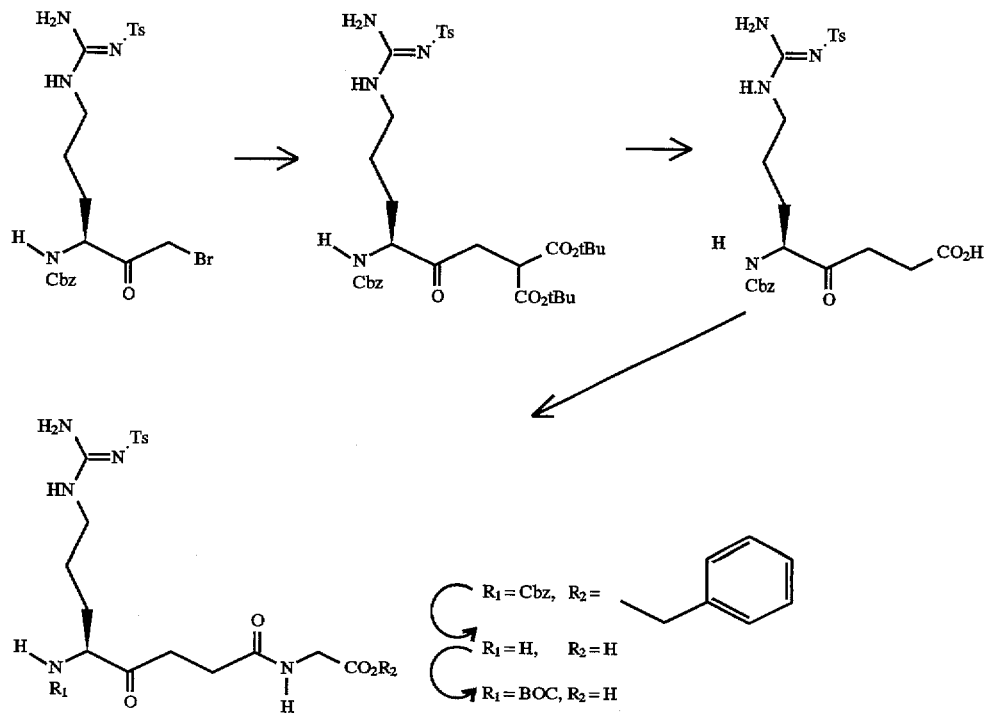

3-(CbzAmino)-2-oxo-3-{3-[(N$^g$-Tos)guanidinyl] propyl}-ditertButylMalonate 5-(N$^α$-CbzAmino)-4-oxo-5-{3-[(N$^g$-Tos)guanidinyl] propyl}pentanoylglycine Benzyl Ester We prepared a batch of N$^α$-Cbz-N$^g$-Tos-ArginineDiazomethyl ketone in the same manner as the preparation of N$^α$-BOC-N$^g$-Tos-ArginineDiazomethyl The above di-t butyl ester is stirred in 1.2 equivalents of 1N HCl for 2 hours at room temperature. It is then decarboxylated in excess pyridine at 100° C. for 15 minutes. The solvent is then removed in vacuo, and the residue purified by silica gel chromatography, as described above. The resulting carboxylic acid is acylated with glycine benzyl ester according to the method described in Example 21.

5-(Amino)-4-oxo-5-{3-[(N$^g$-Tos)guanidinyl]propyl}pentanoylglycine

The resulting ester is dissolved in 500 ml methanol and hydrogenated overnight at 1 atmosphere of hydrogen gas over 600 mg of 10% palladium-carbon catalyst. The reaction mixture is then filtered through Celite and concentrated in vacuo to a solid residue (155 mg). The resulting amino acid is then purified by HPLC, using the conditions described in Example 4.

5-(N$^\alpha$-BOCAmino)-4-oxo-5-{3-[(N$^g$-Tos)guanidinyl]propyl}pentanoylglycine The above amino acid is converted to its corresponding BOC derivative by dissolving in dioxane/water (2:1, v/v) and cooling to 0° C. with stirring. The pH is adjusted to 10 with 0.1N NaOH and then 1.1 equivalents of di-tert-butyl dicarbonate (in dioxane) are added. The reaction is stirred at 0° C. to 20° C. for 4 hours and then is evaporated in vacuo. The residue is then partitioned between ethyl acetate/1% citric acid (2:1). The organic phase is isolated, extracted once with 1% citric acid, and then 3 times with saturated NaCl. The organic phase is dried over MgSO$_4$, filtered and concentrated in vacuo to obtain the BOC-protected product.

The resulting protected psuedopeptide free carboxylate is then coupled to the resin-bound hexadecapeptide using standard peptide synthesis techniques. This is followed by the sequential addition of BOC-D-Phe and BOC-Pro to the resin-bound peptide. The completed Hirulog-26 is then cleaved from the resin, deprotected and purified as described in Example 4.

EXAMPLE 26

Synthesis Of Hirulog-27

Hirulog-27 has the formula H-(D-Phe)-Pro-Arg-(CO-CH$_2$)-Pro-(Gly)$_4$-Asn-Gly-Asp-Phe-Glu-Glu-Ile-Pro-Glu-Glu-Tyr-Leu-OH. The (Gly)$_4$-Asn-Gly-Asp-Phe-Glu-Glu-Ile-Pro-Glu-Glu-Tyr-Leu hexadecapeptide was synthesized as previously described and left bound to the resin. The remaining portion of the molecule was synthesized by the reaction scheme depicted and described below.

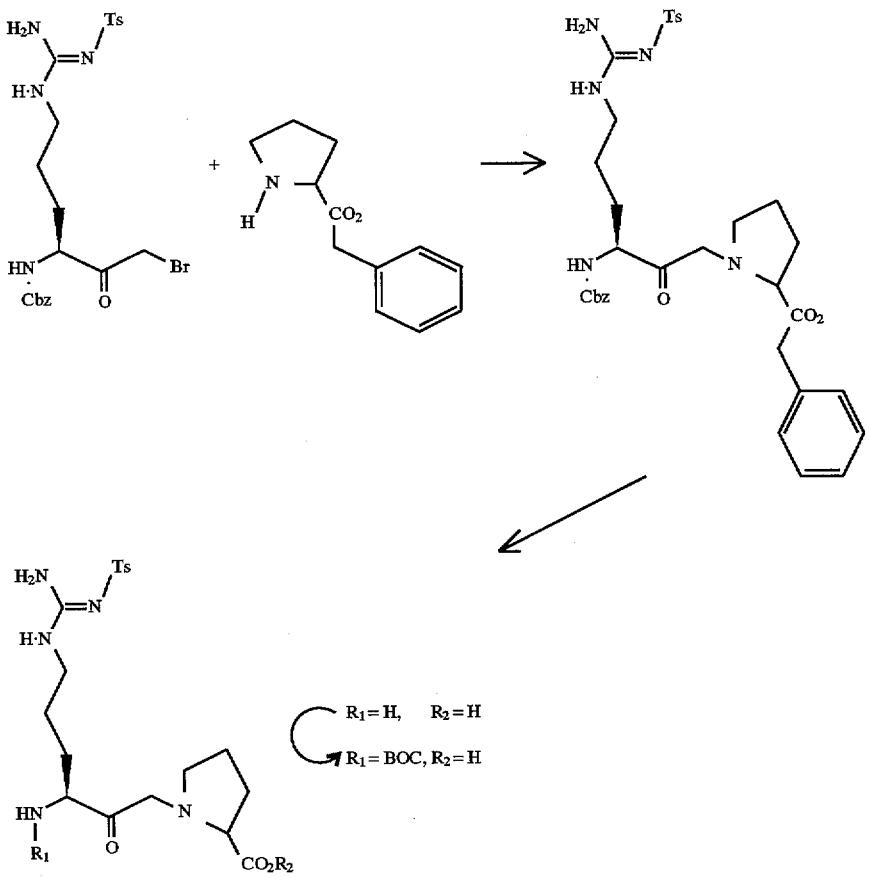

N$^\alpha$-Cbz-N$^g$-Tos-Arginine(COCH$_2$)proline Benzyl Ester

We dissolved 720 mg of proline benzyl ester (HCl salt) in 25 ml THF. This solution was then cooled to −78° C. in an acetone/dry ice bath with stirring under argon. We then added lithium diisopropylamide (8.0 ml of a 0.75M hexane suspension) and stirred for an additional 5 minutes. To this we added 1.08 g N$^\alpha$-Cbz-N$^g$-Tos-ArginineBromomethyl Ketone in 10 ml THF, prepared as described in Example 25, dropwise over 20 minutes. The reaction was stirred for an additional 5 minutes and the solution was then allowed to warm to room temperature with stirring. We quenched the reaction by adding 10 ml of saturated NaCl allowed the phases to separate and isolated the organic phase. This phase was then dried over MgSO$_4$, filtered and evaporated in vacuo.

N$^\alpha$-BOC-N$^g$-Tos-Arginine(OCCH$_2$)proline

The above benzyl ester (1.3 g) was hydrogenated using the palladium-carbon procedure described in Example 25. The resulting pseudodipeptide was BOC-protected by the procedure described in Example 25 to produce the desired product.

The purified, protected pseudodipeptide was then coupled with the resin-linked hexadecapeptide by standard peptide synthesis techniques. Hirulog-27 was deprotected, cleaved from the resin and purified by the techniques described in Example 4.

EXAMPLE 27

Synthesis Of Hirulog-28

Hirulog-28 has the formula: H-(D-Phe)-Pro-Arg(CH$_2$N)-Pro-(Gly)$_4$-Asn-Gly-Asp-Phe-Glu-Glu-Ile-Pro-Glu-Glu-Tyr-Leu-OH. The (Gly)$_4$-Asn-Gly-Asp-Phe-Glu-Glu-Ile-Pro-Glu-Glu-Tyr-Leu-O-PAM hexadecapeptide was synthesized as previously described and left bound to the resin. The remaining portion of the molecule was synthesized by the reaction scheme depicted and described below.

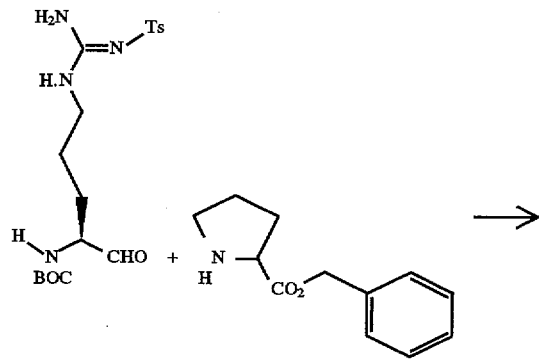

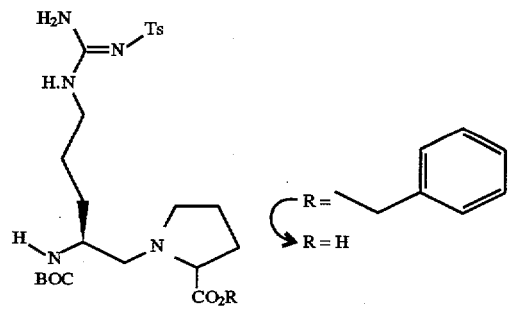

N$^\alpha$-BOC-N$^g$-Tos-Arginine[psiCH$_2$N]Proline Benxyl Ester

One gram of crushed 3 Å molecular sieves (Aldrich) was added to a stirred solution of 5.25 g proline benzyl ester free base (Schweizerhall, Inc.) in 10 ml anhydrous THF and 2 ml anhydrous ethanol under argon at room temperature. We added 1.45 ml of 5N methanolic HCl and 1.5 g of N$^\alpha$-BOC-N$^g$-Tos-Argininal (prepared as described in Example 22) to this mixture and stirred for 1 hour. An 85 mg portion of sodium cyanoborohydride was added to the mixture and then, an hour later, a second 85 mg portion of sodium cyanoborohydride was added. The reaction was then stirred for 20 hours and filtered. We added 1 ml water and 0.9 ml 1N HCl to the filtrate with stirring and then concentrated the solution in vacuo to yield 6.2 g of-N$^\alpha$-BOC-N$^g$-Arg[psiCH$_2$N]-Pro-benzyl ester, as a clear oil.

The oil is further purified by flash chromatography over a 5 cm flash column containing 350 ml silica gel (Merck Grade 60, 230–400 mesh, 60 Å). The product was obtained by succesive elution with 0.25%, 0.75% and 1.5% methanol in chloroform.

N$^\alpha$-BOC-N$^g$-Tos-Arginine[psi CH$_2$N]Proline

The resulting benzyl ester is hydrogenated over palladium-carbon and purified, as described in Example 25. This process yielded 160 mg of N$^\alpha$-BOC-N$^g$-Arg[psiCH$_2$N]-Proline free acid, which was further purified using the HPLC chromatography system described in Example 4, except elution was achieved with an isocratic 26% Buffer B/74% Buffer A system, previously described in Example 22. The final yield of dipeptide was 86 mg.

The dipeptide is then coupled to the resin-bound hexadecapeptide, followed by a cycle of BOC-Pro incorporation and a cycle of BOC-(D-Phe) incorporation. Deprotection, cleavage and purification of the fully synthesized Hirulog-28 is achieved by the method described in Example 4.

EXAMPLE 28

Synthesis Of Hirulog-29

Hirulog-29 has the formula: 4-chloro-isocoumarino-3-carboxyethoxy-(Gly)$_5$-Asn-Gly-AsP-Phe-Glu-Glu-Ile-Pro-Glu-Glu-Tyr-Leu-OH. The (Gly)$_5$-Asn-Gly-Asp-Phe-Glu-Glu-Ile-Pro-Glu-Glu-TYr-Leu heptadecapeptide was synthesized as previously described and left bound to the resin. The 4-chloro-isocoumarino-3-carboxyalkoxy moiety was synthesized by the reaction scheme and methods described below.

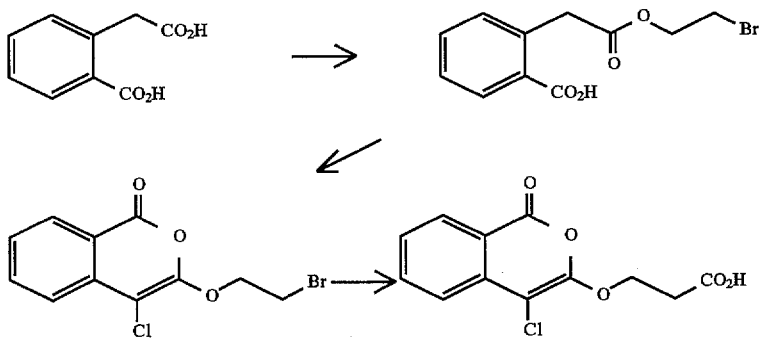

Ethyl 2-bromo-Homopthalate

We mixed homopthalic acid (10.0 g), 2-bromoethanol (21.0 g) and benzene (200 ml). We then added 12–15 drops of sulfuric acid and heated to reflux for 2.5 hours. The solution was then filtered and concentrated invacuo. The residue was washed with 50 ml ether/hexane (1:1) and was filtered onto a scintered glass funnel. The resulting light brown solid was vacuum dried to obtain approximately 15.0 g of product.

4-chloro-3-[2-bromoethyloxy]-isocoumarin

We mixed the ethyl 2-bromo homopthalate prepared as described above (4 g) together with phosphorous pentachloride (8.2 g) and benzene (100 ml). The mixture was refluxed for 4.5 hours, filtered hot and evaporated in vacuo. The reddish-brown oily residue was chromatographed immediately on a 24 mm×175 mm silica gel column using dichloromethane as eluant. Fractions of 20 ml were collected and assayed by TLC. The 4-chloro-3-[2-bromoethyloxy]-isocoumarin eluted in fractions 2–6. The fractions were pooled, evaporated invacuo and the resulting residue was recovered as a clear, light yellow oil (2.2 g).

4-chloro-3-[3-oxypropanoic acid]-isocoumarin

The 4-chloro-3-[2-bromoethyl]-isocoumarin (1.4 g) prepared above was dissolved in anhydrous THF and added directly to a refluxing solution of magnesium turnings (170 mg), and a few crystals of iodine in 15 ml anhydrous THF, which was stirring under argon. The mixture was refluxed for 1.5 hours. It was then poured over excess dry ice in a 400 ml beaker. We let the mixture stand at 20° until all the excess $CO_2$ had sublimed and then added approximately 100 ml each of diethyl ether and THF to the mixture which produced a yellow solution containing a large amount of white, coarse precipitate.

We bubbled anhydrous HCl through this mixture at 20°, which dissolved most of the precipitate. The solution was then filtered and evaporated in vacuo to obtain the crude product. This was then recrystallized overnight from DCM.

The resulting 4-chloro-3-[3-oxyproponoic acid]-isocoumarin is coupled to a glycine benzyl ester and the resulting product catalytically hydrogenated over palladium-carbon, as described in Example 25. This pseudodipeptide is then coupled to the resin-bound hexadecapeptide, $(Gly)_4$-Asn-Gly-Asp-Phe-Glu-Glu-Ile-Pro-Glu-Glu-Tyr-Leu, by standard peptide synthesis techniques.

EXAMPLE 29

Synthesis Of Hirulog-30

Hirulog-30 has the formula: 4-chloro-3-[2-aminoethanol]-isocoumarin-$(Gly)_5$-Asn-Gly-Asp-Phe-Glu-Glu-Ile-Pro-Glu-Glu-Tyr-Leu. The hexadecapeptide, $(Gly)_4$-Asn-Gly-Asp-Phe-Glu-Glu-Ile-Pro-Glu-Glu-Tyr-Leu is synthesized as previously described and left bound to the resin.

The 4-chloro-3-[2-aminoethanol]-isocoumarin moiety is prepared by a procedure analogous to that described in Example 28 for synthesizing 4-chloro-3-[2-bromoethanol]-isocoumarin, except that 2-aminoethanol is used instead of 2-bromoethanol in the initial step of esterifying homopthalic acid.

The urea linkage is formed by reacting the amino group of 4-chloro-3-[2-aminoethanol]-isocoumarin with the activating agent, carbonyldiimidazole ("CDI"). The resulting intermediate imidazolide is not isolated, but is reacted with the resin-linked hexadecapeptide to produce Hirulog-30. Hirulog-30 is then deprotected, cleaved from the resin and purified by the techniques described in Example 4.

EXAMPLE 30

Synthesis Of Hirulog-31

Hirulog-31 has the formula argipidyl-$(Gly)_5$-Asn-Gly-Asp-Phe-Glu-Glu-Ile-Pro-Glu-Glu-Tyr-Leu-OH. We synthesized the hexadecapeptide $(Gly)_4$-Asn-Gly-Asp-Phe-Glu-Glu-Ile-Pro-Glu-Glu-Tyr-Leu by the standard peptide synthesis techniques described previously and leave the peptide bound to the resin. The argipidylglycine portion of this Hirulog is synthesized by the reaction scheme depicted and described below.

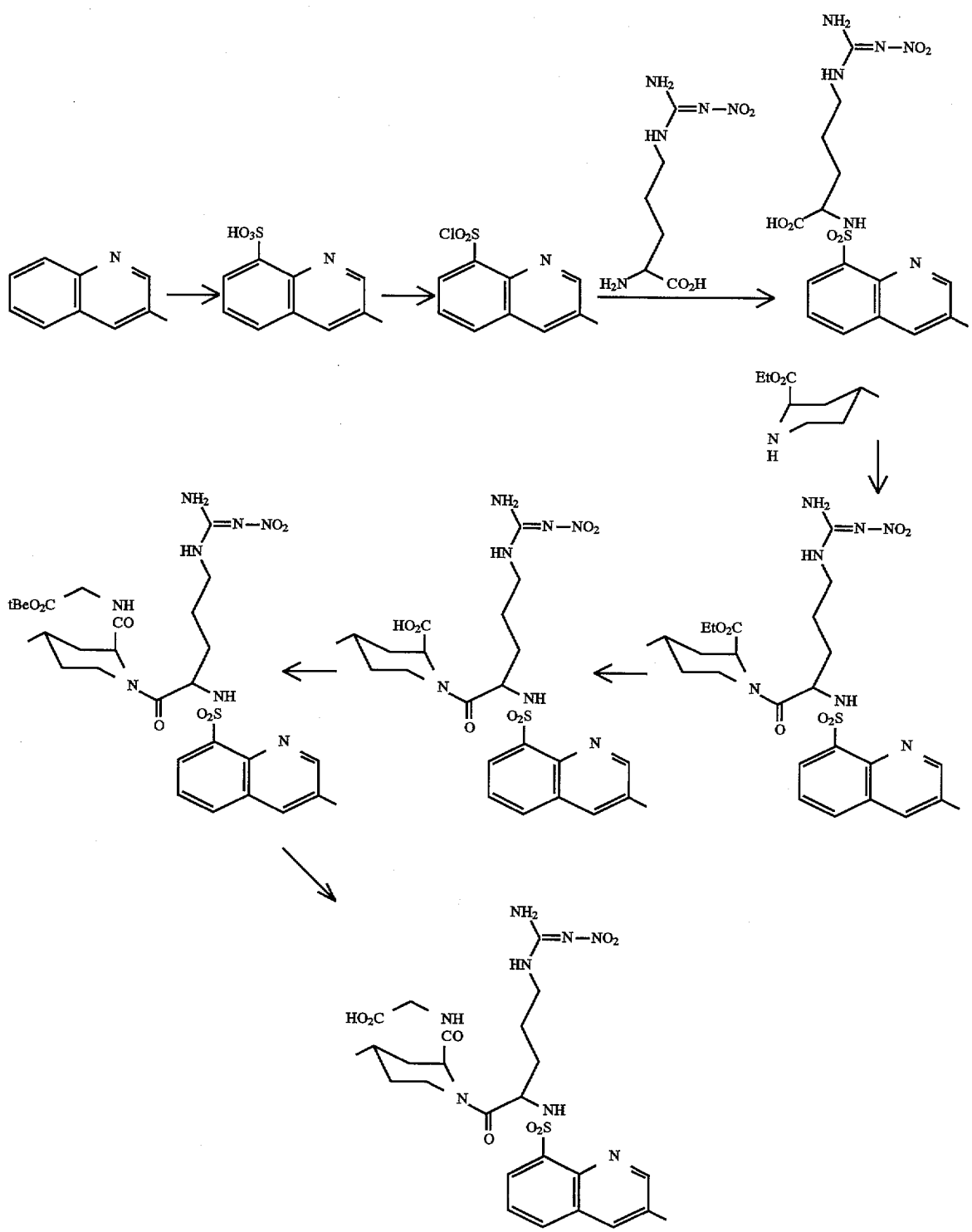

A Dehydro-$N^g$-NitroArgipidine is synthesized essentially by the method for synthesizing argipidine, which is described in U.S. Pat. No. 4,258,192, herein incorporated by reference. The only differences are that the guanidinium group is protected by a nitro function and the heterocyclic ring of the quinoline remains unsaturated. This intermediate is used to acylate t-butyl glycine by the method described in Example 21. The t-butyl ester is removed by standard acid hydrolysis techniques. The resulting free acid is reacted with the hexadecapeptide using standard coupling techniques. The resultant peptide is deprotected, cleaved from the resin and purified by the techniques described in Example 4.

The peptide is then subjected to the hydrogenation procedure described in the U.S. Pat. No. 4,258,192 and purified by the HPLC technique described in Example 4.

EXAMPLE 31

Synthesis Of Hirulog-32

Hirulog-32 has the formula: H-(D-Phe)-Pro-Arg-(Gly)$_5$-Asn-Gly-Asp-Phe-Glu-Glu-Ile-Pro-Glu-Glu-Tyr-Leu-OH. Hirulog-32 was synthesized, purified and characterized using the methods described in Example 4, except that BOC-glycine was used instead of BOC-proline in the cycle following the two cycles of BOC-glycylglycine addition.

EXAMPLE 32

Synthesis Of Hirulog-33

Hirulog-33 has the formula: N-acetyl-Gly-Asp-phe-Leu-Ala-Glu-(Gly)$_3$-Val-Arg-Pro-(Gly)$_4$-Asn-Gly-Asp-Phe-Glu-Glu-Ile-Pro-Glu-Glu-Tyr-Leu-OH. Hirulog-33 was synthesized, purified and characterized by the standard peptide synthesis techniques employed in Example 4, with appropriate BOC-amino acid substitutions. The CSDM portion of Hirulog-33 has an amino acid sequence that is identical to a segment of the fibrinopeptide A sequence of the Aα chain in human fibrinogen.

EXAMPLE 33

Cleavage Of Various Hirulogs By Thrombin

Inhibition of thrombin by Hirulog-8 was found to be transient due to the slow cleavage of the Arg-Pro bond by thrombin. Following this cleavage, thrombin was observed to recover full hydrolytic activity toward a chromogenic substrate. Therefore, Hirulog-8 was characterized as a "slow-substrate" inhibitor of thrombin.

The cleavage of Hirulog-8, as well as other Hirulogs of this invention, by human α-thrombin was demonstrated in in vitro assays. Reaction mixtures containing human α-thrombin (1.6 nM) and varying concentrations of either Hirulog-8, Hirulog-10, Hirulog-18a, Hirulog-18b, Hirulog-18c, Hirulog-19, Hirulog-32 or Hirulog-33 (80 to 160 nM) were prepared in 20 mM Tris-HCl pH 7.4 containing 0.1M NaCl. Aliquots (0.975 ml) of the reaction mixtures were removed at various times and mixed in a cuvette with 0.025 ml Spectrozyme TH (11 μM final concentration), a chromogenic substrate. The initial rate of reaction was determined and, based on control mixtures containing thrombin in the absence of Hirulog, the % inhibition was calculated.

An alternate method employed reverse-phase HPLC separation of aliquots from a Hirulog/thrombin reaction mixture. In this assay we added human α-thrombin (0.25 μM final concentrations) to a reaction vessel containing one of the above Hirulogs (12.5 μM final concentration). Aliquots (50 μl) were removed both prior to and at various times following the addition of thrombin. The aliquots were either flash frozen of injected directly onto the HPLC column. The HPLC system employed an Applied Biosystems Liquid Chromatography System equipped with an Aquapore C$_8$ column (0.46×10 cm). The column was equilibrated in 70% solvent A (0.1% TFA in water) and 30% solvent B (0.085% TFA/70% acetonitrile) and developed with a linear gradient of from 30 to 50% solvent B over 30 minutes at a flow rate of 1 ml/minute. The effluent stream was monitored at 214 nm. Peptide concentrations were determined by measurement of peak heights.

Both of the above-described assays allow determination of the rate of Hirulog hydrolysis by thrombin (expressed in M/min) and turnover rate ($k_{cat}$; expressed in min$^{-1}$). Both methods produced comparable $k_{cat}$ values, which are shown in the table below.

| INHIBITOR | $P_1$-$P_1'$ SEQUENCE | $k_{cat}$ (min$^{-1}$) |
| --- | --- | --- |
| Hirulog-8 | Arg—Pro | 0.31–0.5 |
| Hirulog-10 | Arg—Sar | 10 |
| Hirulog-18a | β-HomoArg—Gly | <0.01 |
| Hirulog-18b | β-HomoArg—Pro | <0.01 |
| Hirulog-18c | β-HomoArg—Val | <0.01 |
| Hirulog-19 | Arg[psiCH$_2$NH]—Gly | <0.01 |
| Hirulog-32 | Arg—Gly | 535 |
| Hirulog-33 | Arg—Pro | 0.056 |

As shown above, Hirulog-8, -10, -32 and -33 were cleaved by thrombin with $k_{cat}$ values ranging from 0.056 min$^{-1}$ (slow cleavage) to 535 min$^{-1}$(fast cleavage). In contrast, Hirulog-18a, -18b, -18c, and -19 appear to be resistant to thrombin cleavage.

Figure 5A:
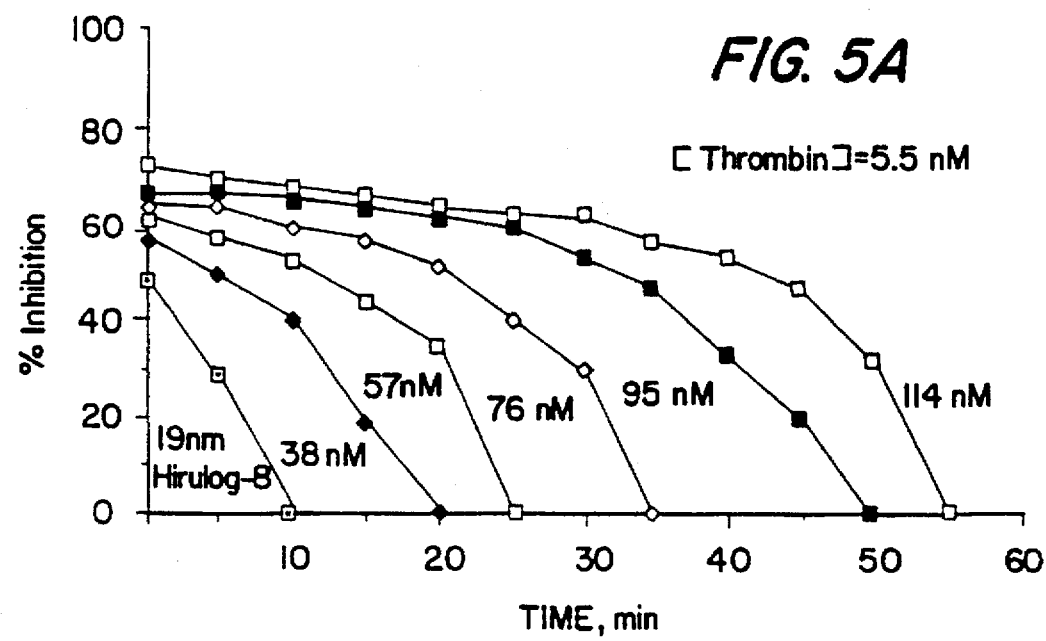
FIG. 5A, depicts the time course for cleavage of varying concentrations of Hirulog-8 by human α-thrombin.
Figure 5B:
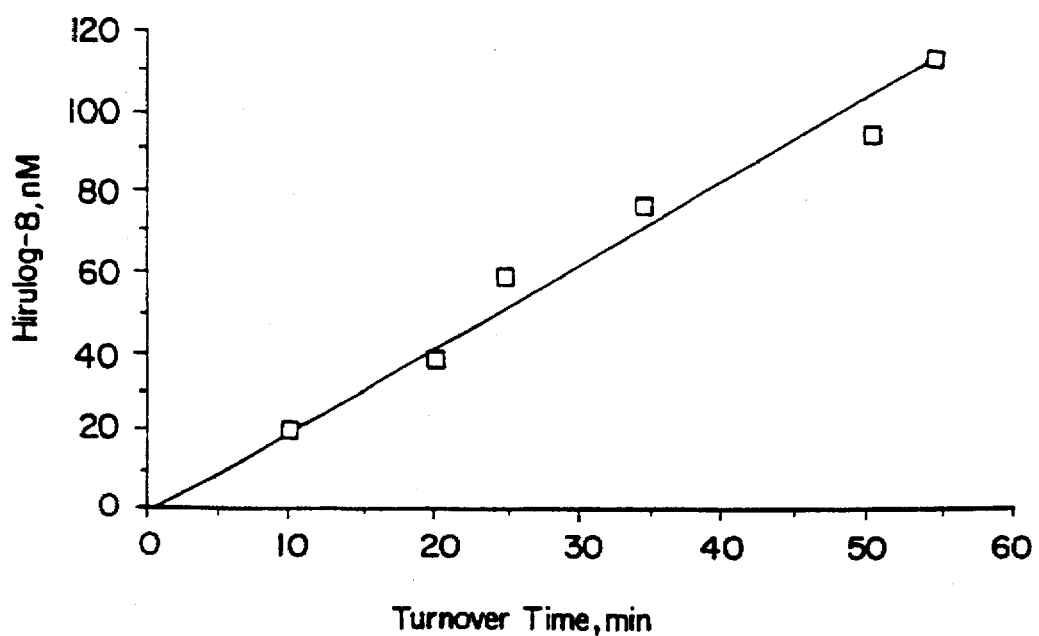
FIG. 5B, depicts the relationship between Hirulog-8 concentration and the duration of inhibition of Spectrozyme TH hydrolysis by human α-thrombin.

FIGS. 5, A and B, show a more detailed analysis of the cleavage of Hirulog-8 by thrombin. As depicted in FIG. 5, panel A, concentrations of Hirulog-8 in slight excess over thrombin exhibited a transient inhibitory activity (greater than, or equal to, 10 minutes, depending on the Hirulog concentration). Progressively higher concentrations of Hirulog-8 demonstrated prolonged inhibitory effects. A linear relationship between duration of inhibition and Hirulog-8 concentration is shown in FIG. 5, panel B. From these data, we calculated a turnover time, or $k_{cat}$, of 0.37 min$^{-1}$.

By purification and sequence analysis of the Hirulog-8-derived digestion products produced in the reactions above, we determined that Hirulog-8 was slowly cleaved by thrombin at the Arg-Pro bond. This is a highly unusual cleavage site for serine proteases and we believe it to be susceptible to cleavage in Hirulog-8 due to the high affinity of the peptide for thrombin.

EXAMPLE 34

The Effect Of Linker Length On The Activity Of Hirulog

Hirulog-8, Hirulog-13, Hirulog-15, and Hirulog-16 differ from one another only by the length of the polyglycine portion of their respective linker segments. In order to determine what effect linker length has on activity, we compared the inhibition of human α-thrombin by each of these Hirulogs. The following table lists the linker lengths of each of these Hirulogs:

| Peptide | Linker Length (Å) |
| --- | --- |
| Hirulog-8 | 24 |
| Hirulog-13 | 18 |
| Hirulog-15 | 30 |
| Hirulog-16 | 36 |

Figure 6:
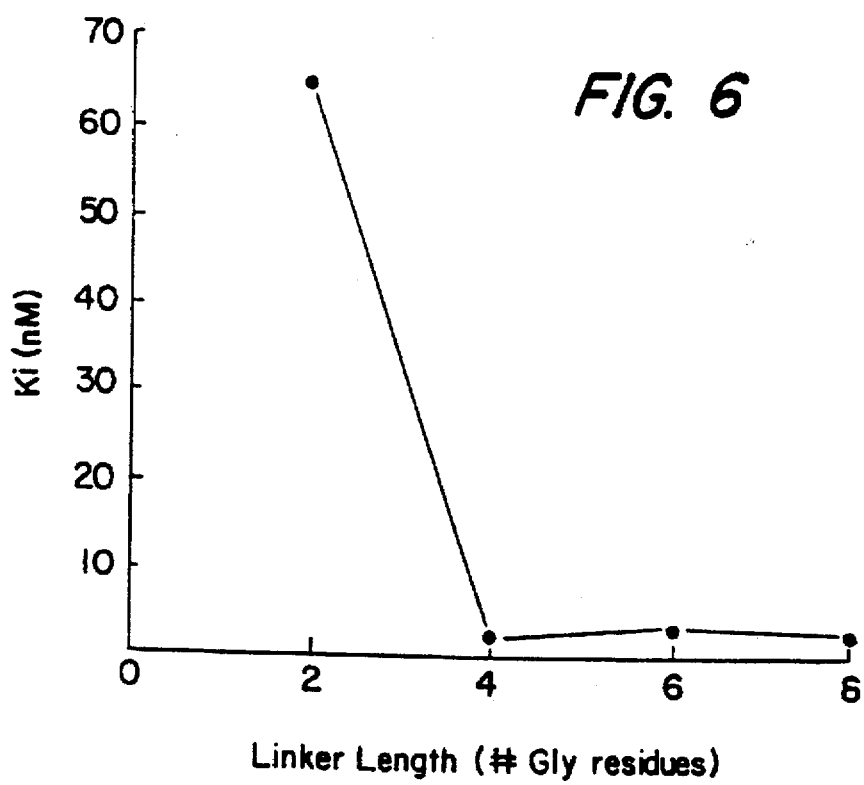
FIG. 6 depicts the effect of linker length of the thrombin inhibitors of this invention on the inhibition of thrombin-catalyzed hydrolysis of Spectrozyme TH.

The antithrombin activities of these Hirulogs was measured toward thrombin-catalyzed hydrolysis of Spectrozyme TH essentially as described in Example 9. FIG. 6 depicts the relationship of linker length to $K_i$ for Hirulog inhibition of this thrombin-catalyzed reaction. This figure shows that Hirulogs-8, -15 and -16 have comparable inhibitory activities, while Hirulog-13, with an 18 Å linker length, has an activity reduced by more than 10-fold. This confirms that linker lengths of >18 Å and <42 Å do not affect Hirulog activity. While not wishing to be bound by theory, applicants believe this is due to the fact that the Hirulog linker is equally disordered when free in solution as when bound to thrombin. Applicants also believe that there is little cooperativity in the binding of the CSDM and ABEAM portions of the thrombin inhibitors of this invention to thrombin.

EXAMPLE 35

Inhibition Of Thrombin-Catalyzed Hydrolysis By Various Hirulogs

We compared the inhibitory activity of various thrombin inhibitors of the present invention on thrombin-catalyzed hydrolysis of a tripeptidyl-p-nitroanilide substrate. The antithrombin activities of Hirulog-10, Hirulog-18a, Hirulog-18b, Hirulog-18c, Hirulog-19, Hirulog-32 and Hirulog-33 were assayed by the method described in Example 9, using Spectrozyme TH as a substrate. The table below lists the calculated $K_i$ values as well as the $P_1$-$P_1'$ sequence, of each of these thrombin inhibitors.

| INHIBITOR | $P_1$-$P_1'$ SEQUENCE | $K_i$ (nM) |
|---|---|---|
| Hirulog-8 | Arg—Pro | 1.9 ± 1.4 |
| Hirulog-10 | Arg—Sar | >2,000.0 |
| Hirulog-18a | β-HomoArg—Gly | 7.4 |
| Hirulog-18b | β-HomoArg—Pro | 4.6 |
| Hirulog-18c | β-HomoArg—Val | 205.0 |
| Hirulog-19 | Arg[psiCH$_2$NH]—Gly | 20.0 |
| Hirulog-32 | Arg—Gly | >2,000 |
| Hirulog-33 | Arg—Pro | 3.6 |

As indicated above, Hirulog-10 and Hirulog-32 were poor inhibitors of thrombin-catalyzed hydrolysis of Spectrozyme TH. This was consistent with the fact that each of these inhibitors was rapidly cleaved by thrombin at the $P_1$-$P_1'$ bond. In Hirulog-19, wherein this bond was reduced to the psiCH$_2$-NH linkage and rendered non-cleavable by thrombin, effective inhibition of thrombin hydrolysis was observed.

The studies with β-homoarginine-containing inhibitors (Hirulogs-18a, -18b and -18c) demonstrated that this amino acid derivative may replace arginine in the inhibitors of this invention without affecting activity. Moreover, this shows that displacement of the amide bond by one methylene does not markedly reduce thrombin inhibitory activity. The 30- to 50-fold increase in $K_i$ for Hirulog-18c, as compared to Hirulog-18a and -18b, respectively, suggests that the structure of the $P_1'$ amino acid is important in inhibitory activity. Without wishing to be bound by theory, applicants believe that the presence of phi-psi angles in the $P_1'$ amino acid (Gly in Hirulog-18a; Pro in Hirulog-18b) as well as conformational constraints, (such as is caused by the proline in Hirulog-18b) contribute to the potency of the inhibitors of this invention. An alternate possibility is that the β-branched side chain of the $P_1'$ amino acid Val in Hirulog-18c may impair binding of the CSDM portion of that molecule to the thrombin reactive center due to steric considerations.

EXAMPLE 36

Binding Of Hirulog-8 To The Active Site Of Thrombin

Figure 7:
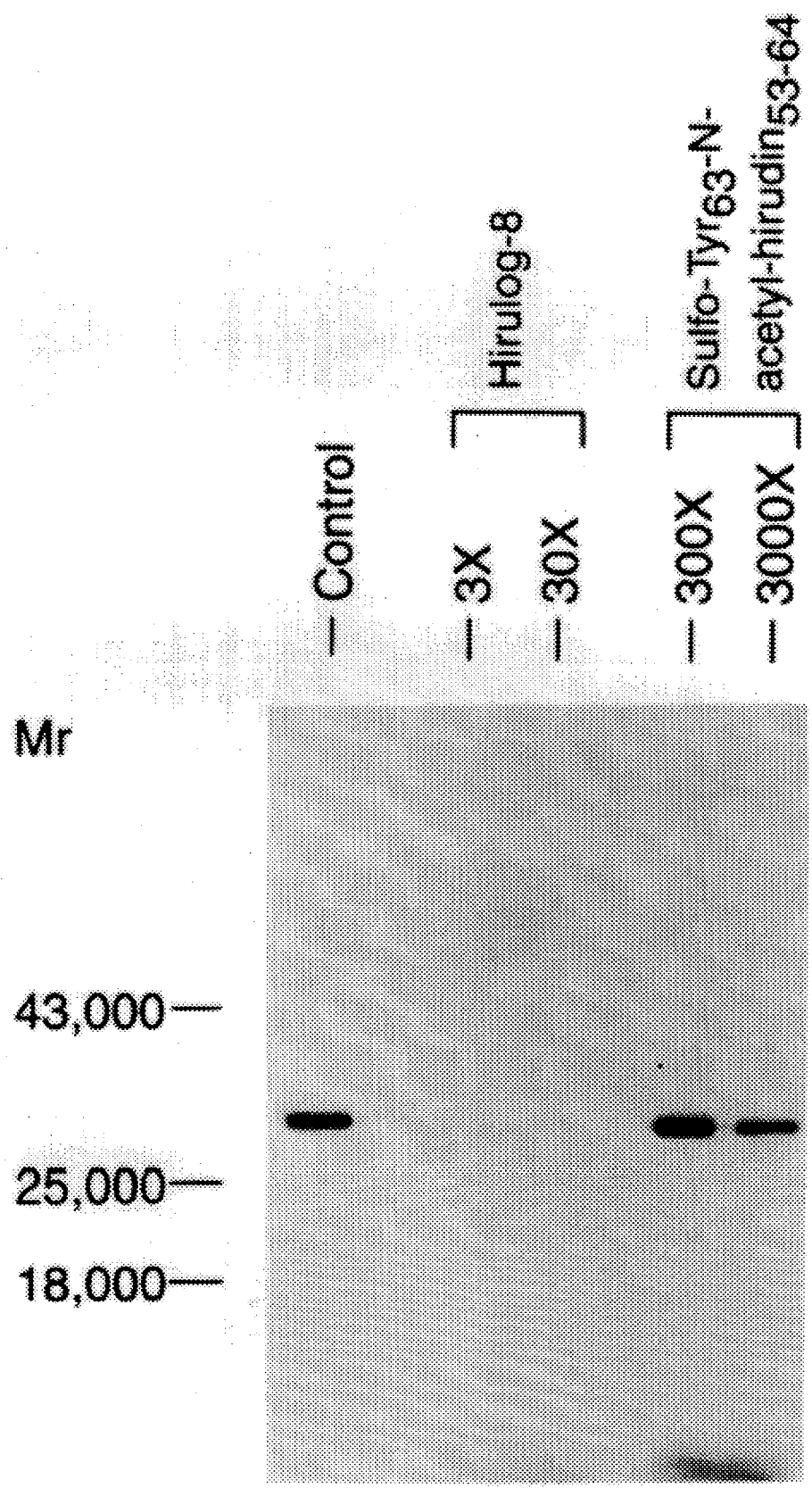
FIG. 7 depicts the inhibitory effects of varying concentrations of Hirulog-8 or Sulfo-$Tyr_{63}$-N-acetyl-$hirudin_{53-64}$ on the modification of thrombin by $^{14}$C-DFP.

Diisopropylfluorophosphate (DFP) is a well-known inhibitor of serine proteases, including thrombin, which acts by covalently modifying the hydroxyl group of Ser-195. We added a 270-fold excess of $^{14}$C-DFP to thrombin, in 0.1M sodium borate, pH 8.0. Following a 10 minute reaction, formation of a thrombin complex was demonstrated by SDS-PAGE and fluorographic analyses (FIG. 7, lane 1). When the reaction was performed in the presence of Sulfo-Tyr$_{63}$-N-acetyl-hirudin$_{54-64}$ (at 300 and 3000-fold molar excess over thrombin), the modification of thrombin by [$^{14}$C]-DFP was not altered significantly (FIG. 7, lanes 4 and 5). However, when we performed the reaction in the presence of Hirulog-8 (at 3- or 30-fold molar excess over thrombin) the incorporation of [$^{14}$C]-DFP into the thrombin catalytic site was completely blocked (FIG. 7, lanes 2 and 3). These data demonstrate that the CSDM of the thrombin inhibitors of this invention are capable of binding to the catalytic site of thrombin and inhibiting catalytic activity.

EXAMPLE 37

Comparison Of Antithrombin Activity of Hirulog-8 And A Synthetic Catalytic Site Directed Pentapeptide (D-Phe-Pro-Arg-Pro-Gly)

As shown in FIG. 1, Hirulog-8, unlike its constituent anion-binding exosite associating moiety, Sulfo-Tyr$_{63}$-N-acetyl-hirudin$_{54-64}$, was able to inhibit thrombin-catalyzed hydrolysis of small p-nitroanilide substrates. Similarly, we have tested the ability of a (D-Phe)-Pro-Arg-Pro-Gly pentapeptide to inhibit thrombin catalytic reactivity.

The pentapeptide was synthesized as described in Example 4, using a BOC-glycine-divinylbenzene resin. The pentapeptide was purified and characterized as described in Example 4.

The effects of both Hirulog-8 and this pentapeptide toward thrombin-catalyzed hydrolysis of Spectrozyme TH were studied as described in Example 9, using fixed peptide concentrations of 50 nM or 10 μM, respectively. Our results show that while nanomolar concentrations of Hirulog-8 can inhibit the thrombin-catalyzed reaction, concentrations of pentapeptide as high as 10 μM have no significant effect on the thrombin-catalyzed rate. These data show that the CSDM component of the thrombin inhibitors of this invention is, by itself, only a weak inhibitor of thrombin's catalytic function.

EXAMPLE 38

In vivo Anticoagulant Activity Of Hirulog-8

Figure 8:
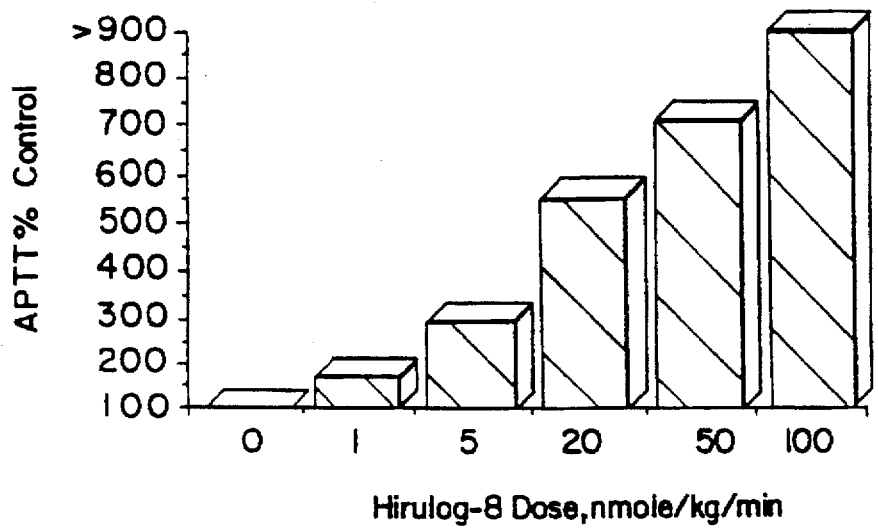
FIG. 8 depicts the in vivo effect of varying doses of Hirulog-8 on APTT in baboons.

We determined the in vivo anticoagulant activity of Hirulog-8 following intravenous administration of this peptide into baboons. We used various dosages of Hirulog-8 ranging from 0.002 to 0.2 mg/kg/min. Baboons (male, 10–15 kg) were sedated with ketamine hydrochloride prior to administration of Hirulog-8. Whole blood from treated and control animals was removed from a catheter placed in the femoral vein and collected into 3.8% sodium citrate (9:1; blood:sodium citrate). Plasma was obtained by standard methods and the APTT was recorded by methods described in Example 10. As shown in FIG. 8, Hirulog-8 yielded a dose-dependent increase in the APTT. A 200% increase in the APTT (considered a therapeutic range) was achieved with the lowest Hirulog dose (0.002 mg/kg/min. infusion).

EXAMPLE 39

Inhibition Of Clot-Bound Thrombin By Hirulog-8

It is known that thrombin can bind to a fibrin clot and, once absorbed, continue to cleave additional fibrinogen, resulting in growth of the clot. Clot-bound thrombin has been shown to be resistant to neutralization by the heparin-anti-thrombin III complex [P. J. Hogg et al., "Fibrin Monomer Protects Thrombin From Inactivation By Heparin-Antithrombin III: Implications for Heparin Efficacy", *Proc. Natl. Acad. Sci. USA*, 86, pp. 3619–23 (1989)], but may be inhibited by antithrombin III-independent inhibitors, such as PPACK, hirudin or Sulfo-Tyr$_{63}$-N-acetyl-hirudin$_{54-64}$. Clot-bound thrombin is believed to play a role in thrombus accretion and in rethrombosis following thrombolytic therapy.

We compared the abilities of Hirulog-8 and heparin to inhibit clot-bound thrombin using the method described by J. I. Weitz et al., "Clot-Bound Thrombin Is Protected from Heparin Inhibition—A Potential Mechanism for Rethrombosis After Lytic Therapy", *Blood*, 74, p. 136a, (1989).

Figure 9:
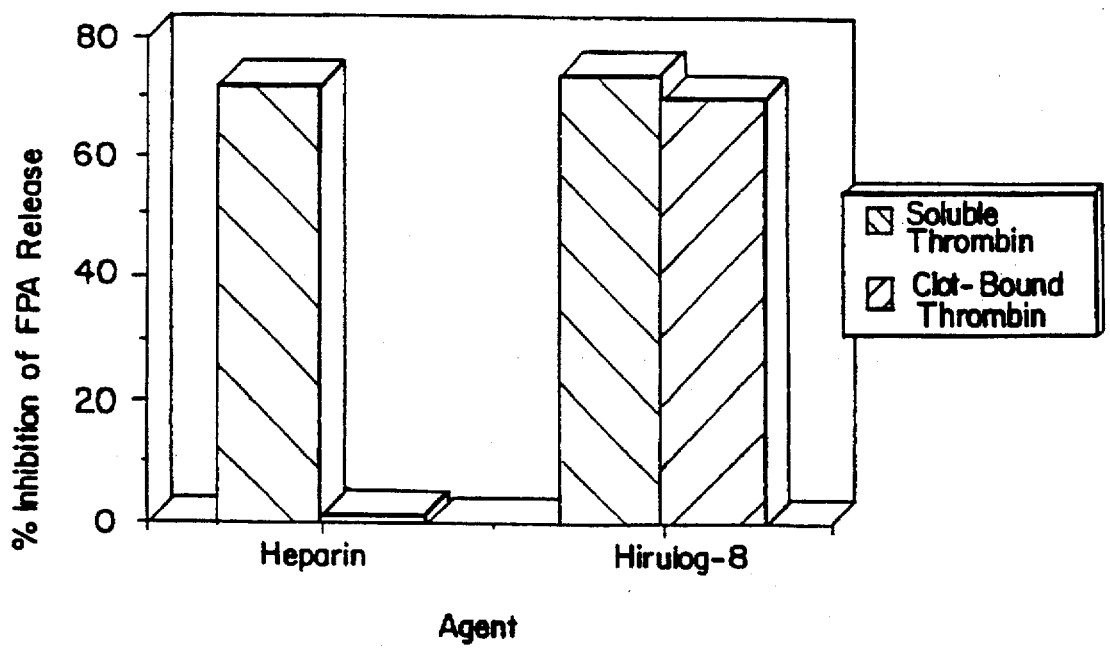
FIG. 9 depicts the comparative inhibitory effects of Hirulog-8 or heparin on the hydrolysis of fibrinogen by soluble or clot-bound thrombin.

A clinically relevant dose of heparin (0.1 U/ml) inhibited fibrinopeptide A (FPA) release catalyzed by soluble thrombin by approximately 70%. However, a similar dose had no effect on FPA release catalyzed by clot-bound thrombin. In contrast, Hirulog-8 had an almost identical inhibitory effect on FPA release catalyzed by either soluble or clot-bound thrombin (FIG. 9).

This study indicated that Hirulog-8, as well as the other thrombin inhibitors of this invention, are more effective than current drugs in blocking thrombus accretion, increasing the rate of thrombolytic reperfusion and preventing rethrombosis following thrombolytic treatment.

EXAMPLE 40

The Effect Of Hirulog-8 On In Vivo Platelet-Dependent Thrombosis

Because baboons are known to have similar coagulation and hemostatic responses as man, we utilized a baboon model to determine the ability of Hirulog-8 to interrupt platelet-dependent thrombosis. Specifically, we placed various thrombogenic surfaces in a chronic exteriorized AV shunt in the animals. These surfaces included segments of endarterectomized baboon aorta, collagen-coated silastic tubing, collagen-coated Gortex and Dacron vascular graft. Following placement in the shunt, the surfaces were exposed to native flowing blood to elicit thrombus formation. We measured the formation of thrombi over a period of 60 minutes by monitoring the deposition of platelets on the thrombogenic surface. These measurements were recorded by external gamma-camera imaging following pre-infusion of the test animal with autologous $^{111}$In-labeled platelets.

Figure 10:
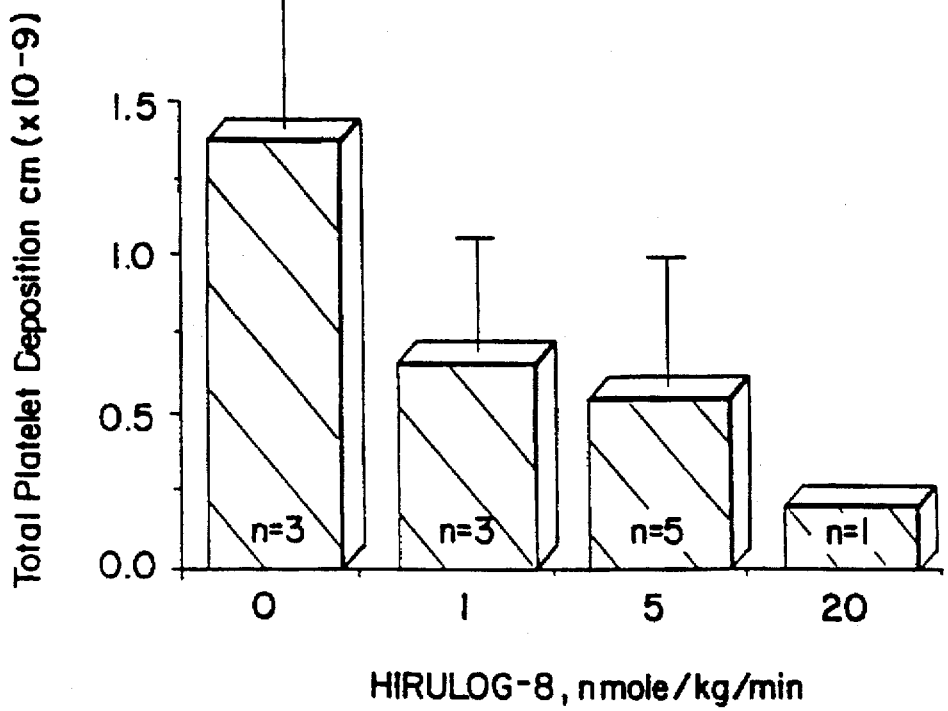
FIG. 10 depicts the in vivo effects of varying doses of Hirulog-8 on platelet deposition on an endarterectomized segment of baboon aorta.

Placement of a 5 cm segment of endarterectomized baboon aorta in the exteriorized AV shunt in the absence of Hirulog-8 led to a time-dependent deposition of platelets. This accumulation reached a plateau in 60 minutes, at which time a total of $14.0 \times 5.0 \times 10^8$ platelets/cm were found deposited on the endarterectomized segment. Doses of 0.002 and 0.01 mg/kg/min of Hirulog-8 inhibited platelet deposition by 53.6% and 75.5%, respectively. These results are depicted in FIG. 10. The ED$_{50}$ for Hirulog-8 (the dosage required to reduce platelet deposition by 50%) in this model system was 0.002 mg/kg/min.

Figure 11:
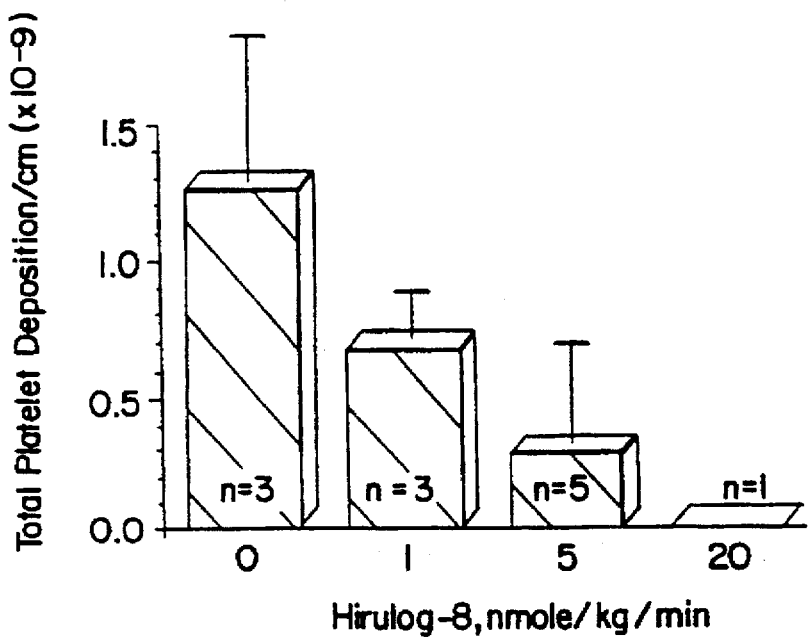
FIG. 11 depicts the in vivo effects of varying doses of Hirulog-8 on platelet deposition on a segment of collagen-coated tubing inserted into a baboon.

When we placed 5 cm segments of collagen-coated silastic tubing in the AV shunt, $12.6 \pm 5.0 \times 10^8$ platelets/cm were deposited after 60 minutes in the absence of Hirulog-8. Administration of Hirulog-8 resulted in a dose-dependent inhibition of platelet deposition. A dosage of 0.04 mg/kg/min Hirulog-8 completely inhibited platelet deposition. The results of this portion of the experiment are depicted in FIG. 11. The ED$_{50}$ of Hirulog-8 in this system was calculated to be 0.004 mg/kg/min.

Both collagen-coated Gortex or Dacron vascular grafts are known to be more thrombogenic than silastic tubing. A total of $35.0 \pm 6.0 \times 10^8$ platelets/cm were deposited on the Gortex following a 60 minute exposure to native blood in the absence of Hirulog-8. We found that Hirulog-8 once again demonstrated a dose-dependent antithrombotic effect towards platelet thrombus formation. A dose of 0.2 mg/kg/min Hirulog-8 caused a 62.9% inhibition of platelet deposition. The ED$_{50}$ for Hirulog-8 in the Gortex system was 0.135 mg/kg/min. A similar result was obtained for Dacron grafts. The higher dosage of Hirulog-8 required to inhibit platelet deposition on these two surfaces was to be expected because of their high thrombogenic activity.

We also determined the effect of Hirulog-8 toward both high and low shear platelet-dependent thrombus formation using a dual-chamber device, which allowed for simultaneous measurements of both shear conditions. The device was comprised of a 2 cm segment of collagen-coated Gortex followed by 2 cm segments of expanded diameter. Using this device, thrombus formation was initiated by exposure of native flowing blood to a segment of the collagen-coated Gortex at high shear. This part of the experimental protocol simulated arterial-like conditions. When the blood entered the expanded diameter segments, low-shear, vortex conditions were maintained, thereby simulating venous thrombosis. In control animals, a total of $9.3 \pm 2.3 \times 10^8$ and $6.1 \pm 0.5 \times 10^8$ platelets/cm accumulated after 40 minutes in the high and low shear segments, respectively. Hirulog-8 inhibited platelet deposition in both high and low shear segments in a dose-dependent fashion. A dose of 0.05 mg/kg/min inhibited platelet accumulation by 42.6% at low shear and by 29.0% at high shear.

EXAMPLE 41

Comparison Of Hirulog-8 With Other Anti-Thrombotic Agents In Inhibiting Acute Platelet-Dependent Thrombosis We examined the effects of heparin, low molecular-weight heparin and recombinant hirudin on platelet deposition in the collagen-coated silastic tubing/exteriorized AV shunt baboon model described in Example 40.

Figure 12:
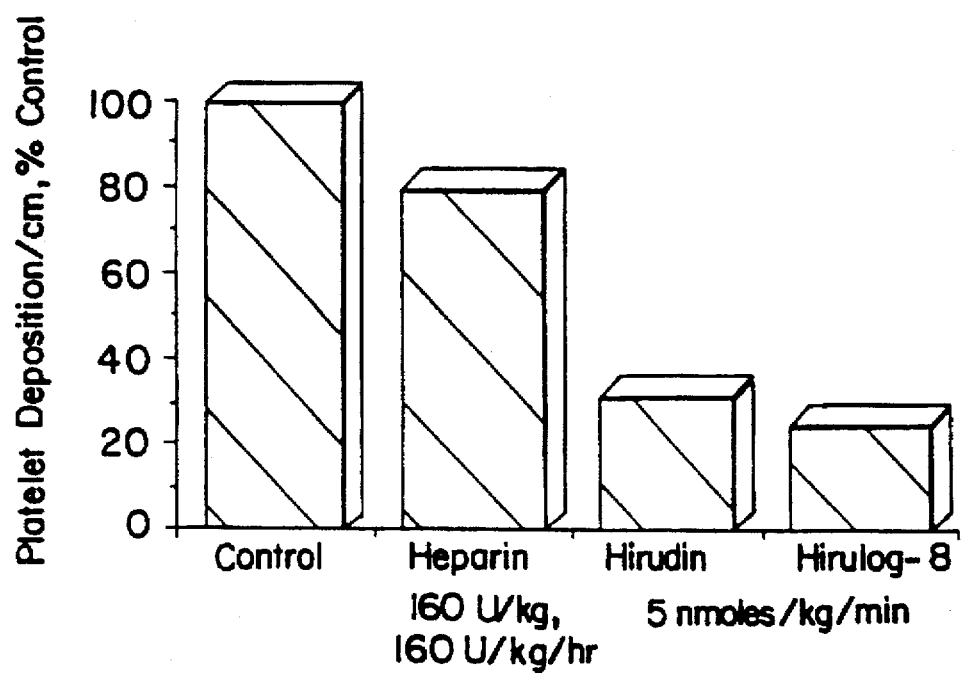
FIG. 12 depicts the comparative in vivo effects of heparin, hirudin and Hirulog-8 on platelet deposition on a segment of collagen-coated tubing inserted into a baboon AV shunt.

It has previously been shown that heparin administered as a 160 U/kg bolus injection followed by a 160 U/kg/hr infusion inhibited platelet deposition to a level of about 80% of that observed in a saline-treated control animal. Low molecular-weight heparin, given as a bolus injection of 53 anti-Xa U/kg, followed by infusion at 53 anti-Xa U/kg/hr, yielded similar results [Y. Cadroy, "In Vivo Mechanism of Thrombus Formation. Studies Using a Primate Model", *Doctoral Thesis*, L'Universite Paul Sabatier de Toulouse (Sciences) (1989)]. At equivalent molar doses (5 nmole/kg/min), recombinant hirudin [A. B. Kelly et al., "Recombinant Hirudin Interruption of Platelet-Dependent Thrombus Formation", *Circulation*, 78, p. II-311 (1988)] and Hirulog-8 both inhibited platelet-dependent thrombus formation by 60–70% as compared to the control. These results are depicted in FIG. 12. Other thrombin inhibitors have previously been tested in the baboon model [A. B. Kelley et al., "Comparison of Antithrombotic and Antihemostatic Effects Produced by Antithrombins in Primate Models of Arterial Thrombosis", *Thromb. and Hemostas.*, 62, p. 42 (1989)].

The reported $ED_{50}$ doses on collagen-coated surfaces for those agents, as well as our $ED_{50}$ determinations, are summarized in the table below:

| Agent | $ED_{50}$ |
|---|---|
| PPACK | 75 nmoles/kg/min |
| Gyki 14,451 | 500 |
| Benzamidine | 3000 |
| Argipidine (MD805) | 550 |
| rec-Hirudin | <5 |
| Hirulog-8 | <5 |

EXAMPLE 42

The Effect Of Hirulog-8 On Fibrin Deposition

We measured the effect of Hirulog-8 on the deposition of fibrin(ogen) in the thrombi formed in the endarterectomized aortic and collagen-coated silastic tubing segments model systems described in Example 40. Fibrin deposition was determined by measurement of $^{125}$I-fibrin(ogen) 30 days after completion of the $^{111}$In-platelet assay described above. This allowed the $^{111}$In label to decay to a non-interfering level.

Figure 13:
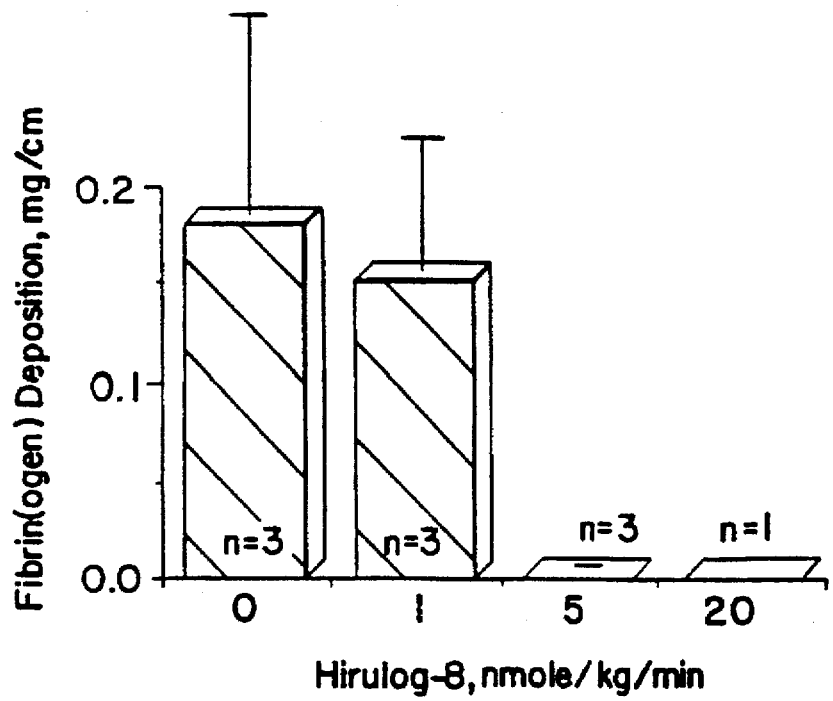
FIG. 13 depicts the in vivo effects of varying doses of Hirulog-8 on fibrin deposition on a segment of collagen-coated tubing inserted into a baboon AV shunt.

FIG. 13 demonstrates that in the absence of Hirulog-8, 0.17 mg/cm fibrin was deposited on the collagen-coated tubing following the 60 minute exposure to flowing blood described in Example 40. Doses of 0.01 and 0.04 mg/kg/min completely inhibited fibrin(ogen) deposition. Similar results were obtained with the endarterectomized aortic segment model. These results show that the thrombin inhibitors of this invention are effective in reducing fibrin(ogen) deposition associated with a thrombus, as well as blocking acute platelet-dependent thrombus formation.

EXAMPLE 43

Measurement Of Clearance Times For Hirulog-8

We used a baboon model to determine Hirulog-8 clearance times following intravenous infusion, single bolus intravenous injection and single bolus subcutaneous injection. APTT assays, performed as described in Example 11, were used to monitor clearance times.

We administered various dosages of Hirulog-8 (0.002–0.2 mg/kg/min) to baboons via systemic intravenous infusion, over a period of 60 minutes. APTT was measured following the 60 minute infusion and at various time intervals thereafter. We determined the average half-time for Hirulog-8 clearance to be 9.2±3.3 minutes.

Figure 14:
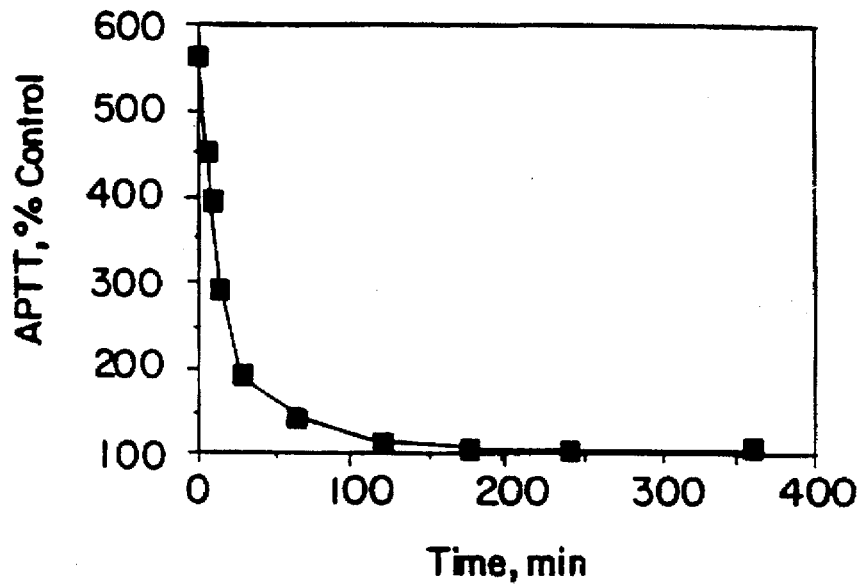
FIG. 14 depicts the change in APTT over time following intravenous bolus injection of baboons with Hirulog-8

To determine clearance time after a single bolus injection, we injected baboons with a dose of 1 mg/kg Hirulog-8 intravenously or subcutaneously. APTT measurements were taken at various time intervals following injection. FIG. 14 demonstrates that APTT increased to a peak of 570% of control value 2 minutes after intravenous injection. The half-life of Hirulog-8 following intravenous injection was 14 minutes.

Figure 15:
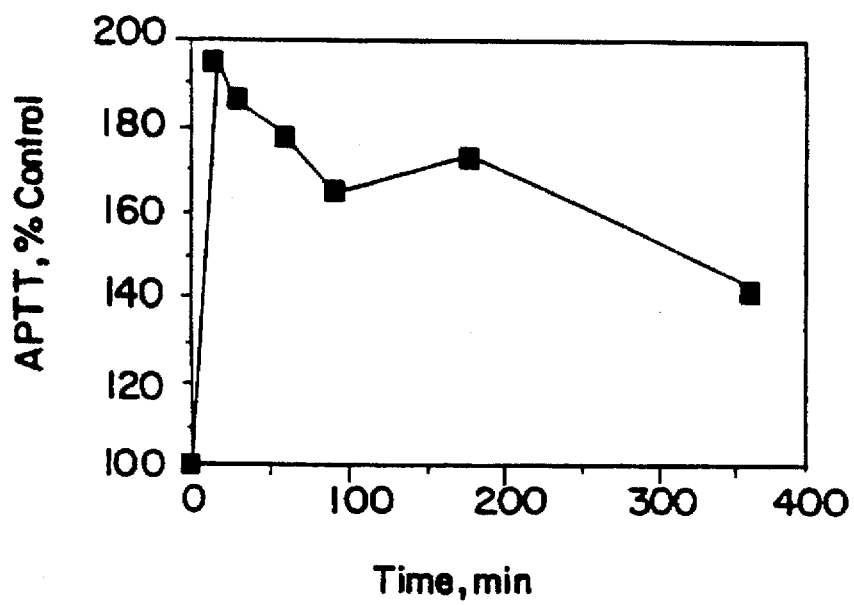
FIG. 15 depicts the change in APTT over time following subcutaneous injection of baboons with Hirulog-8.

FIG. 15 demonstrates that at the earliest time point following subcutaneous injection of Hirulog-8 (i.e. 15 minutes), APTT was increased to approximately 200% of control. Clearance via the subcutaneous route was prolonged to a half-time of 340 minutes. Hirulog-8 administered subcutaneously was found to be quantitatively adsorbed.

EXAMPLE 44

Effect Of Hirulog-8 In Baboon Models Of Disseminated Intravascular Coagulation

We induced septicemia in baboons by injection of a lethal dose of live *E. coli* according to the method described by F. B. Taylor et al. *J. Clin. Invest.*, 79, pp. 918–25 (1987). Hirulog-8 was infused at a dose of 0.08 mg/kg/hr from 15 minutes prior to the injection of *E. coli* to up to 6 hours following injection. In the absence of Hirulog-8, *E. coli*-induced septic shock led to a marked decline in neutrophil count, blood pressure and hematocrit. Control animals displayed a reduction in hematocrit to 70% of baseline and a drop in blood pressure to 20% of baseline after 3 hours. Administration of Hirulog-8 completely attenuated hematocrit drop and limited the peak drop in blood pressure to 60% of baseline.

Despite attenuation of DIC by Hirulog-8, the lethal infusion of *E. coli* still resulted in morbidity. An autopsy of both control and Hirulog-8-treated animals revealed massive tissue edema in both groups. However, only the control group displayed intravascular thrombosis. The results of the autopsies show that interruption of the coagulopathic stage of septicemia alone is not sufficient to prevent morbidity due to septic shock.

EXAMPLE 45

Effect Of A Combination Of tPA And Hirulog-8 On Thrombolysis

To determine the effect of Hirulog-8 on potentiating tPA-induced thrombolysis, we used a rat model for arterial thrombolysis. In this model, an experimental thrombus was formed in the abdominal aorta following balloon catheter denudation and high grade (95%) stenosis. Blood flow and blood pressure were recorded distal to the site of injury and stenosis. We randomized the rats to received tPA (1.0 mg/kg bolus followed by 1.0 mg/kg/hr infusion) together with one of the following: saline, heparin (10 U/kg bolus, followed by 1.5 U/kg/min infusion), recombinant hirudin (1.0 mg/kg bolus followed by 0.02 mg/kg/hr infusion) or Hirulog-8 (0.6 mg/kg bolus followed by 0.02 mg/kg/hr infusion). The antithrombotic agent or saline was administered concomitant with tPA and for an additional 50 minutes following the end of tPA infusion.

Figure 16:
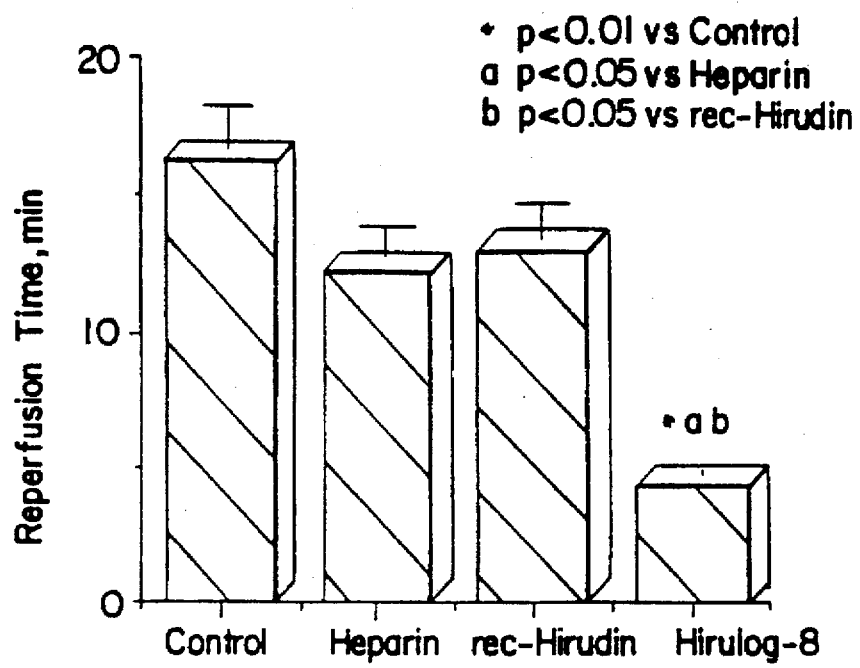
FIG. 16 depicts the comparative in vivo effects of tissue plasminogen activator together with either saline, heparin, hirudin or Hirulog-8 on reperfusion time in a rat model.

FIG. 16 depicts the results of these experiments. Animals treated with tPA+saline exhibited reperfusion times of 16.2 minutes. Heparin reduced reperfusion time to 12.2 minutes, while recombinant hirudin reduced it to 13.0 minutes. Neither of these decreases were statistically significant ($p<0.05$). The combination of Hirulog-8 with tPA significantly reduced reperfusion time to 4.4 minutes ($p<0.01$), thus accelerating the fibrinolytic effect of tPA by a factor of four.

Figure 17:
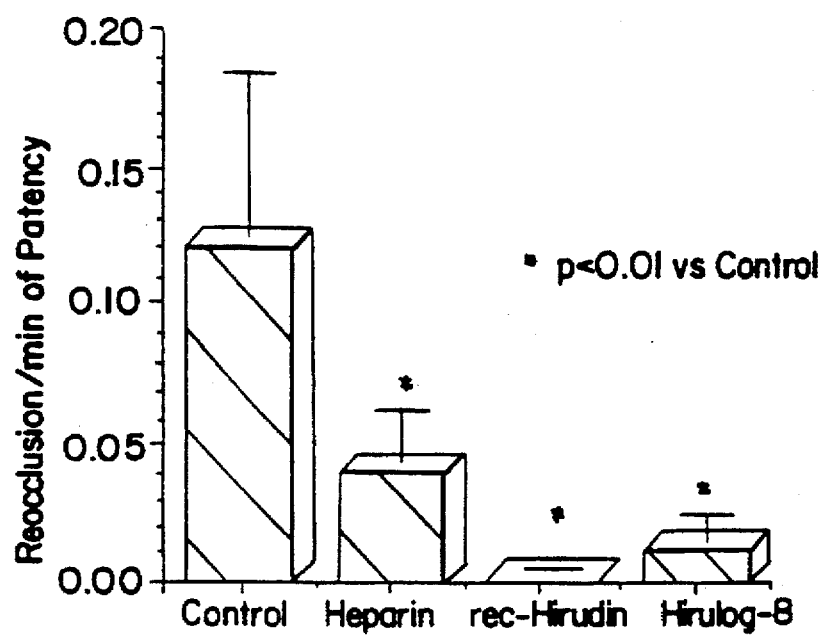
FIG. 17 depicts the comparative in vivo effects of tissue plasminogen activator together with either saline, heparin, hirudin or Hirulog-8 on reocclusion time in a rat model.
Figure 18:
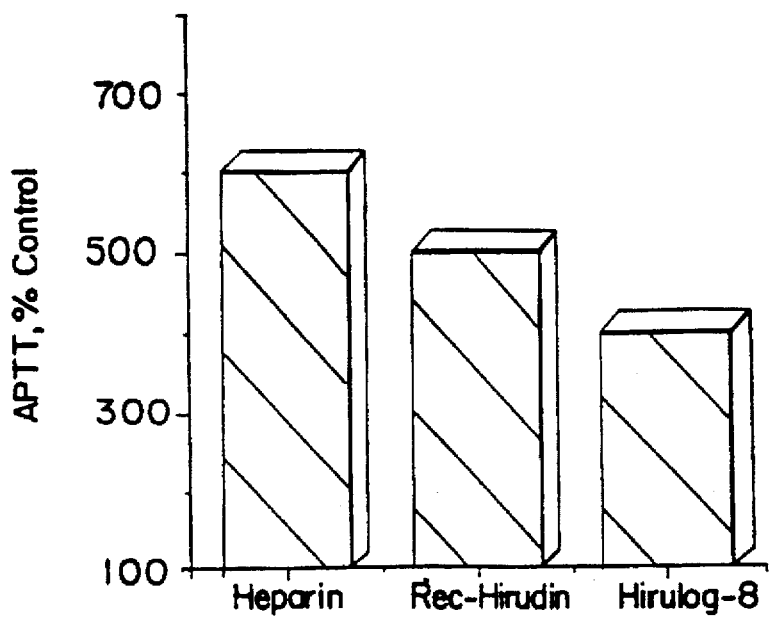
FIG. 18 depicts the comparative in vivo effects of tissue plasminogen activator together with either saline, heparin, hirudin or Hirulog-8 on APTT in a rat model.
Figure 19:
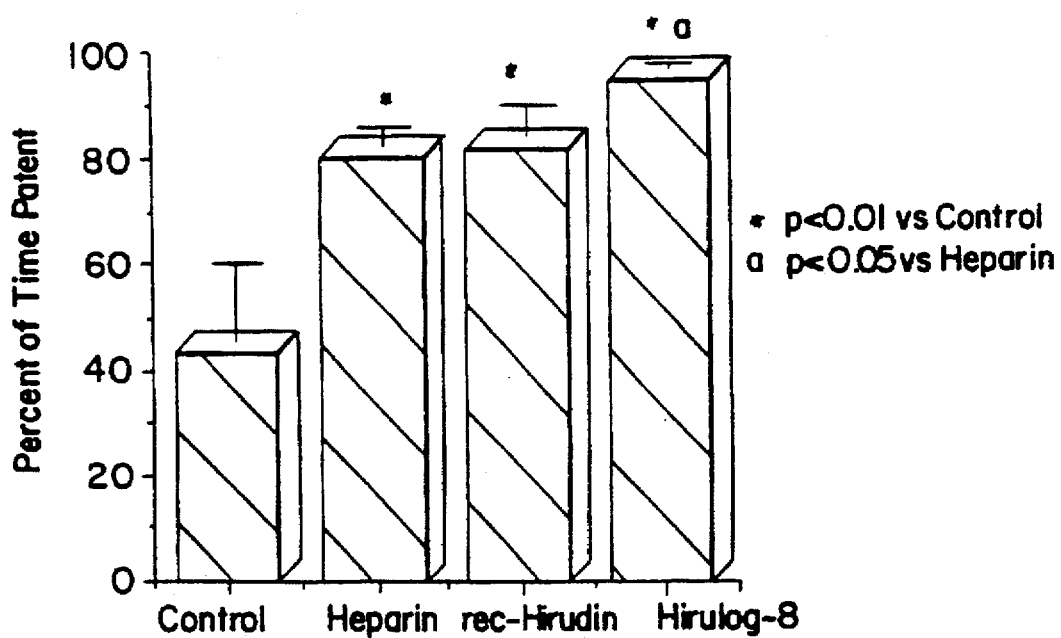
FIG. 19 depicts the comparative in vivo effects of tissue plasminogen activator together with either saline, heparin, hirudin or Hirulog-8 on vessel patency in a rat model.

Heparin, hirudin and Hirulog-8 all significantly prevented reocclusion as compared to saline-treated controls (FIG. 17). Each of these agents also prolonged APTT to values of 600%, 500% and 400%, respectively, over control values (FIG. 18). Finally, each of heparin, hirudin and Hirulog-8 increased the time of vessel patency to values of 80.2%, 82% and 93.1%, respectively (control=43.6%) (FIG. 19). These results demonstrate that the thrombin inhibitors of the present invention are superior to other known antithrombotics in increasing the efficacy of tPA.

EXAMPLE 46

Effect Of Hirulog-8 And Other Antithrombotic Agents On Bleeding Times In Baboons We employed the template bleeding time measurement to examine the effects of Hirulog-8 on hemostasis.

Figure 20:
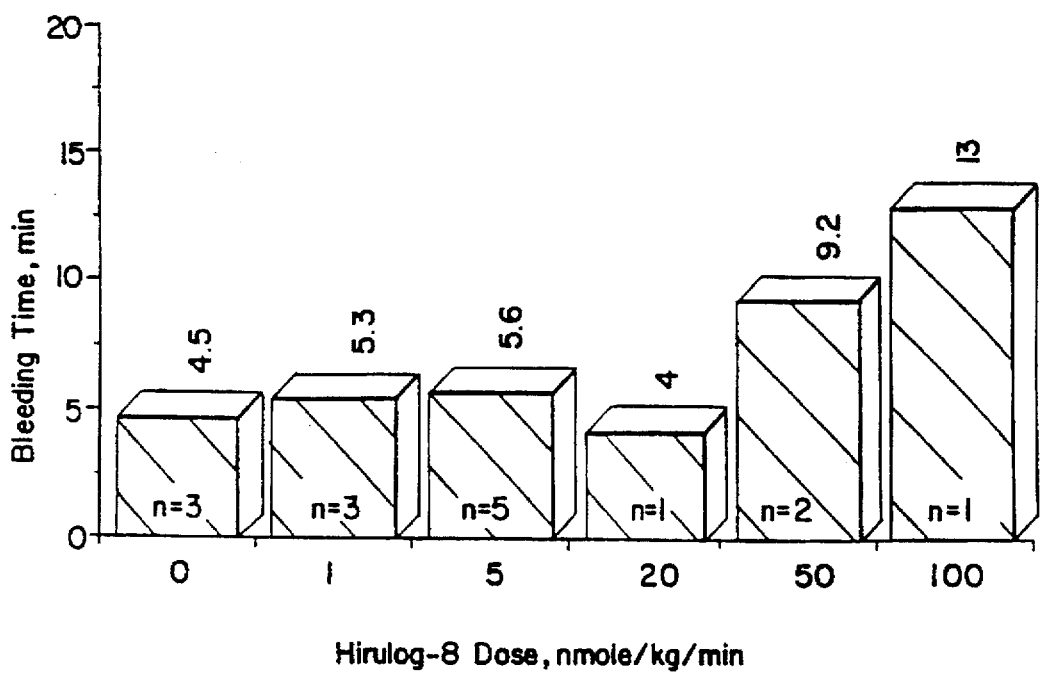
FIG. 20 depicts the effect of varying doses of Hirulog-8 on bleeding times in a baboon model.

Various dosages of Hirulog-8 (0.002 to 0.2 mg/kg/min) were analyzed for their effect on bleeding time. Doses of 0.002 to 0.04 mg/kg/min caused no significant increase in bleeding times. The results of this experiment are depicted in FIG. 20. At a dose of 0.1 mg/kg/min, Hirulog-8 causes a two-fold increase in bleeding time over control values. At 0.2 mg/kg/min Hirulog-8, bleeding times increased to 3 times control values. These results clearly demonstrate that dosages required to inhibit platelet-dependent thrombosis (0.002 mg/kg/min; see Example 40) do not cause a significant effect on hematostatic plug formation.

We also tested the effects of a variety of other agents on template bleeding time in the baboon, as well as on systemic anticoagulant effects (as measured by APTT). These results are summarized below:

| Agent | APTT (% control) | Bleeding Time (min) |
|---|---|---|
| Hirulog-8 | 300.6 | 5.5 |
| rec-hirudin | 393.9 | 12.1 |
| PPACK | 287.9 | 12 |
| Gyki 14,451 | 439.4 | 14 |
| Benzamidine | 757.6 | 10 |
| Argipidine (MD805) | >900 | >30 |
| Heparin | 706.1 | 10 |

EXAMPLE 47

Synthesis Of Hirulog-34

Hirulog-34 has the formula: H-(D-Phe)-Pro-Arg-(tetraethyleneglycolylsuccinyl)-Asn-Gly-Asp-Phe-Glu-Glu-Ile-Pro-Glu-Glu-Tyr-Leu-OH. The decapeptide Asn-Gly-Asp-Phe-Glu-Glu-Ile-Pro-Glu-Glu-Tyr-Leu is synthesized as previously described and left bound to the resin. The remaining portion of the molecule is synthesized by the reaction scheme depicted and described below:

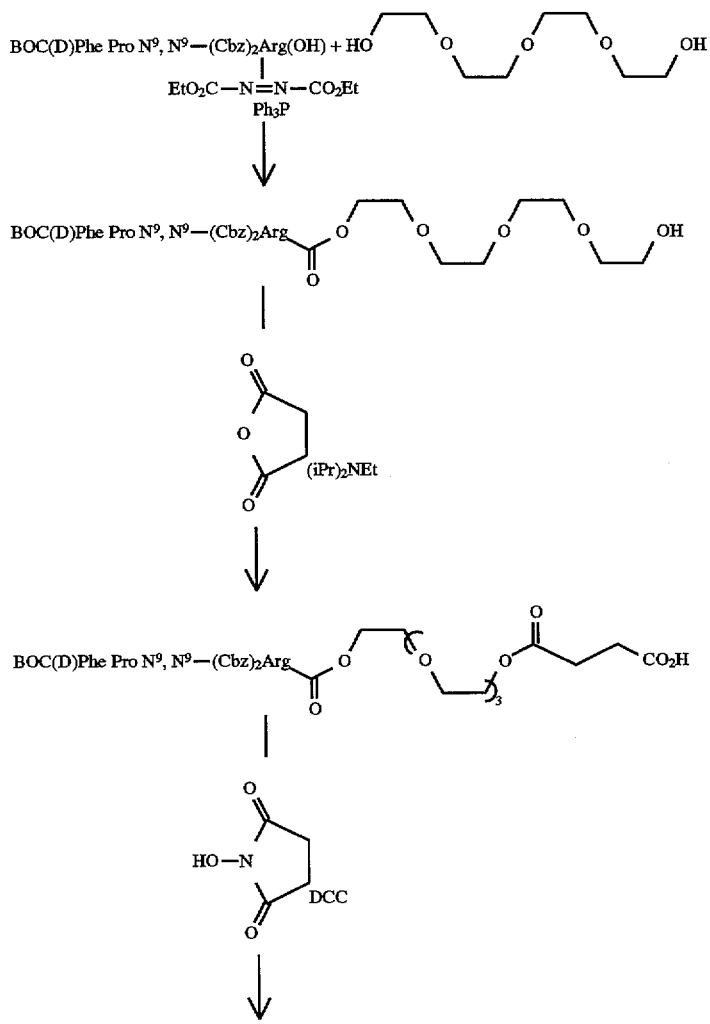

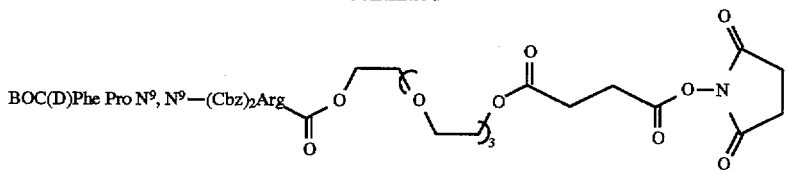

N$^\alpha$-BOC-(D-Phe)-Pro-N$^g$,N$^g$-(Cbz)$_2$-Arg

N$^\alpha$-BOC-N$^g$-(Cbz)$_2$-Arg (Bachem, Inc., Torrance, Calif.) is reacted with excess ethereal diazomethane and then treated with acid to remove the N$^\alpha$-BOC group. The resulting product, N$^g$,N$^g$-(Cbz)$_2$-Arginine methyl ester is then dissolved in DMF, cooled in an ice bath and treated with, in order, 2 equivalents of N$^\alpha$-BOC-proline, 1 equivalent of butanol, 1 equivalent of EDCI and 1 equivalent of diisopropylethylamine. The reaction mixture is stirred overnight, then diluted with 5 volume of cold water and extracted with ethyl acetate. The organic phase is recovered and washed successively with equal volumes of saturated citric acid, saturated NaHCO$_3$ and saturated NaCl. The product is then dried over MgS$_4$ and concentrated in vacuo. The resulting dipeptide intermediate, N$^\alpha$-BOC-prolyl-N$^g$,N$^g$-(Cbz)$_2$-Arginine methyl ester, is treated with a 10-fold molar excess of 4N HCl/dioxane for 30 minutes. The free HCl is removed in vacuo and the residue dissolved in anhydrous DMF. The product is then cooled in an ice bath and reacted with 2 equivalents of N$^\alpha$-BOC-(D-Phe) in the presence of butanol, EDCI and diisopropylethylamine, as described above. The crude, orthogonally protected tripeptide is isolated as described above and purified on a silica gel column eluted with chloroform:methanol (95:5) containing 0.1% NH$_4$OH. The N$^\alpha$-BOC-(D)-phenylalanylprolyl-N$^g$,N$^g$-(Cbz)$_2$-Arginine methyl ester is then saponified with 2 equivalents of LiOH in methanol::water (2:1) at room temperature for 3 hours. The methanol is removed in vacuo and the aqueous solution washed with 2 volumes of diethyl ether. The solution was then acidified to pH 3 with saturated citric acid. The resulting crude tripeptide free acid is extracted into ethyl acetate. The organic phase is washed with 3 volumes of saturated NaCl, dried over anhydrous MgSO$_4$ and concentrated in vacuo. The resulting N$^\alpha$-BOC-(D)-phenylalanylprolyl-N$^g$,N$^g$-(Cbz)$_2$-Arginine is purified by reverse-phase HPLC under conditions described in Example 4.

N$^\alpha$-BOC-(D)-phenylalanylprolyl-N$^g$,N$^g$-(Cbz)$_2$-Arginine Tetraethyleneglycol Ester A solution of the above tripeptide is dissolved in THF and esterified with 1.5 equivalents of tetraethylene glycol in the presence of 1 equivalent each of diethylazodicarboxylate and triphenylphosphine as described in O. Mitsunobu, "The Use of DiethylAzodicarboxylate and Triphenylphosphine in Synthesis and Transformation of Natural Products, Synthesis, pp. x1–28 (1981), the discosure of which is herein incorporated by reference.

N$^\alpha$-BOC-(D)phenylalanylprolyl-N$^g$,N$^g$-(Cbz)$_2$-Arginine Tetraethyleneglycolyl Hemisuccinate The resulting compound is dissolved in DMF and esterified with 1 equivalent of succinic anhydride in the presence of 1 equivalent of diisopropylethylamine. The volatile solvents are removed in vacuo and the free acid is purified by reverse-phase HPLC under conditions described in Example 4.

N$^\alpha$-BOC-(D)phenylalanylprolyl-N$^g$,N$^g$-(Cbz)$_2$-Arginine Tetraethyleneglycolyl Hemisuccinate N-Hydorxysuccinimide Ester A solution of the above acid is mixed with 1 equivalent of N-hydroxysuccinimide in DMF, cooled in an ice bath and mixed with 1 equivalent of DCC in DMF, added dropwise. The reaction is stirred at room temperature for 24 hours, filtered to remove the precipitated dicyclohexyl urea and concentrated in vacuo. The solution is then concentrated with cold benzene/hexane to give the crude peptide-glycol conjugated N-hydroxysuccinimide ester.

The above compound is reacted with the resin-bound dodecapeptide, as described in Example 21. The resulting Hirulog-34 is cleaved from the resin, purified and characterized as described in Example 4.

While we have hereinbefore presented a number of embodiments of this invention, it is apparent that our basic construction can be altered to provide other embodiments which utilize the molecules, compositions, combinations and methods of this invention. Therefore, it will be appreciated that the scope of this invention is to be defined by the claims appended hereto rather than the specific embodiments which have been presented hereinbefore by way of example.

We claim:

1. A method for coating the surface of an invasive device to be inserted into a patient, said method comprising the step of contacting said surface with a composition wherein said composition comprises
  a) a thrombin inhibitor consisting of
   i. a catalytic site-directed moiety that binds to and inhibits the active site of thrombin wherein said catalytic site-directed moiety is selected from general serine proteinase inhibitors, heterocyclic protease inhibitors, thrombin-specific inhibitors, transition state analogues, benzamidine, DAPA, NAPAP, argipidine, or moieties of the formulae:

$X-A_1-A_2-A_3Y$ or $X-C_1-C_2-A_3Y$, wherein X is hydrogen or is characterized by a backbone chain consisting of from 1 to 35 atoms; $A_1$ is Arg, Lys or Orn; $A_2$ is a non-amide bond; $A_3$ is characterized by a backbone chain consisting of from 1 to 9 atoms; Y is a bond; $C_1$ is a derivative of Arg, Lys or Orn comprising a carboxylate moiety that is reduced, or displaced from the α-carbon by a structure characterized by a backbone chain of from 1 to 10 atoms; and $C_2$ is a non-cleavable bond;
   ii. a linker moiety characterized by a backbone chain having a calculated length of between 18 Å and 42 Å; and
   iii. an anion binding exosite associating moiety;
  said catalytic site-directed moiety being bound to said linked moiety and said linker moiety being bound to said anion binding exosite moiety; and
  b) a buffer suitable to promote the binding of said thrombin inhibitor to said invasive device.

2. The method according to claim 1, wherein said anion binding exosite moiety consists of the formula:

wherein W is a bond; $B_1$ is an anionic amino acid; $B_2$ is any amino acid; $B_3$ is Ile, Val, Leu, Nle or Phe; $B_4$ is Pro, Hyp, 3,4-dehydroPro, thiazolidine-4-carboxylate, Sar, any N-methyl amino acid or D-Ala; $B_5$ is an anionic amino acid; $B_6$ is an anionic amino acid; $B_7$ is a lipophilic amino acid selected from the group consisting Tyr, Trp, Phe, Leu, Nle, Ile, Val, Cha, Pro, or a dipeptide consisting of one of these lipophilic amino acids and any amino acid; $B_8$ is a bond or a peptide containing form one to five residues of any amino acid; and Z is a carboxy terminal residue selected from OH, $C_1$–$C_6$ alkoxy, amino, mono- or di-($C_1$–$C_4$) alkyl substituted amino or benzylamino.

3. The method inhibitor according to claim 2, wherein $B_1$ is Glu; $B_2$ is Glu; $B_3$ is Ile; $B_4$ is Pro; $B_5$ is Glu; $B_6$ is Glu; $B_7$ is Tyr-Leu, Tyr($SO_3$H)-Leu, Tyr($OSO_3$H)-Leu or (3-, 5-diiodoTyr)-Leu; $B_8$ is a bond; and Z is OH.

4. The method inhibitor according to claim 1, wherein said backbone chain of said linker moiety consists of any combination of atoms selected from the group consisting of carbon, nitrogen, sulfur and oxygen.

5. The method inhibitor according to claim 4, wherein said linker comprises the amino acid sequence: Gly-Gly-Gly-Asn-Gly-Asp-Phe.

6. The method inhibitor according to claim 1, wherein said catalytic site-directed moiety binds reversibly to and is slowly cleaved by thrombin.

7. The method inhibitor according to claim 1, wherein said catalytic site-directed moiety binds reversibly to and cannot be cleaved by thrombin.

8. The method inhibitor according to claim 1, wherein said catalytic site-directed moiety binds irreversibly to thrombin.

9. The method inhibitor according to claim 1, wherein X is D-Phe-Pro; $A_1$ is Arg; and $A_3$ is D-Pro, Pro, or Sar.

10. The method inhibitor according to claim 9, wherein said thrombin inhibitor is selected from the group consisting of Hirulog-8 and Hirulog-12.

11. The method inhibitor according to claim 1, wherein X is N-acetyl-Gly-Asp-Phe-Leu-Ala-Glu-Gly-Gly-Gly-Val; $A_1$ is Arg; and $A_3$ is Pro, said thrombin inhibitor being Hirulog-33.

12. The method inhibitor according to claim 1, selected from the group consisting of Hirulog-18a and Hirulog-18b.

13. The method inhibitor according to claim 2, wherein said linker moiety is characterized by a backbone chain having a calculated length of between about 18 Å and 36 Å and is selected from the group consisting of an acyl group of from about 17 to 35 carbon atoms, carbobenzyloxy or t-butyloxy carbonyl, an alkyl group of from about 17 to 35 backbone bonds, a peptide containing from about 6 to 12 residues of any amino acid and combinations thereof.

14. The method inhibitor according to claim 3, wherein:

$B_7$ is Tyr($SO_3$H)-Leu or Tyr($OSO_3$H)-Leu;

the linker is a peptide of from about 8 to 10 amino acids, the amino acid of said linker which is closest to the anion binding exosite moiety being Phe; and
the catalytic site-directed moiety consists of the formula:

X-Arg-R, wherein X is selected from the group consisting of D-Phe-Pro and tosyl-Gly; and R is selected from group consisting of Pro, Sar and N-methyl Ala.

15. The method inhibitor according to claim 11, wherein said thrombin inhibitor is Hirulog-33.

* * * * *